US008703825B2

(12) United States Patent
Duval et al.

(10) Patent No.: US 8,703,825 B2
(45) Date of Patent: Apr. 22, 2014

(54) COMPOUNDS, USE THEREOF AS MEDICAMENTS, AND METHOD OF PREPARATION THEREOF

(75) Inventors: Raphaël Emmanuel Duval, Bioncourt (FR); Marion Grare, Paris (FR); Maxime Mourer, Pont A Mousson (FR); Jean-Bernard Regnouf-De-Vains, Saulxures-les-Nancy (FR)

(73) Assignee: Universite de Lorraine, Nancy (FR)

( * ) Notice: Subject to any disclaimer, the term of this patent is extended or adjusted under 35 U.S.C. 154(b) by 187 days.

(21) Appl. No.: 13/003,330

(22) PCT Filed: Jul. 10, 2009

(86) PCT No.: PCT/FR2009/051388
§ 371 (c)(1),
(2), (4) Date: Apr. 6, 2011

(87) PCT Pub. No.: WO2010/004231
PCT Pub. Date: Jan. 14, 2010

(65) Prior Publication Data
US 2011/0184070 A1 Jul. 28, 2011

(30) Foreign Application Priority Data
Jul. 10, 2008 (FR) ...................... 08 03940

(51) Int. Cl.
*A61K 31/155* (2006.01)
*C07C 277/00* (2006.01)
(52) U.S. Cl.
USPC ........................... 514/634; 564/236; 564/243
(58) Field of Classification Search
USPC .................. 514/634; 564/236, 243
See application file for complete search history.

(56) References Cited

U.S. PATENT DOCUMENTS

| 3,896,235 A | 7/1975 | Harfenist | |
|---|---|---|---|
| 4,231,964 A * | 11/1980 | Kuhne et al. | 564/441 |
| 2004/0147531 A1* | 7/2004 | Chalifour et al. | 514/256 |

FOREIGN PATENT DOCUMENTS

| GB | 938042 A | 9/1963 |
|---|---|---|
| WO | 03103598 A | 12/2003 |

OTHER PUBLICATIONS

DATABASE CA [Online] Chemical Abstracts Service, Columbus, Ohio, US; 1966, Ando, Tadanao et al: "Polycondensation of bis[p-(3-aminopropyl)phenoxy] alkanes and dialkyl ethers with diphenyl carbonate" XP002559220.
Dardonville, Christophe et al: "DNA Binding Affinity of 8isguanidine and Bis(2-aminoimidazoline) Derivatives with in Vivo Antitrypanosomal Activity", Journal of Medicinal Chemistry, 2006, pp. 3748-3752, 49(12), CODEN: JMCMAR; ISSN: 0022-2623, XP002513237.
McMillan, Freeman H.: "Diaryloxyalkane derivatives. Some miscellaneous diphenoxypropanes", Journal of the American Chemical Society,1952, pp. 5229-5230, 74, CODEN: JACSAT; ISSN: 0002-7863, XP002513238.
Gibson, Harry W. et al: "Supramolecular Pseudorotaxane Polymers from Complementary Pairs of Homoditopic Molecules", Journal of the American Chemical Society, 2003, pp. 3522-3533, 125(12), CODEN: JACSAT; ISSN: 0002-7863, 2003, XP002513239.
Willson Met Al: "Biological properties of amidinium sulfonic and sulfonic acid derivatives: inhibition of glycolytic enzymes of *Trypanosoma brucei* and protective effect on cell growth", European Journal of Medicinal Chemistry, Editions Scientifique Elsevier, Paris, FR, vol. 27, No. 8, Nov. 1, 1992, pp. 799-808, XP023870784.
Nordmann et al: "Superbugs in the coming new decade; multidrug resistance and prospects for treatment of *Staphylococcus aureus, Enterococcus* spp. and *Pseudomonas aeruginosa* in 2010", Current Opinion in Microbiology, Current Biology Ltd, GB, vol. 10, No. 5, Oct. 1, 2007, pp. 436-440, XP022338237.
Ando, Tadanao et al: "Polycondensation of bis[p-(3-aminopropyl)phenoxy] alkanes and dialkyl ethers with diphenyl carbonate", Yuki Gosei Kagaku Kyokaishi , 24(1) , 44-53 CODEN: YGKKAE; ISSN: 0037-9980, 1966, XP008116017.
European Search Report, dated Feb. 4, 2009, in FA 709981/FR 0803940.
International Search Report, dated Dec. 18, 2009, in PCT/FR2009/051388.

* cited by examiner

Primary Examiner — Rei-tsang Shiao
(74) Attorney, Agent, or Firm — Young & Thompson

(57) ABSTRACT

Novel compounds of the following formula (I):

(I)

in which:
n represents an integer from 1 to 12, in particular from 1 to 8,
m and m' represent, independently of one another, integers from 0 to 8,
q and q' represent, independently of one another, integers from 0 to 2,
p and p' represent, independently of one another, integers from 0 to 4,
A and A' represent, independently of one another, a $CH_2$ group, (particular case of amidines) an NH group or an NR" group, in which R" is a linear or branched alkyl group with 1 to 3 carbon atoms,
B and B' represent, independently of one another, an oxygen atom or a $CH_2$ group,
R and R' are, independently of one another, a halogen, such as chlorine, bromine, iodine or fluorine atoms, or a linear or branched alkyl group with 1 to 3 carbon atoms,
use thereof as medicaments and the method of preparation thereof.

13 Claims, No Drawings

COMPOUNDS, USE THEREOF AS MEDICAMENTS, AND METHOD OF PREPARATION THEREOF

The invention relates to novel compounds, use thereof as medicaments and the method of preparation thereof.

Numerous molecules having anti-infectious activity (antiseptics and/or antibiotics) are known and are marketed, for example hexamidine and chlorhexidine. However, the emergence of phenomena of resistance to these molecules has been observed, and consequently it is more than likely that these products will eventually become unusable on account of being ineffective.

At present, nosocomial infections (NIs) constitute a major public health problem. The agents responsible for NIs can be bacteria, viruses or fungi.

By the term nosocomial infection is meant any infection occurring within at least 48 h (for bacterial infections) or within a time corresponding to the period of incubation of the germ (for viral and fungal infections) after admission or after hospitalization, and if it was absent on admission to hospital. The nosocomial character of an infection of the site of surgery is affirmed if it occurs in the 30 days following surgery, or within a year in the case of implantation of foreign material (prosthesis, implant), even though the patient is no longer hospitalized.

NIs are worrying because of their considerable morbidity, associated mortality, appreciable additional hospital costs and the emergence of bacteria that are resistant to several families of antibiotics (MRB: Multiresistant Bacteria).

The NIs most frequently encountered are urinary tract infections (30%), respiratory tract infections (15%), infections of the site of surgery (14%) and infections of the skin and soft tissues (10%).

Among germs responsible for NIs, bacteria are at the forefront. Those most often implicated are *Escherichia coli* (25%) (a bacterium of the commensal gut flora, responsible for urinary tract infections), *Staphylococcus aureus* (19%) (bacterium of the commensal cutaneous and nasal flora, responsible for skin infections and infections of the site of surgery), *Pseudomonas aeruginosa* (10%) (opportunistic bacterium, responsible for severe pneumonias and skin infections), *Enterococcus* spp (6%) (bacterium of the commensal gut flora, essentially responsible for urinary tract infections).

Globally, the level of antibiotic resistance of the bacteria responsible for NIs is high and the proportion of MRB observed in France is among the highest in Europe; the countries of Northern Europe (Denmark, the Netherlands, Norway etc.) are characterized by a very low level of multiresistance to antibiotics. This worrying situation is associated with excessive and often unsuitable use of antibiotics: inappropriate prescriptions, incorrect doses, unsuitable duration of treatment, etc.

At present, 52% of *Staphylococcus aureus* isolated in hospital during NIs are methicillin-resistant (MRSA: Methicillin-Resistant *Staphylococcus aureus*), this antibiotic from the penicillin family constituting the reference treatment of staphylococci. In addition, there is emergence of strains of MRSA resistant to many other families of antibiotics: macrolides, aminoglycosides, fluoroquinolones, or even glycopeptides (antibiotics of choice in the treatment of staphylococcal infections, often the last resort in the case of severe infection). Other multiresistant hospital germs are problematic:

(i) enterobacteria that are resistant to β lactamines (15%) (ESBLPE: extended-spectrum β-lactamase-producing Enterobacteriaceae, the β lactamases being the enzymes responsible for the degradation of (β-lactamines), (ii) enterococci that are resistant to glycopeptides (10%) (VRE: vancomycin-resistant Enterococci, vancomycin being, with teicoplanin, one of the members of the glycopeptide family), (iii) *Pseudomonas aeruginosa* resistant to third-generation cephalosporins (25%), etc.

There is a risk of being faced with a therapeutic impasse:

either there is no longer a compound available for treating nosocomial infections, which are generally severe as they affect patients in a weakened state, or the compounds that are still available display toxicity such that their use is limited, or cannot even be considered.

Consequently, it is essential to propose alternative novel molecules having anti-infectious activity.

One aspect of the invention is to supply novel compounds for controlling bacterial, viral, fungal and parasitic infections.

One aspect of the invention relates to the use of compounds for preparing a medicament intended for the treatment of bacterial, viral, fungal and parasitic infections.

Generally, the invention relates to the use of at least one compound of the following formula (I):

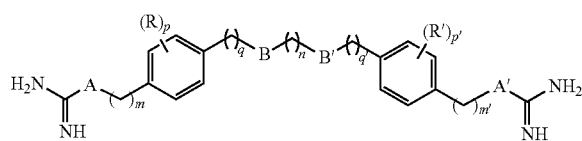

in which:

n represents an integer from 1 to 12, in particular from 1 to 8, m and m' represent, independently of one another, integers from 0 to 8, in particular 1 to 8, q and q' represent, independently of one another, integers from 0 to 2, p and p' represent, independently of one another, integers from 0 to 4, A and A' represent, independently of one another, a $CH_2$ group, an NH group or an NR" group, in which R" is a linear or branched alkyl group with 1 to 3 carbon atoms, B and B' represent, independently of one another, an oxygen atom or a $CH_2$ group, R and R' are, independently of one another, a halogen, such as chlorine, bromine, iodine or fluorine atoms, or a linear or branched alkyl group with 1 to 3 carbon atoms, or a physiologically acceptable acid salt derived from a compound of formula (I) such as a hydrochloride, a formate, a trifluoroacetate or an oxalate (HOOCCOOH), for preparing a medicament intended for the treatment of pathologies associated with bacterial, viral, fungal and parasitic infections.

By "Linear or branched alkyl group with 1 to 3 carbon atoms" is meant the methyl, ethyl, n-propyl and isopropyl groups.

By the expression "physiologically acceptable acid salt" is meant that the compounds of formula (I), defined above, can exist in the form of amidinium (when A and/or A' represent(s) —$CH_2$—) or of guanidinium (when A and/or A' represent(s) NH or NR") by reaction of an inorganic acid or of an organic acid, on a compound of formula (I).

Examples of inorganic acids permitting physiologically acceptable salts to be obtained include, without being limited to these, hydrochloric acid, hydrobromic acid, nitric acid, carbonic acid, formic acid, monohydrogen carbonic acid, phosphoric acid, monohydrogen phosphoric acid, dihydrogen phosphoric acid, perchloric acid, sulphuric acid, monohydrogen sulphuric acid, hydriodic acid.

Examples of organic acids permitting physiologically acceptable salts to be obtained include, without being limited to these, acetic acid, lactic acid, propionic acid, butyric acid, isobutyric acid, palmitic acid, maleic acid, glutamic acid, hydroxymaleic acid, malonic acid, benzoic acid, succinic acid, glycolic acid, suberic acid, fumaric acid, mandelic acid, phthalic acid, salicylic acid, benzenesulphonic acid, p-toluenesulphonic acid, citric acid, tartaric acid, methanesulphonic acid, hydroxynaphthoic acid.

The salts of amino acids, such as arginates and their equivalents, are also included as well as the salts of organic acids such as glucuronic acid or galacturonic acid and their equivalents (see, for example, Berge et al., "Pharmaceutical Salts", *Journal of Pharmaceutical Science*, 1977, 66, 1-19).

By the term "n represents an integer from 1 to 12" is meant all the integers 1, 2, 3, 4, 5, 6, 7, 8, 9, 10, 11 and 12. This definition applies to formula (I) but also to the other formulae given below.

By the term "m and m' represent, independently of one another, integers from 0 to 8" is meant all the integers 0, 1, 2, 3, 4, 5, 6, 7 and 8. This definition applies to formula (I) but also to the other formulae given below.

by the term "q and q' represent, independently of one another, integers from 0 to 2" is meant the integers 0, 1 and 2. This definition applies to formula (I) but also to the other formulae given below.

By the term "p and p' represent, independently of one another, integers from 0 to 4" is meant the integers 0, 1, 2, 3 and 4. This definition applies to formula (I) but also to the other formulae given below.

The invention also relates to the use of at least one compound of the following formula (I):

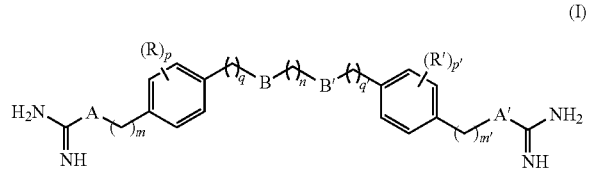

in which:
n represents an integer from 1 to 12, in particular from 1 to 8,
m and m' represent, independently of one another, integers from 2 to 8,
q and q' represent, independently of one another, integers from 0 to 2,
p and p' represent, independently of one another, integers from 0 to 4,
A and A' represent, independently of one another, a $CH_2$ group, an NH group or an NR" group, in which R" is a linear or branched alkyl group with 1 to 3 carbon atoms,
B and B' represent, independently of one another, an oxygen atom or a $CH_2$ group,
R and R' are, independently of one another, a halogen, such as chlorine, bromine, iodine or fluorine atoms, or a linear or branched alkyl group with 1 to 3 carbon atoms,
or a physiologically acceptable acid salt derived from a compound of formula (I) such as a hydrochloride, a formate, a trifluoroacetate or an oxalate (HOOCCOOH),
for preparing a medicament intended for the treatment of pathologies associated with bacterial, viral, fungal and parasitic infections.

The invention also relates to the use of at least one compound of the following formula (I):

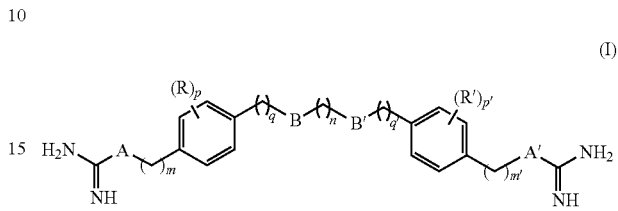

in which:
n represents an integer from 1 to 12, in particular from 1 to 8,
m and m' are equal to 2,
q and q' represent, independently of one another, integers from 0 to 2,
p and p' represent, independently of one another, integers from 0 to 4,
A and A' represent, independently of one another, a $CH_2$ group, an NH group or an NR" group, in which R" is a linear or branched alkyl group with 1 to 3 carbon atoms,
B and B' represent, independently of one another, an oxygen atom or a $CH_2$ group,
R and R' are, independently of one another, a halogen, such as chlorine, bromine, iodine or fluorine atoms, or a linear or branched alkyl group with 1 to 3 carbon atoms,
or a physiologically acceptable acid salt derived from a compound of formula (I) such as a hydrochloride, a formate, a trifluoroacetate or an oxalate (HOOCCOOH),
for preparing a medicament intended for the treatment of pathologies associated with bacterial, viral, fungal and parasitic infections.

The invention also relates to the use of at least one compound of the following formula (I):

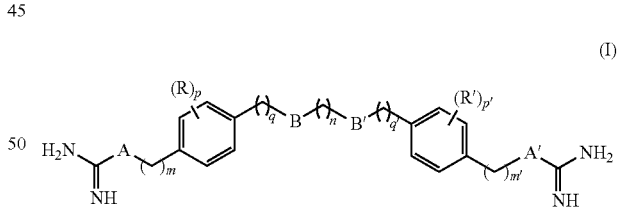

in which:
n represents an integer from 1 to 12, in particular from 1 to 8,
m and m' represent, independently of one another, integers from 0 to 8, in particular 1 to 8,
q and q' are equal to 0,
p and p' represent, independently of one another, integers from 0 to 4,
A and A' represent, independently of one another, a $CH_2$ group, an NH group or an NR" group, in which R" is a linear or branched alkyl group with 1 to 3 carbon atoms,
B and B' represent, independently of one another, an oxygen atom or a $CH_2$ group, R and R' are, independently of one another, a halogen, such as chlorine, bromine, iodine or fluorine atoms, or a linear or branched alkyl group with 1 to 3 carbon atoms, or a physiologically acceptable acid salt derived from a compound of formula (I) such as a hydrochloride, a formate, a trifluoroacetate or an oxalate (HOOCCOOH), for preparing a medicament intended for the treatment of pathologies associated with bacterial, viral, fungal and parasitic infections.

The invention also relates to the use of at least one compound of the following formula (I):

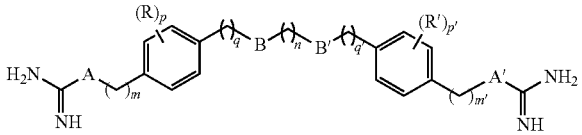

(I)

in which:

n represents an integer from 1 to 12, in particular from 1 to 8, m and m' represent, independently of one another, integers from 0 to 8, in particular 1 to 8, q and q' represent, independently of one another, integers from 0 to 2, p and p' are equal to 0, A and A' represent, independently of one another, a CH$_2$ group, an NH group or an NR" group, in which R" is a linear or branched alkyl group with 1 to 3 carbon atoms, B and B' represent, independently of one another, an oxygen atom or a CH$_2$ group, or a physiologically acceptable acid salt derived from a compound of formula (I) such as a hydrochloride, a formate, a trifluoroacetate or an oxalate (HOOCCOOH), for preparing a medicament intended for the treatment of pathologies associated with bacterial, viral, fungal and parasitic infections.

The invention also relates to the use of at least one compound of the following formula

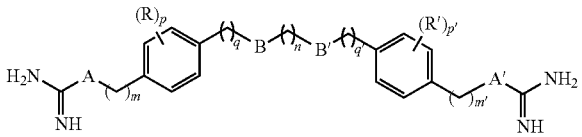

(I)

in which:

n represents an integer from 1 to 12, in particular from 1 to 8, m and m' are equal to 2, q and q' are equal to 0, p and p' represent, independently of one another, integers from 0 to 4, A and A' represent, independently of one another, a CH$_2$ group, an NH group or an NR" group, in which R" is a linear or branched alkyl group with 1 to 3 carbon atoms, B and B' represent, independently of one another, an oxygen atom or a CH$_2$ group, R and R' are, independently of one another, a halogen, such as chlorine, bromine, iodine or fluorine atoms, or a linear or branched alkyl group with 1 to 3 carbon atoms, or a physiologically acceptable acid salt derived from a compound of formula (I) such as a hydrochloride, a formate, a trifluoroacetate or an oxalate (HOOCCOOH), for preparing a medicament intended for the treatment of pathologies associated with bacterial, viral, fungal and parasitic infections.

The invention also relates to the use of at least one compound of the following formula (I):

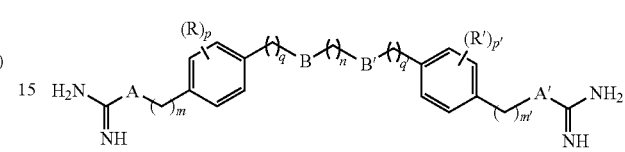

(I)

in which:

n represents an integer from 1 to 12, in particular from 1 to 8, m and m' are equal to 2, q and q' represent, independently of one another, integers from 0 to 2, p and p' are equal to 0, A and A' represent, independently of one another, a CH$_2$ group, an NH group or an NR" group, in which R" is a linear or branched alkyl group with 1 to 3 carbon atoms, B and B' represent, independently of one another, an oxygen atom or a CH$_2$ group, or a physiologically acceptable acid salt derived from a compound of formula (I) such as a hydrochloride, a formate, a trifluoroacetate or an oxalate (HOOCCOOH), for preparing a medicament intended for the treatment of pathologies associated with bacterial, viral, fungal and parasitic infections.

The invention also relates to the use of at least one compound of the following formula (I):

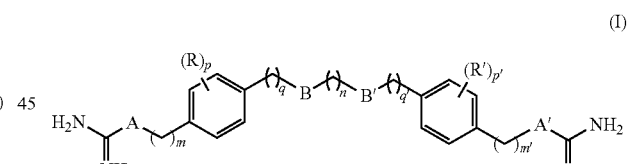

(I)

in which:

n represents an integer from 1 to 12, in particular from 1 to 8, m and m' represent, independently of one another, integers from 0 to 8, in particular 1 to 8, q and q' are equal to 0, p and p' are equal to 0, A and A' represent, independently of one another, a CH$_2$ group, an NH group or an NR" group, in which R" is a linear or branched alkyl group with 1 to 3 carbon atoms, B and B' represent, independently of one another, an oxygen atom or a CH$_2$ group, or a physiologically acceptable acid salt derived from a compound of formula (I) such as a hydrochloride, a formate, a trifluoroacetate or an oxalate (HOOCCOOH), for preparing a medicament intended for the treatment of pathologies associated with bacterial, viral, fungal and parasitic infections.

The invention also relates to the use of at least one compound of the following formula (I):

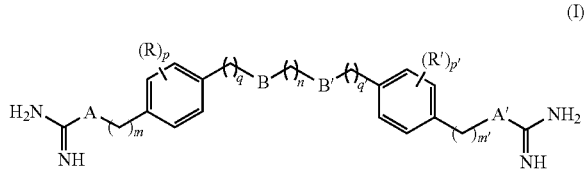
(I)

in which:
n represents an integer from 1 to 12, in particular from 1 to 8,
m and m' are equal to 2,
q and q' are equal to 0,
p and p' are equal to 0,
A and A' represent, independently of one another, a $CH_2$ group, an NH group or an NR" group, in which R" is a linear or branched alkyl group with 1 to 3 carbon atoms,
B and B' represent, independently of one another, an oxygen atom or a $CH_2$ group,
or a physiologically acceptable acid salt derived from a compound of formula (I) such as a hydrochloride, a formate, a trifluoroacetate or an oxalate (HOOCCOOH),
for preparing a medicament intended for the treatment of pathologies associated with bacterial, viral, fungal and parasitic infections.

The invention also relates to the use of at least one compound of the following formula (Ia):

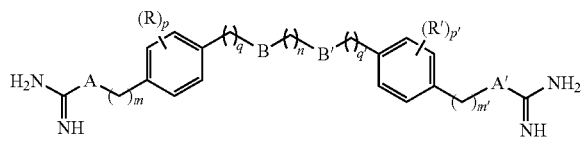
(Ia)

in which:
n represents an integer from 1 to 12, in particular from 1 to 8,
m and m' represent, independently of one another, integers from 0 to 8, in particular 1 to 8,
q and q' represent, independently of one another, integers from 0 to 2,
p and p' represent, independently of one another, integers from 0 to 4,
A and A' represent, independently of one another, an NH group or an NR" group, in which R" is a linear or branched alkyl group with 1 to 3 carbon atoms,
B and B' represent, independently of one another, an oxygen atom or a $CH_2$ group,
R and R' are, independently of one another, a halogen, such as chlorine, bromine, iodine or fluorine atoms, or a linear or branched alkyl group with 1 to 3 carbon atoms,
or a physiologically acceptable acid salt derived from a compound of formula (I) such as a hydrochloride, a formate, a trifluoroacetate or an oxalate (HOOCCOOH),
for preparing a medicament intended for the treatment of pathologies associated with bacterial, viral, fungal and parasitic infections.

The compounds of formula (Ia) correspond to the compounds of formula (I) in which A and A' represent, independently of one another, an NH group or an NR" group.

According to an advantageous embodiment of the invention, the formula of the compounds for the use as defined above is the following formula (II):

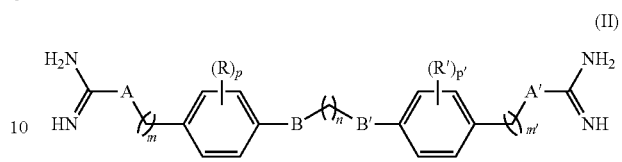
(II)

in which:
B, B', R, R', m, m', n, p, p' are as defined above, and,
A and A' represent, independently of one another, a $CH_2$ group, an NH group or an
NR" group, in which R" is a linear or branched alkyl group with 1 to 3 carbon atoms,
or a physiologically acceptable acid salt derived from a compound of formula (II) such as a hydrochloride, a formate, a trifluoroacetate or an oxalate (HOOCCOOH).

The formula of the compounds of formula (II) corresponds to formula (I), in which q and q' are equal to 0.

According to a particular embodiment of the invention, the formula of the compounds for the use as defined above is the following formula (II'):

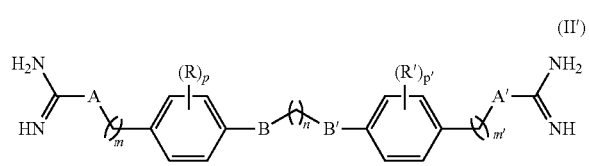
(II')

in which:
B, B', R, R', m, m', n, p, p' are as defined above, and,
A and A' represent, independently of one another, an NH group or an NR" group, in which R" is a linear or branched alkyl group with 1 to 3 carbon atoms,
or a physiologically acceptable acid salt derived from a compound of formula (II') such as a hydrochloride, a formate, a trifluoroacetate or an oxalate (HOOCCOOH).

The formula of the compounds of formula (II') corresponds to formula (Ia), in which q and q' are equal to 0.

According to an advantageous embodiment of the invention, the formula of the compounds for the use as defined above is the following formula (III):

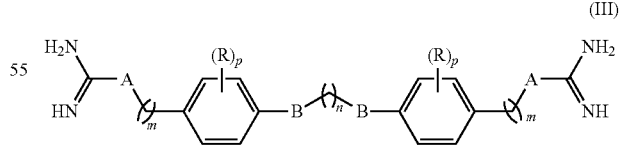
(III)

in which:
B, R, m, n, p are as defined above, and,
A represents a $CH_2$ group, an NH group or an NR" group, in which R" is a linear or branched alkyl group with 1 to 3 carbon atoms,
or a physiologically acceptable acid salt derived from a compound of formula (III) such as a hydrochloride, a formate, a trifluoroacetate or an oxalate (HOOCCOOH).

The formula of the compounds of formula (III) corresponds to formula (II), in which:

m and m' on the one hand, and p and p' on the other hand, are equal, and,

A and A' on the one hand, and B and B' on the other hand, represent the same atom or group.

In this embodiment, the compounds of formula (III) are symmetrical.

The advantage of the molecules of formula (III) is that the method of preparation is facilitated by the fact that these molecules are symmetrical.

According to an advantageous embodiment of the invention, the formula of the compounds for the use as defined above is the following formula (III'):

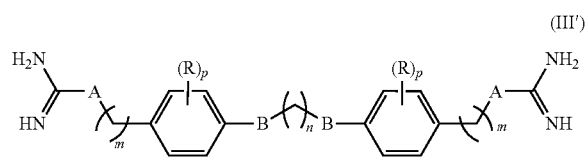

(III')

in which:

B, R, m, n, p are as defined above, and

A represents an NH group or an NR" group, in which R" is a linear or branched alkyl group with 1 to 3 carbon atoms, or a physiologically acceptable acid salt derived from a compound of formula (III) such as a hydrochloride, a formate, a trifluoroacetate or an oxalate (HOOCCOOH).

The formula of the compounds of formula (III') corresponds to formula (II'), in which:

m and m' on the one hand, and p and p' on the other hand, are equal, and,

A and A' on the one hand, and B and B' on the other hand, represent the same atom or group.

In this embodiment, the compounds of formula (III') are symmetrical.

According to an advantageous embodiment of the invention, the formula of the compound for the use as defined above is the following formula (IV):

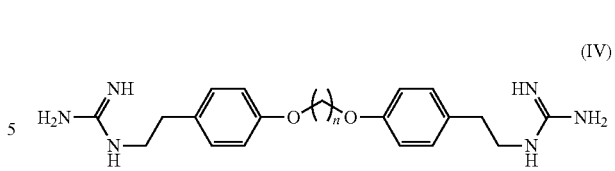

(IV)

in which n represents 1, 2, 3, 4, 5, 6, 7, 8, 9, 10, 11 or 12, or a physiologically acceptable acid salt derived from a compound of formula (IV).

The formula of the compounds of formula (IV) corresponds to formula (III), in which A represents an NH group, B represents an oxygen atom, p is equal to 0 and m is equal to 2. In this embodiment, the compounds of formula (IV) are symmetrical.

The advantage of the molecules of formula (IV) is that the method of preparation is facilitated by the fact that these molecules are symmetrical.

According to an advantageous embodiment of the invention, the formula of the compound for the use as defined above is the following formula 6:

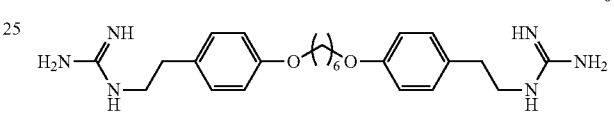

6 or a physiologically acceptable acid salt derived from a compound of formula 6 such as a hydrochloride, a formate, a trifluoroacetate or an oxalate (HOOCCOOH).

The formula of the compounds of formula 6 corresponds to formula (IV), in which n is equal to 6. In this embodiment, the compound of formula 6 is symmetrical.

According to another embodiment of the invention, the formula of the compound for the use as defined above is formula (II) as defined above in which:
m is different from m', and/or
p is different from p', and/or
R is different from R', and/or
A is different from A', and/or
B is different from B'.

In this embodiment, the compounds having said formula are not symmetrical.

According to a particular embodiment, the compounds of the invention are involved in the treatment of pathologies caused by the bacteria in Table 1.

TABLE 1

Bacteria causing pathologies treated with the compounds of the invention

| Aerobic/facultative aerobic-anaerobic bacteria | | | |
|---|---|---|---|
| Gram-positive | Gram-negative | Anaerobes | Others |
| *Staphylococcus* spp. | *Escherichia coli* | *Clostridium* spp. | *Mycobacterium* spp. |
| *Streptococcus* spp. | *Salmonella* spp. | including | including |
| *Streptococcus pneumoniae* | *Shigella* spp. | *C. difficile* | *M. tuberculosis* |
| | *Proteus* spp. | *Bacteroid* spp. | *Treponema* spp. |
| *Enterococcus* spp. | *Klebsiella* spp. | *Propionibacterium acnes* | including *T. pallidum* |
| *Bacillus* spp. | *Enterobacter* spp. | | *Legionella* spp. |
| including *B. anthracis* | *Citrobacter* spp. | *Prevotella* spp. | including |
| *Corynebacterium* spp. | *Serratia* spp. | *Porphyromonas* spp. | *L. pneumophila* |
| including *C. diphteriae* | *Providencia* spp. | | *Listeria* spp. |
| *Erysipelothrix rhusopathiae* | *Morganella* spp. | *Fusobacterium* spp. | including |
| | *Yersinia* spp. | *Bifidobacterium* spp. | *L. monocytogenes* |
| | *Vibrio* spp. | | *Chlamydia* spp. |
| | including *V. cholerae* | *Eubacterium* spp. | *Chlamydophila* spp. |

TABLE 1-continued

Bacteria causing pathologies treated with the compounds of the invention

Aerobic/facultative aerobic-anaerobic bacteria

| Gram-positive | Gram-negative | Anaerobes | Others |
|---|---|---|---|
| | *Campylobacter* spp. | *Peptococcus* spp. | *Borrelia* spp. |
| | *Pasteurella* spp. | *Peptostreptococcus* spp. | *Brucella* spp. |
| | *Haemophilus* spp. | | *Mycoplasma* spp. |
| | *Bordetella* spp. including *B. pertussis* | *Veillonella* spp. | *Ureaplasma* spp. |
| | | *Actinomyces* spp. | *Leptospira* spp. |
| | *Neisseria* spp. including *N. gonorrhoeae* and *N. meningitidis* | | *Rickettsia* spp. |
| | | | *Francisella tularensis* |
| | | | *Nocardia* spp. |
| | | | *Coxialla burnetii* |
| | *Moraxella catarrhalis* | | *Bartonella* spp. |
| | *Helicobacter pylori* | | |
| | *Pseudomonas* spp. | | |
| | *Burkholderia* spp. | | |
| | *Stenotrophomonas maltophilia* | | |
| | *Acinetobacter* spp. | | |
| | *Aeromonas* spp. | | |

According to another embodiment, the compounds of the invention are involved in the treatment of pathologies due to multiresistant bacteria (MRB) responsible for nosocomial and/or community-acquired infections.

According to another embodiment, the compounds of the invention are involved in the treatment of pathologies caused by viruses belonging to various families, such as: viral hepatitis A, B & D, C (Picornaviridae, Hepadnaviridae, Flaviviridae families); AIDS, leukaemia, cancer etc. (Retroviridae family); smallpox etc. (Poxyiridae family); buccal and/or genital herpes, chickenpox, shingles, mononucleosis, roseola, lymphoma etc. (Herpesviridae family); SARS, colds etc. (Coronaviridae family); infectious erythema (Parvoviridae family); certain cancers etc. (Papovavirus, Polyoviridae & Papillomaviridae families); poliomyelitis and meningitis, viral hepatitis A (Picornaviridae family); influenza (Orthomyxoviridae family); arboviroses (Flaviviridae, Togaviridae, Rhabdoviridae, Reoviridae families); Lassa fever etc. (Arenaviridae family), haemorrhagic fevers (Bunyaviridae family) etc.

According to another embodiment, the compounds of the invention are involved in the treatment of pathologies caused by fungi, in particular the following fungi: *Candida* spp., *Aspergillus* spp., *Epidermophyton* spp., *Trichophyton* spp., *Microsporum* spp., and *Pneumocystis jiroveci*.

According to another embodiment, the compounds of the invention are involved in the treatment of pathologies caused by the parasites in Table 2.

TABLE 2

Parasites causing pathologies treated with compounds according to the invention

| Zoonoses | Platyhelminthes | Nemathelminthes |
|---|---|---|
| *Entamoeba* spp. | *Fasciola hepatica* | *Ancylostoma duodenalis* |
| *Pseudolimax* spp. | *Dicrocoelum dendriticum* | *Necator americanus* |
| *Endolimax* spp. | | *Ascaris lumbricoides* |
| *Dientamoeba* spp. | *Schistosoma* spp. | *Trichuris trichiura* |
| *Balantidium* coli | *Echinococcus* spp. | *Trichocephalus trichiurus* |
| *Giardia intestinalis* | | *Anisakis* spp. |
| *Trichomonas* spp. | *Taenia* spp. | *Toxocara* spp. |
| *Trypanosoma* spp. | | *Wuchereria* spp. |
| *Toxoplasma gondii* | | *Brugia* spp. |
| *Plasmodium* spp. | | *Loa loa* |
| *Leishmania* spp. | | *Onchocerca volvulus* |
| *Cryptosporidium* spp. | | *Dracunculus medinensis* |
| *Encephalitozoon* spp. | | *Mansonella* spp. |
| *Enterocytozoon* spp. | | *Strongyloides* spp. |
| *Cydospora cayetanensis* | | *Trichinella* spp. |
| *Isospora belli* | | *Enterobius vermicularis* |
| *Sarcocystis* spp. | | |
| *Babesia* spp. | | |

Said pathologies caused by parasites can be for example parasitic diseases due to Protozoa or to worms, scabies, myiases and lice infestations.

According to another aspect, the invention relates to the compound of the following formula (VI):

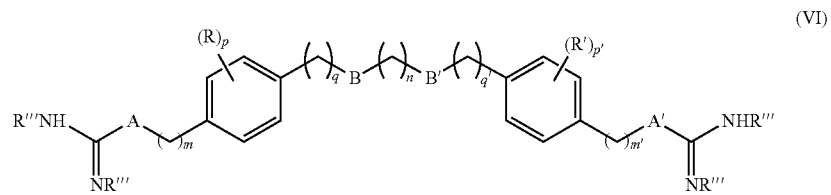

in which:
n represents an integer from 1 to 12, in particular from 1 to 8,
q and q' represent, independently of one another, integers from 0 to 2,
p and p' represent, independently of one another, integers from 0 to 4,
B and B' represent, independently of one another, an oxygen atom or a CH$_2$ group,
R and R' represent, independently of one another, a halogen, such as chlorine, bromine, iodine or fluorine atoms, or a linear or branched alkyl group with 1 to 3 carbon atoms,
R''' represents a hydrogen or a group protecting the amine function in particular selected from the groups Boc, Fmoc, Bn, Z,
if A and A' represent, independently of one another, a CH$_2$ group, then m and m' represent, independently of one another, integers from 1 to 8,
if A and A' represent, independently of one another, an NH group or an NR'' group, in which R'' is a linear or branched alkyl group with 1 to 3 carbon atoms, then m and m' represent, independently of one another, integers from 2 to 8,
or a physiologically acceptable acid salt derived from a compound of formula (VI) such as a hydrochloride, a formate, a trifluoroacetate or an oxalate (HOOCCOOH),
the compounds of the following formulae being excluded:

gen phosphoric acid, perchloric acid, sulphuric acid, monohydrogen sulphuric acid, hydriodic acid.

Examples of organic acids permitting physiologically acceptable salts to be obtained include, without being limited to these, acetic acid, lactic acid, propionic acid, butyric acid, isobutyric acid, palmitic acid, maleic acid, glutamic acid, hydroxymaleic acid, malonic acid, benzoic acid, succinic acid, glycolic acid, suberic acid, fumaric acid, mandelic acid, phthalic acid, salicylic acid, benzenesulphonic acid, p-toluenesulphonic acid, citric acid, tartaric acid, methanesulphonic acid, hydroxynaphthoic acid.

The salts of amino acids, such as arginates and their equivalents are also included as well as the salts of organic acids such as glucuronic acid or galacturonic acid and their equivalents (see, for example, Berge et al., "Pharmaceutical Salts", *Journal of Pharmaceutical Science,* 1977, 66, 1-19).

Note that the groups "Boc" (or boc), "Fmoc, Bn, Z" represent, respectively, the t-butoxycarbonyl, fluorenyl-9-methoxycarbonyl, benzyl and benzyloxycarbonyl groups.

According to an advantageous embodiment, the invention relates to the compound of formula (VI) defined above, in which:
m and m' represent, independently of one another, integers from 2 to 8.

According to an advantageous embodiment, the invention relates to the compound of formula (VI) defined above, in which:
m and m' are equal to 2.

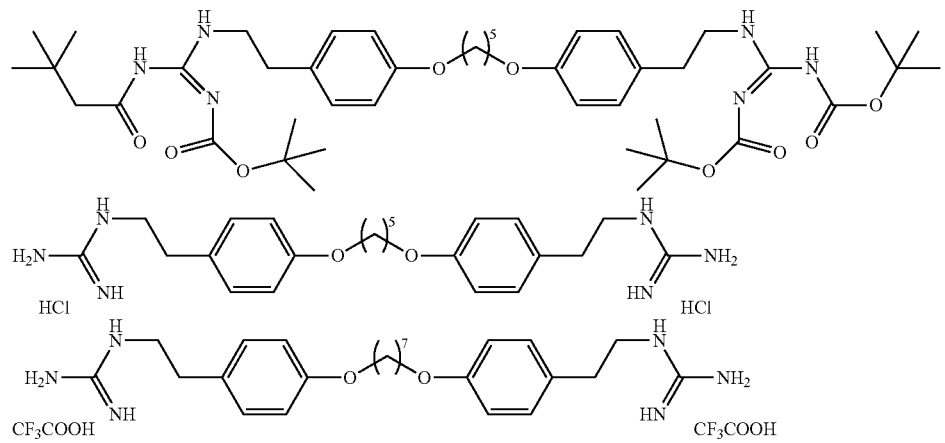

The novel compounds defined above can be used according to the present invention.

The compounds of formula (VI), apart from the above two compounds, are novel.

By "linear or branched alkyl group with 1 to 3 carbon atoms" is meant the methyl, ethyl, n-propyl and isopropyl groups.

By the expression "physiologically acceptable acid salt" is meant that the compounds of formula (I), defined above, can exist in the form of amidinium (when A and/or A' represent(s) —CH$_2$—) or of guanidinium (when A and/or A' represent(s) NH or NR'') by reaction of an inorganic acid or of an organic acid, on a compound of formula (I).

Examples of inorganic acids permitting physiologically acceptable salts to be obtained include, without being limited to these, hydrochloric acid, hydrobromic acid, nitric acid, carbonic acid, formic acid, monohydrogen carbonic acid, phosphoric acid, monohydrogen phosphoric acid, dihydro- According to an advantageous embodiment, the invention relates to the compound of formula (VI) defined above, in which:
q and q' are equal to 0.

According to an advantageous embodiment, the invention relates to the compound of formula (VI) defined above, in which:
p and p' are equal to 0.

According to an advantageous embodiment, the invention relates to the compound of formula (VI) defined above, in which:
m and m' are equal to 2, and
q and q' are equal to 0 to 2.

According to an advantageous embodiment, the invention relates to the compound of formula (VI) defined above, in which:
m and m' are equal to 2, and
p and p' are equal to 0.

According to an advantageous embodiment, the invention relates to the compound of formula (VI) defined above, in which:
q and q' are equal to 0, and
p and p' are equal to 0.

According to an advantageous embodiment, the invention relates to the compound of formula (VI) defined above, in which:
m and m' are equal to 2,
q and q' are equal to 0, and
p and p' are equal to 0.

According to an advantageous embodiment, the invention relates to the compound of formula (VI) defined above, in which:
n represents an integer from 6 to 12, in particular from 8 to 10.

According to an advantageous embodiment, the invention relates to the compound of formula (VI) defined above, in which:
R, R' represent, independently of one another, a linear or branched alkyl group with 1 to 3 carbon atoms.

According to an advantageous embodiment, the invention relates to the compound of formula (VI) defined above, in which:
p and p' are equal to 0.

According to an advantageous embodiment, the invention relates to the compound of formula (VI) defined above, in which:
n represents an integer from 6 to 12, in particular from 8 to 10, and
R, R' represent, independently of one another, a linear or branched alkyl group with 1 to 3 carbon atoms.

According to an advantageous embodiment, the invention relates to the compound of formula (VI) defined above, in which:
n represents an integer from 6 to 12, in particular from 8 to 10, and
p and p' are equal to 0.

The invention also relates to the compound of the following formula (VI'):

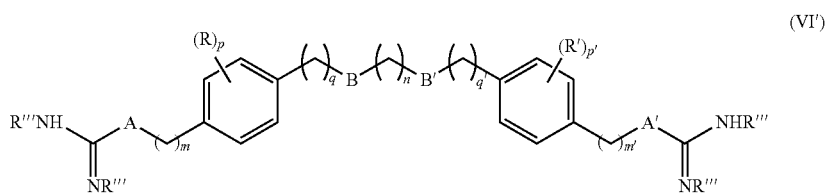

in which:
n represents an integer from 1 to 12, in particular from 1 to 8,
q and q' represent, independently of one another, integers from 0 to 2,
p and p' represent, independently of one another, integers from 0 to 4,
B and B' represent, independently of one another, an oxygen atom or a $CH_2$ group,
R and R' represent, independently of one another, a halogen, such as chlorine, bromine, iodine or fluorine atoms, or a linear or branched alkyl group with 1 to 3 carbon atoms,
R''' represents a hydrogen or a group protecting the amine function in particular selected from the groups Boc, Fmoc, Bn, Z,
A and A' represent, independently of one another, an NH group or an NR'' group, in which R'' is a linear or branched alkyl group with 1 to 3 carbon atoms, then m and m' represent, independently of one another, integers from 2 to 8,
or a physiologically acceptable acid salt derived from a compound of formula (VI) such as a hydrochloride, a formate, a trifluoroacetate or an oxalate (HOOCCOOH),
the compounds of the following formulae being excluded:

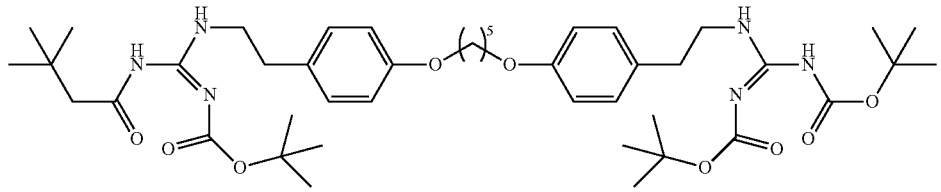

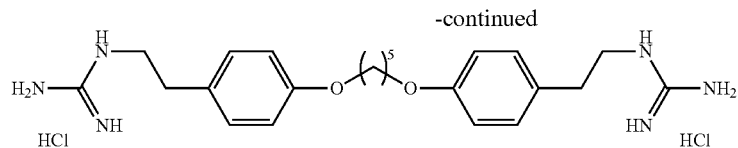

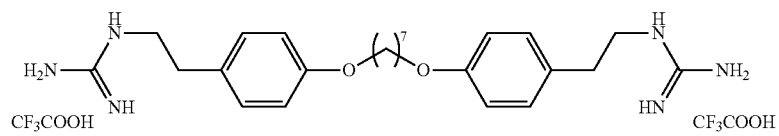

The novel compounds defined above can be used according to the present invention.

The formula of the compounds of formula (VI') corresponds to formula (VI) with A and A' representing independently of one another an NH group or an NR" group.

According to an advantageous embodiment, the invention relates to compounds of the following formula (I):

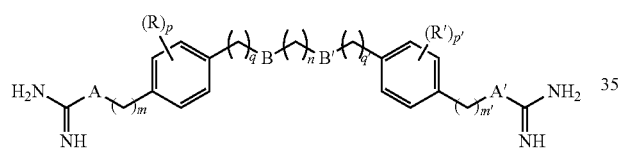

in which:

n represents an integer from 1 to 12, in particular from 1 to 8, q and q' represent, independently of one another, integers from 0 to 2, p and p' represent, independently of one another, integers from 0 to 4, B and B' represent, independently of one another, an oxygen atom or a $CH_2$ group, R and R' represent, independently of one another, a halogen, such as chlorine, bromine, iodine or fluorine atoms, or a linear or branched alkyl group with 1 to 3 carbon atoms, if A and A' represent, independently of one another, a $CH_2$ group, then m and m' represent, independently of one another, integers from 1 to 8, if A and A' represent, independently of one another, an NH group or an NR" group, in which R" is a linear or branched alkyl group with 1 to 3 carbon atoms, then m and m' represent, independently of one another, integers from 2 to 8, or a physiologically acceptable acid salt derived from a compound of formula (I) such as a hydrochloride, a formate, a trifluoroacetate or an oxalate (HOOCCOOH), the compounds of the following formulae being excluded:

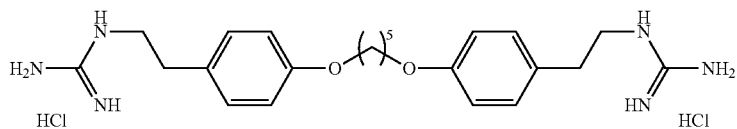

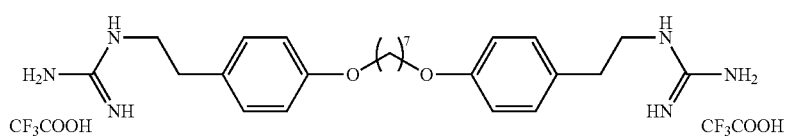

The formula of the compounds of formula (I) corresponds to formula (VI), in which R" represents a hydrogen. The compounds of formula (I) above, apart from the above two compounds, are novel.

The novel compounds defined above can be used according to the present invention.

The invention also relates to compounds of the following formula (Ia):

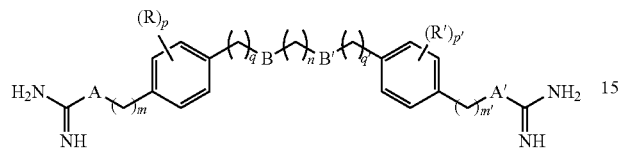
(Ia)

in which:
n represents an integer from 1 to 12, in particular from 1 to 8,
m and m' represent, independently of one another, integers from 2 to 8,
q and q' represent, independently of one another, integers from 0 to 2,
p and p' represent, independently of one another, integers from 0 to 4,
A and A' represent, independently of one another, an NH group or an NR" group, in which R" is a linear or branched alkyl group with 1 to 3 carbon atoms,
B and B' represent, independently of one another, an oxygen atom or a CH$_2$ group,
R and R' are, independently of one another, a halogen, such as chlorine, bromine, iodine or fluorine atoms, or a linear or branched alkyl group with 1 to 3 carbon atoms,
or a physiologically acceptable acid salt derived from a compound of formula (Ia) such as a hydrochloride, a formate, a trifluoroacetate or an oxalate (HOOCCOOH),
the compounds of the following formulae being excluded:

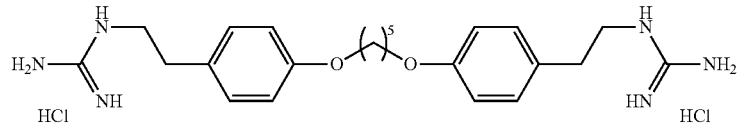

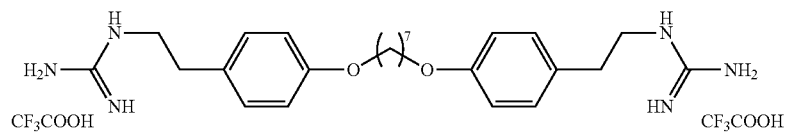

The formula of the compounds of formula (Ia) corresponds to formula (VI'), in which R" represents a hydrogen. The formula of the compounds of formula (Ia) corresponds to formula (I), in which A and A' represent, independently of one another, an NH group or an NR" group.

The novel compounds defined above can be used according to the present invention.

The invention also relates to compounds of the following formula (Ib):

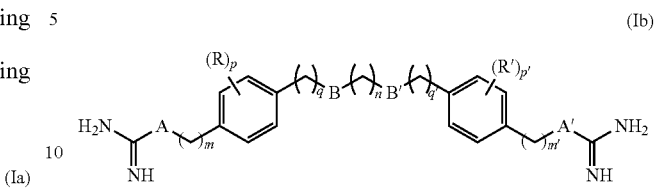
(Ib)

in which:
n represents an integer from 1 to 12, in particular from 1 to 8,
m and m' represent, independently of one another, integers from 1 to 8,
q and q' represent, independently of one another, integers from 0 to 2,
p and p' represent, independently of one another, integers from 0 to 4,
B and B' represent, independently of one another, an oxygen atom or a CH$_2$ group,
R and R' are, independently of one another, a halogen, such as chlorine, bromine, iodine or fluorine atoms, or a linear or branched alkyl group with 1 to 3 carbon atoms,
or a physiologically acceptable acid salt derived from a compound of formula (Ib) such as a hydrochloride, a formate, a trifluoroacetate or an oxalate (HOOCCOOH).

The formula of the compounds of formula (Ib) corresponds to formula (I), in which A and A' represent a CH$_2$ group.

The novel compounds defined above can be used according to the present invention.

According to an advantageous embodiment, the invention relates to compounds of the following formula (II):

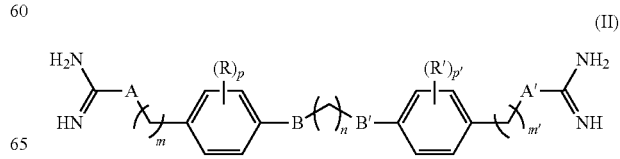
(II)

in which:

B, B', R, R', n, p, p' are as defined above, and,
  if A and A' represent, independently of one another, a CH$_2$ group, then m and m' represent, independently of one another, integers from 1 to 8,
  if A and A' represent, independently of one another, an NH group or an NR" group, in which R" is a linear or branched alkyl group with 1 to 3 carbon atoms, then m and m' represent, independently of one another, integers from 2 to 8, or a physiologically acceptable acid salt derived from a compound of formula (II) such as a hydrochloride, a formate, a trifluoroacetate or an oxalate (HOOCCOOH).

The formula of the compounds of formula (II) corresponds to formula (I), in which q and q' are equal to 0. The compounds of formula (II) above, apart from the above two compounds, are novel.

The novel compounds defined above can be used according to the present invention.

According to an advantageous embodiment, the invention relates to compounds of the following formula (II'):

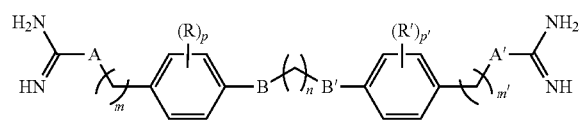

(II')

in which:

B, B', R, R', n, p, p' are as defined above, and
  A and A' represent, independently of one another, an NH group or an NR" group, in which R" is a linear or branched alkyl group with 1 to 3 carbon atoms,
  m and m' represent, independently of one another, integers from 2 to 8, or a physiologically acceptable acid salt derived from a compound of formula (II') such as a hydrochloride, a formate, a trifluoroacetate or an oxalate (HOOCCOOH).

The formula of the compounds of formula (II') corresponds to formula (Ia), in which q and q' are equal to 0. The formula of the compounds (II') corresponds to formula (II), in which A and A' represent, independently of one another, an NH group or an NR" group.

The novel compounds defined above can be used according to the present invention.

According to an advantageous embodiment, the invention relates to compounds of the following formula (III):

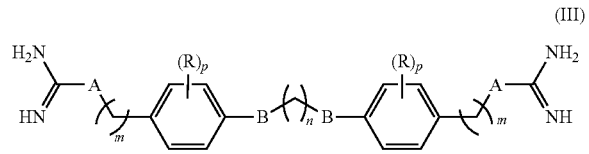

(III)

in which:

B, R, n, p are as defined above, and,
  if A represents a CH$_2$ group, then m represents an integer from 1 to 8,
  if A represents an NH group or an NR" group, in which R" is a linear or branched alkyl group with 1 to 3 carbon atoms, then m represents an integer from 2 to 8, or a physiologically acceptable acid salt derived from a compound of formula (III) such as a hydrochloride, a formate, a trifluoroacetate or an oxalate (HOOCCOOH).

The formula of the compounds of formula (III) corresponds to formula (II), in which:
  m and m' on the one hand, and p and p' on the other hand, are equal, and,
  A and A' on the one hand, and B and B' on the other hand, represent the same atom or group.

In this embodiment, the compounds of formula (III) are symmetrical. The compounds of formula (III) above (apart from the above two compounds) are novel.

The novel compounds defined above can be used according to the present invention.

According to an advantageous embodiment, the invention relates to compounds of the following formula (III'):

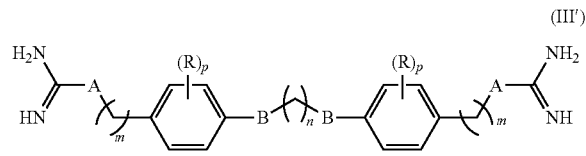

(III')

in which:

B, R, n, p are as defined above, and
  A represents an NH group or an NR" group, in which R" is a linear or branched alkyl group with 1 to 3 carbon atoms, and
  m represents an integer from 2 to 8, or a physiologically acceptable acid salt derived from a compound of formula (III') such as a hydrochloride, a formate, a trifluoroacetate or an oxalate (HOOCCOOH).

The formula of the compounds of formula (III') corresponds to formula (II'), in which:
  m and m' on the one hand, and p and p' on the other hand, are equal, and,
  A and A' on the one hand, and B and B' on the other hand, represent the same atom or group.

The formula of the compounds (III') corresponds to formula (III), in which A and A' represent, independently of one another, an NH group or an NR" group.

The novel compounds defined above can be used according to the present invention.

According to an advantageous embodiment, the invention relates to compounds of the following formula (IV):

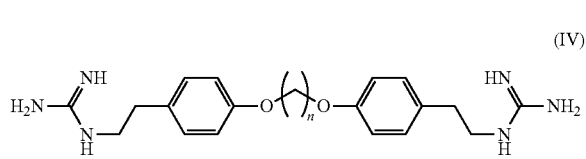

(IV)

in which n represents 1, 2, 3, 4, 5, 6, 7, 8, 9, 10, 11 or 12,
or a physiologically acceptable acid salt derived from a compound of formula (IV) such as a hydrochloride, a formate, a trifluoroacetate or an oxalate (HOOCCOOH).

The formula of the compounds of formula (IV) corresponds to formula (III), in which A represents an NH group, B represents an oxygen atom, p is equal to 0 and m is equal to 2. In this embodiment, the compounds of formula (IV) are symmetrical. The compounds of formula (IV) above (apart from the above two compounds) are novel.

The novel compounds defined above can be used according to the present invention.

According to an advantageous embodiment, the invention relates to compounds of the following formula 6:

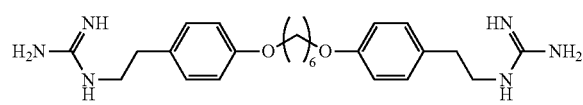

or a physiologically acceptable acid salt derived from a compound of formula 6 such as a hydrochloride, a formate, a trifluoroacetate or an oxalate (HOOCCOOH).

The formula of the compounds of formula 6 corresponds to formula (IV), in which n is equal to 6. In this embodiment, the compound of formula 6 is symmetrical. The compound of formula 6 above is novel.

The novel compounds defined above can be used according to the present invention.

According to an advantageous embodiment, the invention relates to compounds of formula (II) as defined above, in which:
m is different from m', and/or
p is different from p', and/or
R is different from R', and/or
A is different from A', and/or
B is different from B'.

In this embodiment, the compounds having such a formula are not symmetrical. The compounds of formula (II) with the characteristics defined above are novel.

The novel compounds defined above can be used according to the present invention.

According to another aspect, the invention relates to a pharmaceutical composition comprising, as active ingredient, at least one compound as defined above, in combination with a pharmaceutically acceptable vehicle.

In a particular embodiment, the pharmaceutical composition comprises as active ingredient:
a compound as defined above, for which the sum m+m'+n is less than or equal to 10, or
a compound as defined, for which the sum 2 m+n is less than or equal to 10,
said pharmaceutical composition being formulated in aqueous solution.

The first case (sum m+m'+n) corresponds to the compounds of formulae (VI), (I) and (II). The second case (sum 2 m+n) corresponds to the compounds of formulae (III), (IV) and 6, for which m is equal to m'. These compounds are soluble in aqueous solution.

In another particular embodiment, the pharmaceutical composition comprises as active ingredient:
a compound as defined above, in particular for which the sum m+m'+n is greater than 10, or
a compound as defined above, for which the sum 2 m+n is greater than 10, said pharmaceutical composition being formulated in aqueous-alcoholic solution.

The first case (sum m+m'+n) corresponds to the compounds of formulae (VI), (I) and (II). The second case (sum 2 m+n) corresponds to the compounds of formulae (III), (IV) and 6, for which m is equal to m'. When these sums are greater than 10, the compounds are rich in carbon, and therefore poorly soluble in water and more lipophilic.

By the expression "aqueous-alcoholic solution" is meant a mixture of water and of at least one alcohol, in particular selected from ethanol, isopropyl alcohol and benzyl alcohol.

In a particular embodiment of the invention, the pharmaceutical composition as defined above can be administered by the oral route, and in said pharmaceutical composition, the active ingredient is at a concentration from about 0.1 to about 5 mg/kg of body weight.

In another advantageous embodiment, the pharmaceutical composition as defined above can be administered topically, and in said pharmaceutical composition, the active ingredient is at a concentration from about 0.1% to about 1% relative to the total weight in the pharmaceutical composition.

By the expression "topical route" is meant that the pharmaceutical composition is applied at localized places, for example the skin or a mucous membrane.

Various formulations are possible for said pharmaceutical compositions: in the form of capsule, tablet, powder, cream, lotion, aqueous or aqueous-alcoholic solution, collutory, collyrium, milk, mousse, gel, spray or powder for example.

The invention also relates to the method of preparation of a compound of formula (Ia) comprising the following stages:
a) a stage of cleavage of the protecting groups Y of a compound of the following formula (X'):

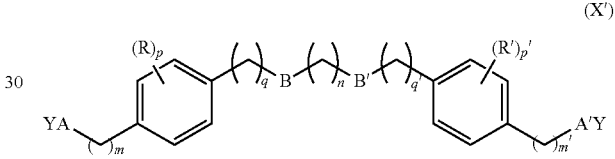

in which:
n represents an integer from 1 to 12, in particular from 1 to 8,
m and m' represent, independently of one another, integers from 2 to 8,
q and q' represent, independently of one another, integers from 0 to 2,
p and p' represent, independently of one another, integers from 0 to 4,
A and A' represent, independently of one another, an NH group or an NR" group, in which R" is a linear or branched alkyl group with 1 to 3 carbon atoms,
B and B' represent, independently of one another, an oxygen atom or a $CH_2$ group,
R and R' represent, independently of one another, a halogen, such as chlorine, bromine, iodine or fluorine atoms, or a linear or branched alkyl group with 1 to 3 carbon atoms,
Y represents a group protecting the amines, in particular Boc or Fmoc.
to obtain:
a compound of the following formula (XI'):

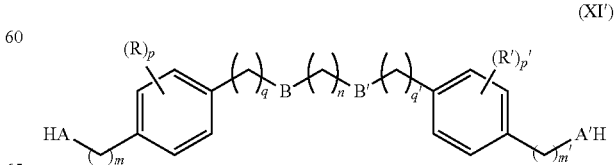

in which:

n represents an integer from 1 to 12, in particular from 1 to 8, m and m' represent, independently of one another, integers from 2 to 8, q and q' represent, independently of one another, integers from 0 to 2, p and p' represent, independently of one another, integers from 0 to 4, A and A' represent, independently of one another, an NH group or an NR" group, in which R" is a linear or branched alkyl group with 1 to 3 carbon atoms, B and B' represent, independently of one another, an oxygen atom or a $CH_2$ group, R and R' represent, independently of one another, a halogen, such as chlorine, bromine, iodine or fluorine atoms, or a linear or branched alkyl group with 1 to 3 carbon atoms, or, an acid salt derived from a compound of formula (XI') such as a hydrochloride, a formate, a trifluoroacetate or an oxalate (HOOCCOOH).

b) a stage of reaction of the compound of formula (XI') formed during stage a) with a compound of the following formula (XII):

in which GP represents a Leaving Group such as —SR, —NTf or

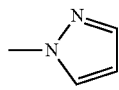

and Y represents a group protecting the amines, in particular Boc or Fmoc, to obtain a compound of the following formula (XIII'):

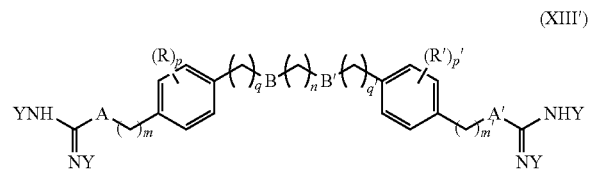

in which:

n represents an integer from 1 to 12, in particular from 1 to 8, m and m' represent, independently of one another, integers from 2 to 8, q and q' represent, independently of one another, integers from 0 to 2, p and p' represent, independently of one another, integers from 0 to 4, A and A' represent, independently of one another, an NH group or an NR" group, in which R" is a linear or branched alkyl group with 1 to 3 carbon atoms, B and B' represent, independently of one another, an oxygen atom or a $CH_2$ group, R and R' represent, independently of one another, a halogen, such as chlorine, bromine, iodine or fluorine atoms, or a linear or branched alkyl group with 1 to 3 carbon atoms, Y represents a group protecting the amines, in particular Boc or Fmoc.

c) a stage of deprotection of the amine functions of the compound of formula (XIII') obtained in stage b) to obtain:

a compound of the following formula (Ia):

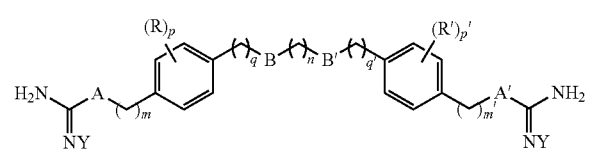

in which n:

n represents an integer from 1 to 12, in particular from 1 to 8, m and m' represent, independently of one another, integers from 2 to 8, q and q' represent, independently of one another, integers from 0 to 2, p and p' represent, independently of one another, integers from 0 to 4, A and A' represent, independently of one another, an NH group or an NR" group, in which R" is a linear or branched alkyl group with 1 to 3 carbon atoms, B and B' represent, independently of one another, an oxygen atom or a $CH_2$ group, R and R' are, independently of one another, a halogen, such as chlorine, bromine, iodine or fluorine atoms, or a linear or branched alkyl group with 1 to 3 carbon atoms, or an acid salt derived from a compound of formula (Ia) such as a hydrochloride, a formate, a trifluoroacetate or an oxalate (HOOCCOOH).

By "linear or branched alkyl group with 1 to 3 carbon atoms" is meant the methyl, ethyl, n-propyl and isopropyl groups.

Procedures for cleavage, or deprotection, of protecting groups of protected amine functions such as used in stages a) and c) are described in "Greene's Protective Groups in Organic Synthesis Peter G. M. Wuts, Theodora W. Greene, Wiley". The cleavage of boc groups can in particular be carried out in an acid medium, for example:

with hydrochloric acid in aqueous solution or in organic solvent (for example dioxane or ether) (in this case, the compound is obtained in the form of the hydrochloride), or, with trifluoroacetic acid, in particular in dichloromethane (in this case, the compound is obtained in the form of trifluoroacetate).

When these stages are carried out in an acid medium, the neutral form of the compound can be obtained by neutralizing the medium after reaction. However, the compounds can be isolated more easily when the compounds of formula (Ia), and in particular (XI'), are in the form of acid salts.

Stage b) makes it possible to form the guanidine function. This stage is generally carried out in the presence of a base, for example triethylamine or diisopropylethylamine, and in an organic solvent, such as dichloromethane, although the use of other organic solvents is also possible, for example THF, methanol, acetonitrile, dioxane, or a mixture of these solvents.

According to an advantageous embodiment, the method of preparation, as defined above, of a compound of formula (IV) comprises:

a) a stage of cleavage of the protecting groups Y of a compound of the following formula (XX):

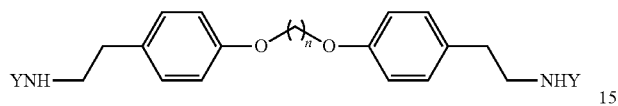

(XX)

in which n represents 1, 2, 3, 4, 5, 6, 7, 8, 9, 10, 11 or 12, and
Y represents a group protecting the amines, in particular Boc or Fmoc.
to obtain:
a compound of the following formula (XXI):

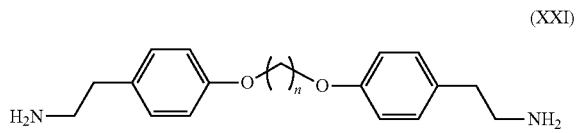

(XXI)

in which n represents 1, 2, 3, 4, 5, 6, 7, 8, 9, 10, 11 or 12, or, an acid salt derived from a compound of formula (XXI) such as a hydrochloride, a formate, a trifluoroacetate or an oxalate (HOOCCOOH), b) a stage of reaction of the compound of formula (XXI) formed during stage a) with a compound of the following formula (XII):

(XII)

in which GP represents a leaving group such as —SR, —NTf or

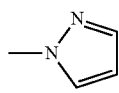

and Y represents a group protecting the amines, in particular Boc or Fmoc,
to obtain a compound of the following formula (XXII):

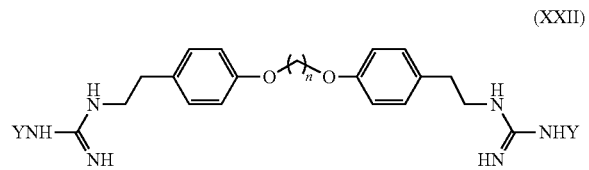

(XXII)

in which n represents 1, 2, 3, 4, 5, 6, 7, 8, 9, 10, 11 or 12, and
Y represents a group protecting the amines, in particular Boc or Fmoc.

c) a stage of deprotection of the amine functions of the compound of formula (XXII) obtained in stage b) to obtain:
a compound of the following formula (IV):

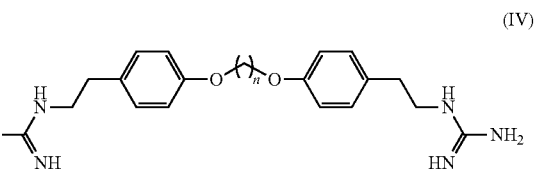

(IV)

in which n represents 1, 2, 3, 4, 5, 6, 7, 8, 9, 10, 11 or 12, or,
an acid salt derived from a compound of formula (IV) such as a hydrochloride, a formate, a trifluoroacetate or an oxalate (HOOCCOOH).

The procedures for stages a), b) and c) and their characteristics are as described above for preparing the compounds of formula (Ia).

According to another aspect, the invention relates to the compound of the following formula (X'):

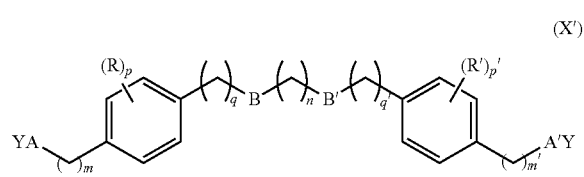

(X')

in which:
n represents an integer from 1 to 12, in particular from 1 to 8,
m and m' represent, independently of one another, integers from 2 to 8,
q and q' represent, independently of one another, integers from 0 to 2,
p and p' represent, independently of one another, integers from 0 to 4,
A and A' represent, independently of one another, an NH group or an NR" group, in which R" is a linear or branched alkyl group with 1 to 3 carbon atoms,
B and B' represent, independently of one another, an oxygen atom or a CH$_2$ group,
R and R' represent, independently of one another, a halogen, such as chlorine, bromine, iodine or fluorine atoms, or a linear or branched alkyl group with 1 to 3 carbon atoms,
Y represents a group protecting the amines, in particular Boc or Fmoc.
in particular a compound of the following formula (XX):

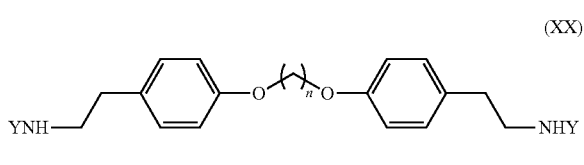

(XX)

in which n represents 1, 2, 3, 4, 5, 6, 7, 8, 9, 10, 11 or 12, and
Y represents a group protecting the amines, in particular Boc or Fmoc.

By "Linear or branched alkyl group with 1 to 3 carbon atoms" is meant the methyl, ethyl, n-propyl and isopropyl groups.

The compounds of formula (X') and (XX) are novel.

According to one embodiment of the invention, the compound of formula (X') as defined above is an intermediate for preparing the compounds of formula (I) as defined above, and the compound of formula (XX) as defined above is an intermediate for preparing the compounds of formula (IV) as defined above.

The invention also relates to the method of preparation of a compound of formula (Ic), corresponding to formula (I) in which B=O, comprising:

a) a stage of reaction between a compound of the following formula (XXX):

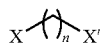

(XXX)

in which:

X and X' represent, independently of one another, a halogen, in particular a chlorine, a bromine or an iodine, n represents an integer from 1 to 12, in particular from 1 to 8, with a compound of the following formula (XXXI):

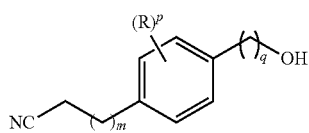

(XXXI)

in which:

m represents an integer from 1 to 8, q represents an integer from 0 to 2, p represents an integer from 0 to 4, R represents a halogen, such as chlorine, bromine, iodine or fluorine atoms, or a linear or branched alkyl group with 1 to 3 carbon atoms, b) followed by a stage of reaction with a compound of the following formula (XXXII):

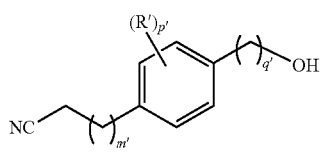

(XXXII)

in which:

m' represents an integer from 1 to 8, q' represents an integer from 0 to 2, p' represents an integer from 0 to 4, R' represents a halogen, such as chlorine, bromine, iodine or fluorine atoms, or a linear or branched alkyl group with 1 to 3 carbon atoms, it being possible for stages a) and b) to be carried out simultaneously ("one pot" reaction) or successively, to obtain the compound of the following formula (XXXIII):

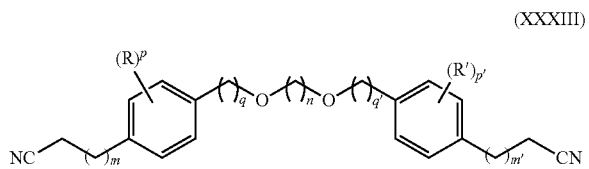

(XXXIII)

in which.

n represents an integer from 1 to 12, in particular from 1 to 8, m and m' represent, independently of one another, integers from 1 to 8, q and q' represent, independently of one another, integers from 0 to 2, p and p' represent, independently of one another, integers from 0 to 4, R and R' are, independently of one another, a halogen, such as chlorine, bromine, iodine or fluorine atoms, or a linear or branched alkyl group with 1 to 3 carbon atoms, c) followed by a stage of Pinner reaction, to form a compound of the following formula (Ic):

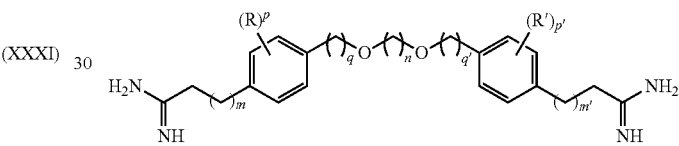

(Ic)

in which:

n represents an integer from 1 to 12, in particular from 1 to 8, m and m' represent, independently of one another, integers from 1 to 8, q and q' represent, independently of one another, integers from 0 to 2, p and p' represent, independently of one another, integers from 0 to 4, R and R' are, independently of one another, a halogen, such as chlorine, bromine, iodine or fluorine atoms, or a linear or branched alkyl group with 1 to 3 carbon atoms, or a physiologically acceptable acid salt derived from a compound of formula (Ic) such as a hydrochloride, a formate, a trifluoroacetate or an oxalate (HOOCCOOH).

Stages a) and b) in particular take place in a basic medium.

The Pinner reaction comprises two stages: a reaction of the nitrile function with ethanol in the presence of an acid, in particular hydrochloric acid, followed by a reaction with ammonia, leading to formation of the amidine function.

The invention also relates to the method of preparation of a compound of formula (Id) corresponding to formula (I) in which B=CH$_2$, comprising:

a) a stage of alkylation of a compound of the following formula (XXXIV):

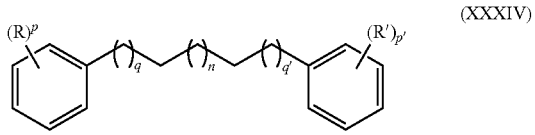

(XXXIV)

in which:

n represents an integer from 1 to 12, in particular from 1 to 8, q and q' represent, independently of one another, integers from 0 to 2, p and p' represent, independently of one another, integers from 0 to 4, R and R' are, independently of one another, a halogen, such as chlorine, bromine, iodine or fluorine atoms, or a linear or branched alkyl group with 1 to 3 carbon atoms, to obtain a compound of the following formula (XXXV):

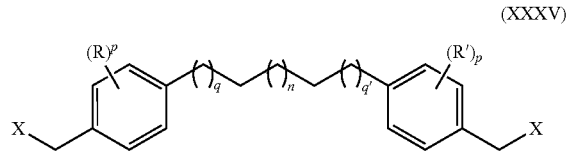

(XXXV)

in which:

n represents an integer from 1 to 12, in particular from 1 to 8, q and q' represent, independently of one another, integers from 0 to 2, p and p' represent, independently of one another, integers from 0 to 4, R and R' are, independently of one another, a halogen, such as chlorine, bromine, iodine or fluorine atoms, or a linear or branched alkyl group with 1 to 3 carbon atoms, X represents a leaving group, in particular a halogen atom such as the chlorine, bromine, and iodine atoms b) followed by one or more stages of homologation to obtain the compound of the following formula (XXXVI):

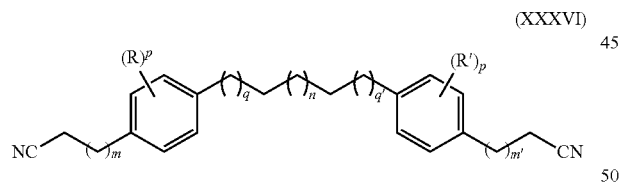

(XXXVI)

in which:

n represents an integer from 1 to 12, in particular from 1 to 8, m and m' represent, independently of one another, integers from 1 to 8, q and q' represent, independently of one another, integers from 0 to 2, p and p' represent, independently of one another, integers from 0 to 4, R and R' are, independently of one another, a halogen, such as chlorine, bromine, iodine or fluorine atoms, or a linear or branched alkyl group with 1 to 3 carbon atoms, c) followed by a stage of Pinner reaction, to form a compound of the following formula (Id):

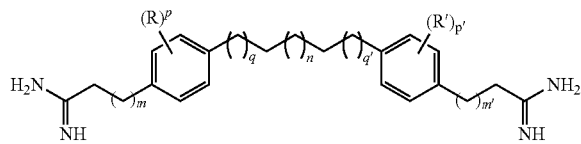

(Id)

in which:

n represents an integer from 1 to 12, in particular from 1 to 8, m and m' represent, independently of one another, integers from 1 to 8, q and q' represent, independently of one another, integers from 0 to 2, p and p' represent, independently of one another, integers from 0 to 4, R and R' are, independently of one another, a halogen, such as chlorine, bromine, iodine or fluorine atoms, or a linear or branched alkyl group with 1 to 3 carbon atoms, or a physiologically acceptable acid salt derived from a compound of formula (Id) such as a hydrochloride, a formate, a trifluoroacetate or an oxalate (HOOCCOOH).

EXAMPLES

A. Synthesis of the Compounds Used as Active Ingredients

Example 1

Synthesis of 1,6-bis(4-(2-Boc-aminoethyl)phenoxy)hexane a) Synthesis of N-(t-butoxycarbonyl)-2-(4-hydroxyphenyl)-ethylamine

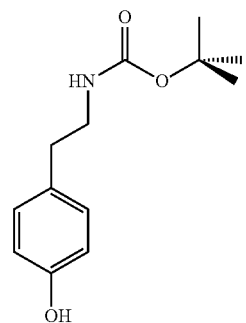

Tyramine hydrochloride (1.0 g; 5.76 mmol; 1 eq.) is dissolved in a mixture of dioxane and distilled $H_2O$ (25/12 mL), then a solution of NaOH (0.46 g; 11.5 mmol) in 10 mL of distilled water is added. The whole is stirred for 10 min before adding di-tert-butyl-bicarbonate ($Boc_2O$) (1.26 g; 5.76 mmol; 2 eq.). The reaction is stirred overnight, under argon and at ambient temperature. After evaporation of the dioxane, 40 mL of EtOAc is added to the residual aqueous phase, and the pH of the mixture is lowered to 7-8 with 1M aqueous solution of HCl. The phases are then separated and the aqueous phase is washed with EtOAc (2* 15 mL). The combined organic phases are then dried over $Na_2SO_4$, filtered and evaporated. The crude product is then purified in a chromatographic column ($Al_2O_3$, $CH_2Cl_2$/Hex, 85:15) to give N-(t-butoxycarbonyl)-2-(4-hydroxyphenyl)-ethylamine (0.98 g; 73%).

M.p.: 61-62° C.
IR (KBr): 3378.9 (—OH; —CONH—) 1686.6 (CO).
UV-Vis ($CH_2Cl_2$): 277 (1803).
$^1$H-NMR (400 MHz, $CDCl_3$): 1.441 (s, 9 H, tert); 2.703 (t, J=7.9 Hz; 2 H, $CH_2CH_2N$); 3.329 (m, 2 H, $CH_2CH_2N$); 4.602 (broad s, 1 H, NH or OH); 6.023 (broad s, 1 H, NH or OH); 6.774 (d, J=8.3 Hz; 2 H; ArH); 7.013 (d, J=8.3 Hz; 2 H; ArH).
$^{13}$C-NMR (100 MHz, $CDCl_3$): 28.84 ($CMe_3$); 35.64 ($CH_2CH_2N$); 42.49 ($CH_2CH_2N$); 80.15 ($CMe_3$); 115.97 ($C_m$); 130.18 ($C_o$); 130.50 ($C_p$); 155.38 ($C_{ipso}$); 156.84 (CO).

Elementary analysis calculated for $C_{13}H_{19}O_3N$ (237.29): C: 65.80%; H: 8.07%; N: 5.90%; found: C: 65.77%; H: 8.09%; N: 5.90%.
IE MS: 181 [M–$(Me)_3$CO–H+Na]$^+$; 107 [M–$(Me)_3$COC(O)$NHCH_2$]

b) Synthesis of 1,6-bis(4-(2-boc-aminoethyl)phenoxy)hexane $^1$H-NMR (400 MHz, $CDCl_3$): 1.43 (s, 18 H, tert); 1.54 (m, 4 H, $OCH_2CH_2CH_2$); 1.81 (t, J=6.0 Hz, 4 H, $OCH_2CH_2CH_2$); 2.73 (t, J=6.6 Hz, 4 H, $CH_2CH_2N$); 3.34 (m, 4 H, $CH_2CH_2N$); 3.95 (t, J=6.5 Hz, 4 H, $OCH_2CH_2CH_2$); 4.51 (broad s, 2 H, NH); 6.84 (d, J=8.6 Hz, 4 H, ArH); 7.09 (d, J=8.6 Hz, 4 H, ArH).

$^{13}$C-NMR (100 MHz, $CDCl_3$): 26.27 ($OCH_2CH_2CH_2$); 28.80 ($CMe_3$); 29.65 ($OCH_2CH_2CH_2$); 35.71 ($CH_2CH_2N$); 38.57 ($CH_2CH_2N$); 68.31 ($OCH_2CH_2CH_2$); 76.62 ($CMe_3$); 115.07 ($C_o$ or $C_m$); 130.06 ($C_o$ or $C_m$); 131.28 ($C_p$); 156.26 ($C_{ipso}$); 158.18 ($C_{gua}$).

Elementary analysis calculated for $C_{32}H_{48}O_6N_2$ (556.73): C: 69.03%; H: 8.68%; N: 5.03%; found: C: 68.98%; H: 8.57%; N: 5.07%.

MS (ES): 557.31 [M+H$^+$]$^+$.

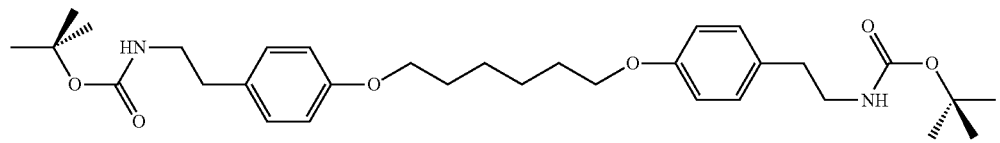

N-(t-butoxycarbonyl)-2-(4-hydroxyphenyl)-ethylamine (1.5 g; 6.32 mmol; 1 eq.) is dissolved in $CH_3CN$ (freshly distilled on $CaH_2$) and $K_2CO_3$ is added (1.74 g; 12.64 mmol; 2 eq.). The mixture is heated under reflux under argon for about two hours before adding dichlorohexane (0.55 mL; 3.79 mmol; 0.6 eq.). After 24 hours under reflux, 0.3 equivalent of dichlorohexane is added. After reaction for 48 H, return to ambient temperature is followed by evaporation of the solvent. The crude product obtained is dissolved in $CH_2Cl_2$ and filtered on a glass frit to remove mineral impurities. The filtrate is then concentrated to a minimum of solvent and is subjected to precipitation by adding MeOH accompanied by cold evaporation. The solid obtained is then filtered, rinsed with MeOH and dried under vacuum. It corresponds to the expected compound in the form of a white powder (0.52 g; 30%).

A variant using DMF or another amide (dimethylacetamide, N-methylpyrrolidone for example) as solvent can be used at ambient temperature.

M.p.: 135-136° C.
IR (KBr): 3367.7 (CONH); 1683.4 (HNCO); 1511.3 (NH).
UV-Vis ($CH_2Cl_2$): 230 (22884.6); 278 (5802.7).

Example 2

Synthesis of 1,6-bis(4-(2-guanidinoethyl)phenoxy)hexane 6 a) Synthesis of 1,6-bis(4-(2-aminoethyl)phenoxy)hexane

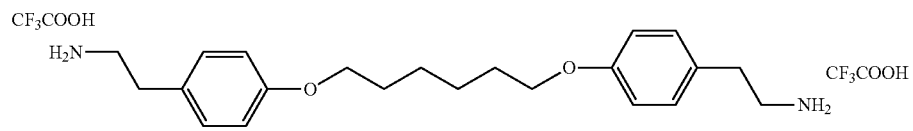 [SMILES: "CF3COOH" ; NCCc1ccc(OCCCCCCOc2ccc(CCN)cc2)cc1 ; "CF3COOH"]

1,6-bis(4-(2-boc-aminoethyl)phenoxy)hexane (0.5 g; 0.98 mmol) is dissolved in anhydrous $CH_2Cl_2$ (40 mL) and TFA is added (5 mL). The reaction mixture is stirred under an inert atmosphere for about 3.5h. The mixture is then concentrated to give a translucent oil, which is taken up in dichloromethane several times and concentrated in order to remove the maximum amount of the residual TFA. The product obtained is then triturated in $Et_2O$ to give a white solid, which is then filtered, washed with $Et_2O$ and dried under vacuum. It is the sought compound in the form of bis(trifluoroacetate) in the form of a white powder (0.5 g; 88%).

M.p.: 162-163° C.

IR (KBr): 2956.5 ($NH_3^+$); 1676.7 ($NH_3^+$).

UV-Vis ($H_2O$): 195 (9326.7); 221 (2238.7).

$^1$H-NMR (400 MHz, DMSO-$D_6$): 1.46 (m, 4 H, $OCH_2CH_2CH_2$); 1.72 (m, 4 H, $OCH_2CH_2CH_2$); 2.77 (t, J=8.4 Hz, 4 H, $CH_2CH_2N$); 2.98 (m, 4 H, $CH_2CH_2N$); 3.94 (t, J=6.3 Hz, 4 H, $OCH_2CH_2CH_2$); 6.88 (d, J=8.5 Hz, 4 H, ArH); 7.15 (d, J=8.5 Hz, 4 H, 7.78 (broad s, 4 H, $NH_2$).

$^{13}$C-NMR (100 MHz, DMSO-$D_6$): 25.68 ($OCH_2CH_2CH_2$); 29.04 ($OCH_2CH_2CH_2$); 32.56 ($CH_2CH_2N$); 40.59 ($CH_2CH_2N$); 67.79 ($OCH_2CH_2CH_2$); 115.00 ($C_o$ or $C_m$); 129.34 ($C_p$); 130.01 ($C_o$ or $C_m$); 157.95 ($C_{ipso}$).

Elementary analysis calculated for $C_{26}H_{34}O_6N_2F_6$, 0.5 $H_2O$ (593.44): C: 52.62%; H: 5.94%; N: 4.72%; found: C: 52.88%; H: 6.06%; N: 4.94%.

MS (ES$^+$): 357.34 [M−2 $CF_3COOH+H^+$]$^+$.

MS (ES$^+$): 696.98 [M+$CF_3COOH-H^+$]$^-$.

b) Synthesis of 1,6-bis(4-(2-(N,N'-di-Boc)guanidinoethyl)phenoxy)hexane

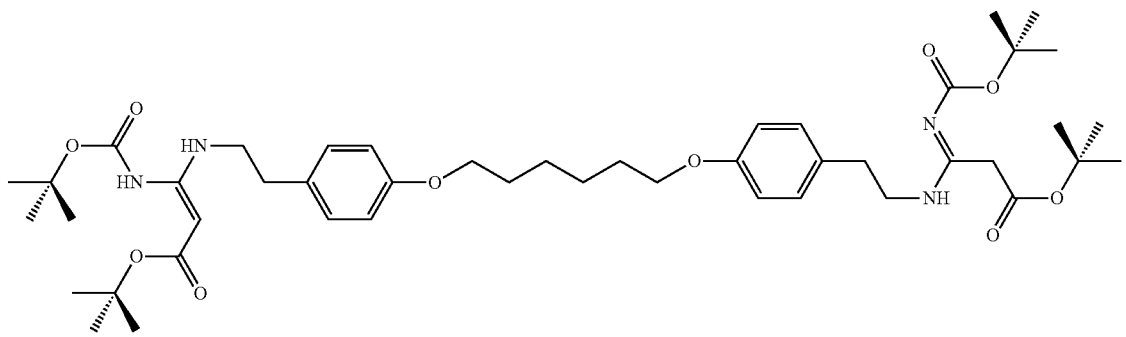

1,6-bis(4-(2-aminoethyl)phenoxy)hexane bis(trifluoroacetate) (0.3 g; 0.51 mmol; 1 eq.) is suspended in 20 mL of anhydrous $CH_2Cl_2$ and solubilized by adding a minimum of MeOH. Triethylamine $Et_3N$ (0.43 mL; 3.07 mmol; 6 eq.) is then added, as well as N,N'-bis(tert-butoxycarbonyl)-N"-triflylguanidine (0.4 g; 1.02 mmol; 2 eq.) and the mixture is placed, at ambient temperature, under an inert atmosphere with stirring for 3 h. The solvent is then removed by evaporation under vacuum. The crude product obtained is solubilized with 30 mL of $CH_2Cl_2$, washed with a 2M aqueous solution of $NaHSO_4$, then with a saturated aqueous solution of $NaHCO_3$. The organic phase is then dried over $Na_2SO_4$, filtered, concentrated and dried under vacuum to give the expected compound in the form of a white powder (0.43 g; 100%).

M.p.: 105-106° C.

IR (KBr): 3341.7 (CONH); 1725.6 (NHCO); 1572.0 (NH).

$^1$H-NMR (400 MHz, CDCl$_3$): 1.47 (s, 18 H, tert); 1.50 (s, 18 H, tert); 1.52 (m, 4 H, $OCH_2CH_2CH_2$); 1.80 (t, J=6.5 Hz, 4 H, $OCH_2CH_2CH_2$); 2.80 (t, J=7.3 Hz, $CH_2CH_2N$); 3.62 (q, J=7.3 Hz, 4 H, $CH_2CH_2N$); 3.94 (t, J=6.4 Hz, 4 H, $OCH_2CH_2CH_2$); 6.82 (d, J=8.5 Hz, 4 H, ArH); 7.11 (d, J=8.5 Hz, 4 H, ArH); 8.35 (m, 2 H, $CH_2CH_2NH$); 11.46 (broad s, 2 H, NH).

$^{13}$C-NMR (100 MHz, CDCl$_3$): 26.29 ($OCH_2CH_2CH_2$); 22.44 ($CMe_3$); 28.71 ($CMe_3$); 29.66 ($OCH_2CH_2CH_2$); 34.82 ($CH_2CH_2N$); 42.85 ($CH_2CH_2N$); 68.30 ($OCH_2CH_2CH_2$); 79.53 ($CMe_3$); 83.33 ($CMe_3$); 115.07 ($C_o$ or $C_m$); 130.08 ($C_o$ or $C_m$); 130.89 ($C_r$); 153.57, 156.51, 158.23, 164.03 (CO, $C_{ipso}$ and $C_{gua}$).

Elementary analysis calculated for $C_{44}H_{68}O_{10}N_6$ (841.05): C: 62.83%; H: 8.14%; N: 9.99%; found: C: 61.26%; H: 7.84%; N: 9.99%.

MS (ES): 841.11 [M+H$^+$]$^+$.

c) Synthesis of 1,6-bis(4-(2-guanidinoethyl)phenoxy)hexane 6

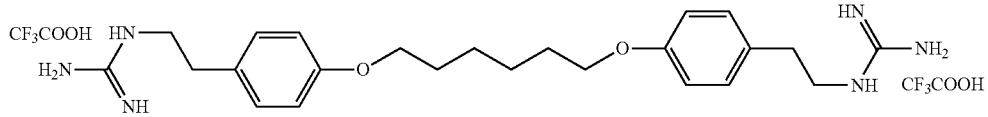 [SMILES: "CF3COOH" ; N=C(N)NCCc1ccc(OCCCCCCOc2ccc(CCNC(=N)N)cc2)cc1 ; "CF3COOH"]

The compound 1,6-bis(4-(2-(N,N'-di-Boc)guanidinoethyl)phenoxy)hexane (0.45 g; 0.53 mmol) is dissolved in anhydrous $CH_2Cl_2$ (30 mL) and TFA is added (3 mL). The reaction mixture is stirred under an inert atmosphere for about 3 h. The mixture is then concentrated to give a translucent oil, which is taken up in dichloromethane several times and concentrated to remove the maximum amount of the residual TFA. The product obtained is then triturated in $Et_2O$ to give a white solid, which is then filtered, washed with $Et_2O$ and dried under vacuum. It is the sought compound 1,6-bis(4-(2-guanidinoethyl)phenoxy)hexane bis(trifluoroacetate) in the form of a white powder (0.28 g; 79%).

M.p.: 99-100° C.

IR (KBr): 2941.0 ($NH_3^+$); 1669.7 ($NH_3^+$).

UV-Vis ($H_2O$): 196 (81810.5); 223 (19784.3).

$^1$H-NMR (400 MHz, $D_2O$): 1.5 (m, 4 H, $OCH_2CH_2CH_2$); 1.78 (m, 4 H, $OCH_2CH_2CH_2$); 2.80 (t, J=6.8 Hz, $CH_2CH_2N$); 3.42 (t, J=6.7 Hz, 4 H, $CH_2CH_2N$); 3.94 (t, J=6.4 Hz, 4 H, $OCH_2CH_2CH_2$); 6.97 (d, J=8.3 Hz, 4 H, ArH); 7.23 (d, J=8.3 Hz, 4 H, ArH).

$^1$H-NMR (400 MHz, DMSO-$D_6$): 1.47 (m, 4 H, $OCH_2CH_2CH_2$); 1.70 (m, 4 H, $OCH_2CH_2CH_2$); 2.70 (t, J=7.3 Hz, $CH_2CH_2N$); 3.32 (m, 4 H, $CH_2CH_2N$); 3.9 (t, J=6.4 Hz, 4 H, $OCH_2CH_2CH_2$); 6.86 (d, J=8.5 Hz, 4 H, ArH); 7.16 (d, J=8.5 Hz, 4 H, ArH).

$^{13}$C-NMR (100 MHz, DMSO-$D_6$): 25.70 ($OCH_2CH_2CH_2$); 27.93 ($OCH_2CH_2CH_2$); 33.94 ($CH_2CH_2N$); 42.64 ($CH_2CH_2N$); 67.76 ($OCH_2CH_2CH_2$); 114.77 ($C_o$ or $C_m$); 130.09 ($C_o$ or $C_m$); 130.39 ($C_p$); 157.24, 157.74 ($C_{ipso}$ and $C_{gua}$).

Elementary analysis calculated for $C_{28}H_{38}O_6N_6F_6$, 0.5 $H_2O$ (677.63): C: 49.63%; H: 5.80%; N: 12.40%; found: C: 50.09%; H: 5.50%; N: 11.81%.

MS (ES$^+$): 555.17 [M–$CF_3COOH+H^+$]$^+$; 442.31 [M–2 $CF_3COOH+2H^+$]$^+$.

MS (ES$^-$): 780.93 [M+$CF_3COOH–2H^+$]$^-$; 667.07 [M–H$^+$]$^-$.

Example 3

Synthesis of 1,6-bis(4-(2-guanidinoethyl)phenoxy)alkanes

The following compounds:
1,1-bis(4-(2-guanidinoethyl)phenoxy)methane,
1,3-bis(4-(2-guanidinoethyl)phenoxy)propane,
1,4-bis(4-(2-guanidinoethyl)phenoxy)butane,
1,5-bis(4-(2-guanidinoethyl)phenoxy)pentane,
1,7-bis(4-(2-guanidinoethyl)phenoxy)heptane,
1,8-bis(4-(2-guanidinoethyl)phenoxy)octane,
1,9-bis(4-(2-guanidinoethyl)phenoxy)nonane,
1,10-bis(4-(2-guanidinoethyl)phenoxy)decane,
1,12-bis(4-(2-guanidinoethyl)phenoxy)dodecane
are prepared following the protocols described above to arrive at 1,6-bis(4-(2-guanidinoethyl)phenoxy)hexane (using respectively diiodomethane, dibromopropane, dibromobutane, dibromopentane, dibromoheptane, dibromooctane, dibromononane, dibromodecane and dibromododecane in the place of dichlorohexane), or the corresponding dichloro-, dibromo-, diiodo- or di-para-toluene sulphonyl alkanes.

The characteristics of these compounds are described below.

1,1-bis(4-(2-guanidinoethyl)phenoxy) methane=compound 1

$^1$H-NMR (400 MHz, $D_2O$): 2.81 (t, J=6.54 Hz, 4 H, $ArCH_2CH_2N$); 3.39 (t, J=6.54 Hz, 4 H, $ArCH_2CH_2N$); 5.76 (s, 2 H, $ArCH_2O$); 7.05 (d, J=8.32 Hz, 4 H, ArH); 7.21 (d, J=8.28 Hz, 4 H, ArH).

Elementary analysis calculated for $C_{19}H_{26}N_6O_2$, 2 $CF_3COOH$ (598.5): C, 46.16, H, 4.72, N, 14.04; found: C, 45.95; H, 4.46; N, 13.69.

1,3-bis(4-(2-guanidinoethyl)phenoxy) propane=compound 3

$^1$H-NMR (400 MHz, $D_2O$): 2.12 (t, J=6.0 Hz, 2 H, $CH_2CH_2CH_2$); 2.73 (t, J=6.8 Hz, 4 H, $ArCH_2CH_2N$); 3.32 (t, J=6.8 Hz, 4 H, $CH_2CH_2N$); 4.14 (t, J=6.0 Hz, 4 H, $ArOCH_2CH_2$); 6.89 (d, J=8.5 Hz, 4 H, ArH); 7.13 (d, J=8.5 Hz, 4 H, ArH).

Elementary analysis calculated for $C_{25}H_{32}O_6N_6F_6$, 1/2 $H_2O$ (635.55): C, 47.24, H, 5.23, N, 13.22; found: C, 47.20; H, 5.57, N, 13.52.

1,4-bis(4-(2-guanidinoethyl)phenoxy) butane=compound 4

$^1$H-NMR (400 MHz, $D_2O$): 1.83 (broad t, 4 H, $CH_2CH_2CH_2CH_2$); 2.74 (t, J=6.55 Hz, 4 H, $ArCH_2CH_2N$); 3.32 (t, J=6.8 Hz, 4 H, $ArCH_2CH_2N$); 4.04 (broad t, 4 H, $ArOCH_2$); 6.87 (d, J=8.3 Hz, 4 H, ArH); 7.14 (d, J=8.3 Hz, 4 H, ArH).

Elementary analysis calculated for $C_{26}H_{34}O_6N_6F_6$, $H_2O$ (658.59): C, 47.42; H, 5.51; N, 12.76; found: C, 46.98; H, 5.74, N, 13.37.

1,5-bis(4-(2-guanidinoethyl)phenoxy) pentane=compound 5

$^1$H-NMR (400 MHz, $D_2O$): 1.50 (quint, J=6.55 Hz, 2 H, $CH_2CH_2CH_2CH_2CH_2$); 1.72 (quint, J=7.0, 4 H, $CH_2CH_2CH_2CH_2CH_2$); 2.73 (t, J=6.55 Hz, 4 H, $ArCH_2CH_2N$); 3.32 (t, J=6.8 Hz, 4 H, $ArCH_2CH_2N$); 3.98 (t, J=6.55, 4 H, $ArOCH_2$); 6.87 (d, J=8.3 Hz, 4 H, ArH); 7.13 (d, J=8.3 Hz, 4 H, ArH).

Elementary analysis calculated for $C_{27}H_{36}O_6N_6F_6$, $H_2O$ (672.27): C, 48.21; H, 5.69; N, 12.49; found: C, 48.57; H, 5.77, N, 12.23.

1,7-bis(4-(2-guanidinoethyl)phenoxy) heptane=compound 7

$^1$H-NMR (400 MHz, $D_2O$): 1.42 (m, 6 H, $OCH_2CH_2CH_2$); 1.72 (m, 4 H, $OCH_2CH_2CH_2$); 2.81 (t, J=6.66 Hz, 4 H,

ArCH$_2$CH$_2$N); 3.39 (t, J=6.68 Hz, 4 H, ArCH$_2$CH$_2$N); 4.02 (t, J=6.42 Hz, 4 H, ArOCH$_2$CH$_2$); 6.94 (d, J=8.32 Hz, 4 H, ArH); 7.21 (d, J=8.56 Hz, 4 H, ArH)

Elemental analyses calculated for C$_{25}$H$_{38}$N$_6$O$_2$, 2 CF$_3$COOH (682.65): C: 51.02%; H: 5.91%; N: 12.31% found: C: 50.72%; H: 5.96%; N: 12.24%.

1,8-bis(4-(2-guanidinoethyl)phenoxy) octane=compound 8

$^1$H-NMR (400 MHz, D$_2$O): 1.27 (m, 4 H, CH$_2$CH$_2$CH$_2$CH$_2$CH$_2$CH$_2$CH$_2$CH$_2$); 1.34 (m, 4 H, CH$_2$CH$_2$CH$_2$CH$_2$CH$_2$CH$_2$CH$_2$CH$_2$); 1.65, (quint, J=7.0, 4 H, CH$_2$CH$_2$CH$_2$CH$_2$CH$_2$CH$_2$CH$_2$CH$_2$); 2.73 (t, J=6.8 Hz, 4 H, ArCH$_2$CH$_2$N); 3.32 (t, J=6.8 Hz, 4 H, ArCH$_2$CH$_2$N); 3.96 (t, J=6.3, 4 H, ArOCH$_2$); 6.87 (d, J=8.6 Hz, 4 H, ArH); 7.13 (d, J=8.6 Hz, 4 H, ArH).

Elementary analysis calculated for C$_{30}$H$_{42}$O$_6$N$_6$F$_6$, 1/2H$_2$O (705.69): C, 51.06, H, 6.14, N, 11.91; found: C, 51.41; H, 6.40, N, 11.56.

1,9-bis(4-(2-guanidinoethyl)phenoxy) nonane=compound 9

$^1$H-NMR (400 MHz, DMSO-D$_6$): 1.32 (m, 6 H, OCH$_2$(CH$_2$)$_7$CH$_2$); 1.40 (m, 4 H, CH$_2$CH$_2$CH$_2$); 1.69 (m, 4 H, OCH$_2$CH$_2$CH$_2$); 2.71 (t, J=7.20 Hz, 4 H, ArCH$_2$CH$_2$N); 3.32 (m, 4 H, ArCH$_2$CH$_2$N); 3.92 (t, J=6.40 Hz, 4 H, OCH$_2$CH$_2$CH$_2$); 6.86 (d, J=8.80 Hz, 4 H, ArH); 7.16 (d, J=8.40 Hz, 4 H, ArH); 7.52 (m, 2 H, NH)

Elementary analysis calculated for C$_{27}$H$_{42}$N$_6$O$_2$, 2 CF$_3$COOH (710.71): C, 52.39, H, 6.24, N, 11.82; found: C, 52.07; H, 5.95; N, 11.62.

1,10-bis(4-(2-guanidinoethyl)phenoxy) decane=compound 10

$^1$H-NMR (400 MHz, D$_2$O): 1.21 (m, 8 H, CH$_2$CH$_2$CH$_2$CH$_2$CH$_2$CH$_2$CH$_2$CH$_2$CH$_2$CH$_2$); 1.32 (broad m, 4 H, CH$_2$CH$_2$CH$_2$CH$_2$CH$_2$CH$_2$CH$_2$CH$_2$CH$_2$CH$_2$); 1.64, (quint, J=7.0 Hz, 4 H, CH$_2$CH$_2$CH$_2$CH$_2$CH$_2$CH$_2$CH$_2$CH$_2$CH$_2$CH$_2$); 2.72 (t, J=6.55 Hz, 4 H, ArCH$_2$CH$_2$N); 3.31 (t, J=6.55 Hz, 4 H, ArCH$_2$CH$_2$N); 3.96 (t, J=6.54 Hz, 4 H, ArOCH$_2$); 6.87 (d, J=8.6 Hz, 4 H, ArH); 7.13 (d, J=8.6 Hz, 4 H, ArH).

Elementary analysis calculated for C$_{32}$H$_{46}$O$_6$N$_6$F$_6$ (724.73): C, 53.03; H, 6.40; N, 11.60; found: C, 53.29; H, 6.49; N, 11.66.

1,12-bis(4-(2-guanidinoethyl)phenoxy) dodecane=compound 12

$^1$H-NMR (400 MHz, D$_2$O): 1.26 (m, 12 H, CH$_2$CH$_2$CH$_2$CH$_2$CH$_2$CH$_2$CH$_2$CH$_2$CH$_2$CH$_2$); 1.37 (broad m, 4 H, CH$_2$CH$_2$CH$_2$CH$_2$CH$_2$CH$_2$CH$_2$CH$_2$CH$_2$CH$_2$); 1.67, (quint, J=6.86 Hz, 4 H, CH$_2$CH$_2$CH$_2$CH$_2$CH$_2$CH$_2$CH$_2$CH$_2$CH$_2$CH$_2$); 2.70 (t, J=7.30 Hz, 4 H, ArCH$_2$CH$_2$N); 3.29 (t, J=6.52 Hz, 4 H, ArCH$_2$CH$_2$N); 3.90 (t, J=6.54 Hz, 4 H, ArOCH$_2$); 6.87 (d, J=8.56 Hz, 4 H, ArH); 7.15 (t, J=5.56 Hz, 4 H, ArH); 7.56 (t, J=5.30 Hz, 4 H, ArH).

Elemental analyses calculated for C$_{30}$H$_{48}$N$_6$O$_2$, 2 CF$_3$COOH (752.78): C: 54.25%; H: 6.69%; N: 11.16% found: C: 53.95%; H: 6.92%; N: 11.07%.

Example 4

Synthesis of bis(4-(amidinoalkyl)phenoxy)alkanes 1) bis(4-(cyanoalkyl)phenoxy)alkane

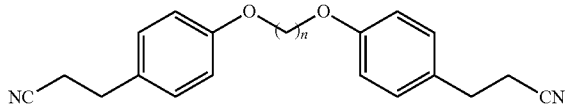

3-(4-hydroxyphenyl)-propionitrile is dissolved in CH$_3$CN (freshly distilled on CaH$_2$) and K$_2$CO$_3$ is added. The mixture is heated under reflux under argon for about two hours before adding dichloro-alkane. After 24 hours under reflux, 0.3 equivalent of dichloro-alkane is added. After reaction for 48 H, return to ambient temperature is followed by evaporation of the solvent. The crude product obtained is dissolved in CH$_2$Cl$_2$ and filtered on a glass frit to remove mineral impurities. The filtrate is then concentrated to a minimum of solvent and is subjected to precipitation by adding MeOH accompanied by cold evaporation. The solid obtained is then filtered, rinsed with MeOH and dried under vacuum.

Different Protocol:

3-(4-Hydroxyphenyl)propionitrile [Heymans et al.; Bioorg. Med. Chem. 2008, 13, 1989-2007] (1 eq.) is dissolved in 15 mL of DMF (dried over CaSO$_4$) and K$_2$CO$_3$ is added (2 eq.), then it is heated at 70° C. for 30 minutes before adding the dihaloalkane (0.5 eq.). After maintaining at 70° C. overnight, return to ambient temperature is followed by adding the reaction mixture to a large volume of water, leading to the formation of a white precipitate. The latter is then filtered on a frit, rinsed with water and dried under vacuum. The solid obtained is dissolved in a minimum of CH$_2$Cl$_2$ and precipitated again by adding an excess of MeOH. After filtration, washing with MeOH and drying, the expected pure compound is obtained, in the form of white flakes.

Variants using DMF in the presence of NaH at 50° C. or CH$_3$CN in the presence of K$_2$CO$_3$ at 90° C. are also applicable.

Homologation of the propionitrile chains of this compound (bis(4-(cyanoalkyl)phenoxy)alkane) can be carried out according to the following protocol:

a) Hydrolysis in an acid medium to give the diacid, then esterification in ethanol in the presence of sulphuric acid, to give the diester of the following formula:

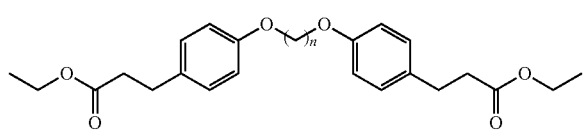

The bis-propionitrile previously obtained is hydrolysed in an acetic acid/concentrated sulphuric acid/water mixture at about 100° C. Addition of cold water causes precipitation of the diacid, which is collected by filtration, washed with water and dried under vacuum. This diacid is then converted to ethyl diester by treatment with a concentrated sulphuric acid/ethanol mixture under reflux, followed by precipitation by adding water, filtration, washing with water and drying, then chromatography if necessary.

A possible alternative to this esterification is the reaction of the diacid with two equivalents of KOH (or of CsOH) in water, followed by lyophilization, giving the double salt of potassium (or of caesium). This salt is reacted with about two equivalents of ethyl halide (or tosylate or mesylate) in anhydrous dimethylformamide. After checking for the end of reaction by chromatography, an excess of ice water is added, to give a precipitate of the diester (or a gum), which is separated by filtration (or decanting). The crude diester bis(4-(2-(ethoxycarbonyl)-ethyl)phenoxy)alkane is purified by chromatography.

b) Reduction of the diester by LiAlH$_4$ to give the diol of the following formula:

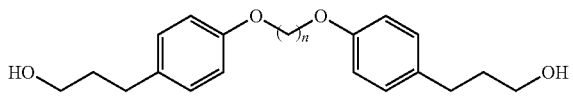

The ethyl diester previously obtained is treated in anhydrous THF (or diethyl ether) with one equivalent of lithium aluminium hydride. Chromatographic monitoring incorporating treatment of the sample according to the standard of this reaction is carried out before stopping the reaction. The excess of hydride is destroyed by careful addition of water, or ethyl acetate. The solid residue is removed by filtration, and vacuum evaporation of the filtrate gives the sought bis(4-(hydroxypropyl)phenoxy)alkane. The latter can be purified on a short column of silica or alumina c) Halogenation of the diol with carbon tetrachloride in the presence of triphenylphosphine to give the dihalogenated compound of the following formula:

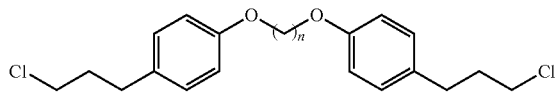

The preceding bis(4-(hydroxypropyl)phenoxy)alkane is solubilized in dichloromethane, with two equivalents of triphenylphosphine. The solution is cooled to 0° C., and an excess of carbon tetrachloride is added. The reaction mixture is stirred at ambient temperature and the reaction is monitored by chromatography; when all the diol has disappeared, the solvents are evaporated off and the residue is chromatographed on silica or alumina to give the sought bis(4-(chloropropyl)phenoxy)alkane.

The dibrominated derivative can be obtained similarly, replacing the carbon tetrachloride with carbon tetrabromide.

An alternative synthesis is the addition of an excess of thionyl chloride at 0° C. to a solution of diol in anhydrous dichloromethane. The reaction is monitored by chromatography. When the alcohol has been consumed, the solvent and the excess thionyl chloride are distilled or evaporated under vacuum, to give the crude dichlorinated derivative, which can be chromatographed.

d) Nucleophilic substitution with NaCN on the dihalogen compound in a substitution-promoting solvent, to give the homologated bis(4-(cyanoalkyl)phenoxy)alkane of the following formula:

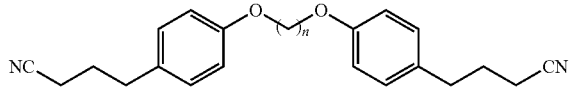

The preceding bis(4-(chloropropyl)phenoxy)alkane is dissolved in dry dimethylsulphoxide, and sixteen equivalents of potassium cyanide (or sodium cyanide) are added in one go. The mixture is heated under an inert atmosphere at 80° C. The reaction is monitored by chromatography. When all the dichlorinated derivative has been consumed, the mixture is cooled to ambient temperature and ice water is added to give a precipitate (or a gum), which is isolated by filtration or decanting. After drying, the solid or the gum obtained is chromatographed to give the sought bis(4-(cyanopropyl)phenoxy)alkane.

All of the stages a-d are repetitive.

a) Example of synthesis of
1,3-bis(4-(2-cyanoethyl)phenoxy)propane

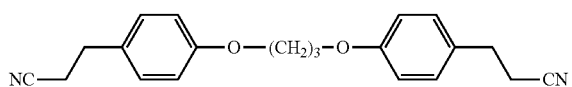

3-(4-Hydroxyphenyl)propionitrile [Heymans et al.; Bioorg. Med. Chem. 2008, 13, 1989-2007 (1.0 g, 6.79 mmol, 1 eq.) is dissolved in 15 mL of DMF (dried over CaSO$_4$) and K$_2$CO$_3$ is added (1.87 g, 13.58 mmol, 2 eq.) and heated at 70° C. for 30 minutes before adding dibromopropane (0.68 g, 3.39 mmol, 0.5 eq.). After maintaining at 70° C. overnight, return to ambient temperature is followed by adding the reaction mixture to a large volume of water, leading to the formation of a white precipitate. The latter is then filtered on a frit, rinsed with water and dried under vacuum. The solid obtained is dissolved in a minimum of CH$_2$Cl$_2$ and precipitated again by adding an excess of MeOH. After filtration, washing with MeOH and drying, the expected pure compound is obtained, in the form of white flakes (0.45 g, 41%).

Variants using DMF in the presence of NaH at 50° C. or CH$_3$CN in the presence of K$_2$CO$_3$ at 90° C. are also applicable.

$^1$H-NMR (400 MHz, CDCl$_3$): 2.24 (q, J=6.1 Hz, 2 H, OCH$_2$CH$_2$); 2.57 (t, J=7.3 Hz, 4 H, CH$_2$CH$_2$CN); 2.88 (t, J=6.3 Hz, 4 H, CH$_2$CH$_2$CN); 4.14 (t, J=6.0 Hz, 4 H, OCH$_2$CH$_2$); 6.88 (d, J=8.6 Hz, 4 H, ArH$_o$); 7.14 (d, J=8.6 Hz, 4 H, ArH$_m$).

$^{13}$C-NMR (100 MHz, CDCl$_3$): 19.67 (CH$_2$CH$_2$CN); 29.28 (OCH$_2$CH$_2$); 30.74 (CH$_2$CH$_2$CN); 64.44 (OCH$_2$CH$_2$); 114.84 (C$_o$); 119.33 (CN); 129.38 (C$_m$); 130.28 (C$_r$); 158.03 (C$_{ipso}$).

Elementary analysis calculated for C$_{21}$H$_{22}$O$_2$N$_2$ (334.41): C: 75.42%; H: 6.63%; N: 8.38%; found: C: 75.51%; H: 6.70%; N: 8.42%.

MS (ES$^+$): 335.17 [M+H$^{1+}$]$^+$; 357.16 [M+Na$^+$]$^+$.

b) Synthesis of Similar Compounds

The compounds
1,4-bis(4-(2-cyanoethyl)phenoxy)butane,
1,5-bis(4-(2-cyanoethyl)phenoxy)pentane,
1,6-bis(4-(2-cyanoethyl)phenoxy)hexane,
1,7-bis(4-(2-cyanoethyl)phenoxy)heptane, 1,8-bis(4-(2-cyanoethyl)phenoxy)octane,
1,9-bis(4-(2-cyanoethyl)phenoxy)nonane,
1,10-bis(4-(2-cyanoethyl)phenoxy)decane
are prepared following the protocols described above to arrive at 1,1-bis(4-(2-cyanoethyl)phenoxy)methane (using respectively dibromopropane, dibromobutane, dibromopentane, dibromohexane, dibromoheptane, dibromooctane, dibromononane and dichlorodecane in place of dichloromethane), or the corresponding dichloro- or diiodo- or di-para-toluene sulphonyl alkanes.

The characteristics of these compounds are described below.

1,4-bis(4-(2-cyanoethyl)phenoxy)butane $^1$H-NMR (400 MHz, CDCl$_3$): 1.97 (m, 4 H, OCH$_2$CH$_2$); 2.57 (t, J=7.3 Hz, 4 H, CH$_2$CH$_2$CN); 2.89 (t, J=7.3 Hz, 4 H, CH$_2$CH$_2$CN); 4.02 (t, J=5.0 Hz, 4 H, OCH$_2$CH$_2$); 6.87 (d, J=8.6 Hz, 4 H, ArH$_o$); 7.15 (d, J=8.6 Hz, 4 H, ArH$_m$).

$^{13}$C-NMR (100 MHz, CDCl$_3$): 19.67 (CH$_2$CH$_2$CN); 29.28 (OCH$_2$CH$_2$); 30.74 (CH$_2$CH$_2$CN); 64.44 (OCH$_2$CH$_2$); 114.84 (C$_o$); 119.33 (CN); 129.38 (C$_m$); 130.28 (C$_r$); 158.03 (C$_{ipso}$).

Elementary analysis calculated for C$_{21}$H$_{22}$O$_2$N$_2$ (348.44): C: 75.83%; H: 6.94%; N: 8.03%; found: C: 75.37%; H: 6.88%; N: 7.86%.

1,5-bis(4-(2-cyanoethyl)phenoxy)pentane $^1$H-NMR (400 MHz, CDCl$_3$): 1.63 (m, 2 H, OCH$_2$CH$_2$CH$_2$); 1.86 (m, 4 H, OCH$_2$CH$_2$CH$_2$); 2.58 (t, J=7.3 Hz, 4 H, CH$_2$CH$_2$CN); 2.90 (t, J=6.3 Hz, 4 H, CH$_2$CH$_2$CN); 3.97 (t, J=6.3 Hz, 2 H, OCH$_2$); 6.86 (d, J=8.3 Hz, 4 H, ArH); 7.14 (d, J=8.6 Hz, 4 H, ArH).

$^{13}$C-NMR (100 MHz, CDCl$_3$): 20.12 (CH$_2$CH$_2$CN); 23.15 (OCH$_2$CH$_2$CH$_2$); 29.43 (OCH$_2$CH$_2$CH$_2$); 31.18 (CH$_2$CH$_2$CN); 68.19 (OCH$_2$); 115.23 (C$_o$); 119.71 (CN); 129.73 (C$_m$); 130.45 (C$_r$); 158.63 (C$_{ipso}$).

Elementary analysis calculated for C$_{23}$H$_{26}$O$_2$N$_2$ (362.46): C: 76.21%; H: 7.23%; N: 7.73%; found: C: 76.16%; H: 7.19%; N: 7.84%.

1,6-bis(4-(2-cyanoethyl)phenoxy)hexane $^1$H-NMR (400 MHz, CDCl$_3$): 1.54 (q, OCH$_2$CH$_2$CH$_2$); 1.81 (m, 4 H, OCH$_2$CH$_2$CH$_2$); 2.57 (t, J=7.3 Hz, 4 H, CH$_2$CH$_2$CN); 2.89 (t, J=7.3 Hz, 4 H, CH$_2$CH$_2$CN); 3.96 (t, J=5.0 Hz, 4 H, OCH$_2$); 6.86 (d, J=8.6 Hz, 4 H, ArH$_o$); 7.14 (d, J=8.6 Hz, 4 H, ArH$_m$).

$^{13}$C-NMR (100 MHz, CDCl$_3$): 20.02 (CH$_2$CH$_2$CN); 26.29, 26.62 (OCH$_2$CH$_2$CH$_2$ and OCH$_2$CH$_2$CH$_2$); 31.16 (CH$_2$CH$_2$CN); 68.27 (OCH$_2$); 115.23 (C$_o$); 119.75 (CN); 129.74 (C$_m$); 130.44 (C$_r$); 158.68 (C$_{ipso}$).

Elementary analysis calculated for C$_{24}$H$_{28}$O$_2$N$_2$ (376.22): C: 76.56%; H: 7.46%; N: 7.44%; found: C: 76.22%; H: 7.42%; N: 7.13%.

1,7-bis(4-(2-cyanoethyl)phenoxy)heptane $^1$H-NMR (400 MHz, CDCl$_3$): 1.46 (m, 6 H, OCH$_2$CH$_2$CH$_2$CH$_2$); 1.76 (m, 4 H, OCH$_2$CH$_2$CH$_2$CH$_2$); 2.57 (t, J=7.3 Hz, 4 H, CH$_2$CH$_2$CN); 2.89 (t, J=7.3 Hz, 4 H, CH$_2$CH$_2$CN); 3.94 (t, J=6.5 Hz, 4 H, OCH$_2$CH$_2$); 6.86 (d, J=8.6 Hz, 4 H, ArH$_o$); 7.13 (d, J=8.6 Hz, 4 H, ArH$_m$).

$^{13}$C-NMR (100 MHz, CDCl$_3$): 19.73 (CH$_2$CH$_2$CN); 26.04, 29.17, 29.24 (OCH$_2$CH$_2$CH$_2$CH$_2$); 30.82 (CH$_2$CH$_2$CN); 67.98 (OCH$_2$); 114.85 (C$_o$); 119.36 (CN); 129.35 (C$_m$); 130.02 (C$_p$); 158.32 (C$_{ipso}$).

Elementary analysis calculated for C$_{25}$H$_{30}$O$_2$N$_2$ (390.52): C: 76.89%; H: 7.74%; N: 7.17%; found: C: 75.94%; H: 7.80%; N: 7.07%.

1,8-bis(4-(2-cyanoethyl)phenoxy)octane $^1$H-NMR (400 MHz, CDCl$_3$): 1.40 (m, 4H, OCH$_2$CH$_2$CH$_2$CH$_2$); 1.46 (m, 4 H, OCH$_2$CH$_2$CH$_2$); 1.78 (m, 4 H, OCH$_2$CH$_2$); 2.57 (t, J=7.3 Hz, 4 H, CH$_2$CH$_2$CN); 2.88 (t, J=7.3 Hz, 4 H, CH$_2$CH$_2$CN); 3.94 (t, J=5.0 Hz, 4 H, OCH$_2$); 6.56 (d, J=8.6 Hz, 4 H, ArH); 7.14 (d, J=8.6 Hz, 4 H, ArH).

$^{13}$C-NMR (100 MHz, CDCl$_3$): 19.70 (CH$_2$CH$_2$CN); 26.01 (OCH$_2$CH$_2$CH$_2$CH$_2$), 29.26, 29.32 (OCH$_2$CH$_2$CH$_2$ and OCH$_2$CH$_2$CH$_2$); 31.78 (CH$_2$CH$_2$CN); 67.99 (OCH$_2$); 114.83 (C$_o$); 119.35 (CN); 129.33 (C$_m$); 129.99 (C$_r$); 158.32 (C$_{ipso}$).

Elementary analysis calculated for C$_{26}$H$_{32}$O$_2$N$_2$ (404.54): C: 77.19%; H: 7.97%; N: 6.92%; found: C: 76.75%; H: 7.80%; N: 7.66%.

1,9-bis(4-(2-cyanoethyl)phenoxy)nonane $^1$H-NMR (400 MHz, CDCl$_3$): 1.36 (m, 6 H, OCH$_2$CH$_2$CH$_2$CH$_2$CH$_2$); 1.45 (m, 4 H, OCH$_2$CH$_2$CH$_2$); 1.78 (q, 4 H, OCH$_2$CH$_2$); 2.58 (t, J=7.3 Hz, 4 H, CH$_2$CH$_2$CN); 2.89 (t, J=7.3 Hz, 4 H, CH$_2$CH$_2$CN); 3.93 (t, J=6.5 Hz, 4 H, OCH$_2$CH$_2$); 6.85 (d, J=8.6 Hz, 4 H, ArH); 7.13 (d, J=8.6 Hz, 4 H, ArH).

$^{13}$C-NMR (100 MHz, CDCl$_3$): 20.12 (CH$_2$CH$_2$CN); 26.44, 29.66, 29.71, 29.88 (OCH$_2$CH$_2$CH$_2$CH$_2$CH$_2$); 31.19 (CH$_2$CH$_2$CN); 68.40 (OCH$_2$); 115.22 (C$_o$); 119.71 (CN); 129.70 (C$_m$); 130.34 (C$_p$); 158.72 (C$_{ipso}$).

Elementary analysis calculated for C$_{27}$H$_{34}$O$_2$N$_2$ (418.57): C: 77.48%; H: 8.19%; N: 6.69%; found: C: 77.35%; H: 8.12%; N: 6.76%.

1,10-bis(4-(2-cyanoethyl)phenoxy)decane $^1$H-NMR (400 MHz, CDCl$_3$): 1.33 (m, 8 H, OCH$_2$CH$_2$CH$_2$CH$_2$CH$_2$); 1.45 (m, 4 H, OCH$_2$CH$_2$CH$_2$); 1.78 (q, 4 H, OCH$_2$CH$_2$); 2.58 (t, J=7.4 Hz, 4 H, CH$_2$CH$_2$CN); 2.89 (t, J=7.4 Hz, 4 H, CH$_2$CH$_2$CN); 3.93 (t, J=6.5 Hz, 4 H, OCH$_2$CH$_2$); 6.85 (d, J=8.6 Hz, 4 H, ArH); 7.13 (d, J=8.6 Hz, 4 H, ArH).

$^{13}$C-NMR (100 MHz, CDCl$_3$): 19.75 (CH$_2$CH$_2$CN); 26.10, 29.32, 29.42, 29.55 (OCH$_2$CH$_2$CH$_2$CH$_2$CH$_2$); 30.83 (CH$_2$CH$_2$CN); 68.08 (OCH$_2$); 114.88 (C$_o$); 119.37 (CN); 129.35 (C$_m$); 130.00 (C$_p$); 158.38 (C$_{ipso}$).

Elementary analysis calculated for C$_{28}$H$_{36}$O$_2$N$_2$, 1/6CH$_2$Cl$_2$ (446.75): C: 75.72%; H: 8.19%; N: 6.27%; found: C: 75.66%; H: 8.17%; N: 6.21%.

2) bis(4-(amidinoalkyl)phenoxy)alkane

A solution of bis(4-(cyanoalkyl)phenoxy)alkane derivative in a mixture of ethanol and anhydrous benzene is cooled to 0° C., then it is treated by bubbling with gaseous hydrochloric acid for about 1 hour. The acid solution is stored at 4°

C. for several days. The volatile part of the hydrochloric acid is removed by bubbling with dry nitrogen, and the degassed solution is evaporated to dryness under reduced pressure. The evaporation residue, containing the dihydrochloride of bis(4-(ethyl)imidatoalkyl)phenoxy)alkane is taken up in a 1M solution of ammonia in ethanol. The mixture is heated at 50-60° C. under anhydrous conditions for 2-3h, then it is stirred overnight at ambient temperature. The resultant mixture is filtered, then diethyl ether is added, causing precipitation of the sought dihydrochloride of bis(4-(amidinoalkyl)phenoxy) alkane.

Different protocol in two stages, isolating the intermediate imidate compounds

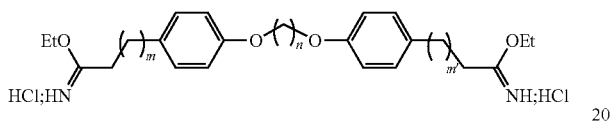

The compound bis(4-(cyanoalkyl)phenoxy)alkane is dissolved in an EtOH/benzene mixture and it is bubbled with HCl gas, with stirring at 4° C., for about two hours. The mixture is then stirred at ambient temperature for 48 h before evaporating the solvents under vacuum. The oil obtained is then solubilized in a minimum of EtOH and the expected bis-imidate is precipitated by adding a large excess of $Et_2O$. The white precipitate is then filtered on a frit, washed with $Et_2O$ and dried under vacuum. The sought compound is obtained in the form of a white powder.

The bis-hydrochloride of bis(4-[(imidato)alkyl]phenoxy) alkane is dissolved in EtOH and it is bubbled with gaseous $NH_3$ for about 1.5h. The mixture is then refluxed under argon for 5 to 6 h. Return to ambient temperature is followed by precipitation of the salt of bis-amidine by adding an excess of $Et_2O$ to the mixture. The precipitate is filtered, washed with ether and dried under vacuum. The expected product is obtained in the form of a white powder.

a) Examples of Synthesis of Imidate Compounds 1,3-bis(4-(3-(ethyl-propanimidoate)phenoxy)propane, bis-hydrochloride

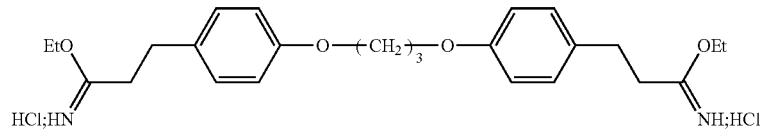

The compound 1,3-bis(4-(2-cyanoethyl)phenoxy)propane (0.24 g, 0.72 mmol) is dissolved in EtOH/benzene mixture (7/15 mL) and it is bubbled with HCl gas, with stirring at 4° C., for about two hours. The mixture is then stirred at ambient temperature for 48 h before evaporating the solvents under vacuum. The oil obtained is then solubilized in a minimum of EtOH and the expected bis-imidate is precipitated by adding a large excess of $Et_2O$. The white precipitate is then filtered on a frit, washed with $Et_2O$ and dried under vacuum. The sought compound is obtained in the form of a white powder (0.24 g, 67%).

$^1$H-NMR (400 MHz, DMSO-$D_6$): 1.31 (t, J=6.9 Hz, 6 H, $OCH_2CH_3$); 2.14 (m, 4 H, $OCH_2CH_2$); 2.88 (broad s, 8 H, $ArCH_2CH_2$); 4.09 (t, J=6.1 Hz, 4 H, $OCH_2$); 4.36 (q, J=6.8 Hz, 4 H, $OCH_2CH_3$); 6.90 (d, J=8.6 Hz, 4 H, ArH); 7.16 (d, J=8.6 Hz, 4 H, ArH); 11.06, 11.79 (broad s, 4 H, $NH_2Cl$).

Elementary analysis calculated for $C_{25}H_{36}O_4N_2Cl_2$, 0.75 $H_2O$ (512.98): C: 58.53%; H: 7.36%; N: 5.46%; found: C: 58.62%; H: 7.26%; N: 5.54%.

*Similar Compounds

The following compounds:
1,4-bis(4-(3-(ethyl-propanimidoate)phenoxy)butane, bis-hydrochloride
1,5-bis(4-(3-(ethyl-propanimidoate)phenoxy)pentane, bis-hydrochloride
1,6-bis(4-(3-(ethyl-propanimidoate)phenoxy)hexane, bis-hydrochloride
1,7-bis(4-(3-(ethyl-propanimidoate)phenoxy)heptane, bis-hydrochloride
1,8-bis(4-(3-(ethyl-propanimidoate)phenoxy)octane, bis-hydrochloride
1,9-bis(4-(3-(ethyl-propanimidoate)phenoxy)nonane, bis-hydrochloride
1,10-bis(4-(3-(ethyl-propanimidoate)phenoxy)decane, bis-hydrochloride
are prepared following the protocols described above to arrive at 1,3-bis(4-(3-(ethyl-propanimidoate)phenoxy)propane, bis-hydrochloride.

The characteristics of these compounds are described below.

1,4-bis(4-(3-(ethyl-propanimidoate)phenoxy)butane, bis-hydrochloride $^1$H-NMR (400 MHz, DMSO-$D_6$): 1.32 (t, J=7.1 Hz, 6 H, $OCH_2CH_3$); 1.85 (broad s, 4 H, $OCH_2CH_2$); 2.88 (broad s, 8 H, $ArCH_2CH_2$); 4.00 (broad s, 4 H, $OCH_2$); 4.36 (q, J=6.8 Hz, 4 H, $OCH_2CH_3$); 6.88 (d, J=8.6 Hz, 4 H, ArH); 7.15 (d, J=8.6 Hz, 4 H, ArH); 10.98, 11.68 (broad s's, $NH_2Cl$).

Elementary analysis calculated for $C_{26}H_{38}O_4N_2Cl_2$, 1.5 $H_2O$ (540.53): C: 57.77%; H: 7.64%; N: 5.18%; found: C: 57.89%; H: 7.50%; N: 5.22%.

1,5-bis(4-(3-(ethyl-propanimidoate)phenoxy)pentane, bis-hydrochloride $^1$H-NMR (400 MHz, DMSO-$D_6$): 1.32 (t, J=7.1 Hz, 6 H, $OCH_2CH_3$); 1.56 (m, 2 H, $OCH_2CH_2CH_2$); 1.76 (q, 4 H, $OCH_2CH_2$); 2.88 (broad s, 8 H, $ArCH_2CH_2$); 3.95 (t, J=6.3 Hz, 4 H, $OCH_2$); 4.36 (q, J=7.1 Hz, 4 H, $OCH_2CH_3$); 6.87 (d, J=8.6 Hz, 4 H, ArH); 7.14 (d, J=8.6 Hz, 4 H, ArH); 10.96, 11.72 (broad s, 4 H, $NH_2Cl$).

Elementary analysis calculated for $C_{27}H_{40}O_4N_2Cl_2$, 0.5 $H_2O$ (536.53): C: 60.44%; H: 7.70%; N: 5.22%; found: C: 60.40%; H: 7.67%; N: 5.41%.

1,6-bis(4-(3-(ethyl-propanimidoate)phenoxy)hexane, bis-hydrochloride $^1$H-NMR (400 MHz, DMSO-$D_6$): 1.32 (t, J=7.1 Hz, 6 H, $OCH_2CH_3$); 1.46 (broad s, 4 H, $OCH_2CH_2CH_2$); 1.70 (m, 4 H, $OCH_2CH_2$); 2.87 (broad s, 8 H, $ArCH_2CH_2$); 3.93 (t, J=6.3

Hz, 4 H, OCH$_2$); 4.36 (q, J=7.1 Hz, 4 H, OCH$_2$CH$_3$); 6.87 (d, J=8.6 Hz, 4 H, ArH); 7.14 (d, J=8.6 Hz, 4 H, ArH); 11.04, 11.64 (broad s, 4 H, NH$_2$Cl).

Elementary analysis calculated for C$_{28}$H$_{42}$O$_4$N$_2$Cl$_2$, 0.5 H$_2$O (550.56): C: 61.09%; H: 7.87%; N: 5.08%; found: C: 60.91%; H: 7.77%; N: 5.20%.

1,7-bis(4-(3-(ethyl-propanimidoate)phenoxy)heptane, bis-hydrochloride $^1$H-NMR (400 MHz, DMSO-D$_6$): 1.32 (t, J=7.0 Hz, 6 H, OCH$_2$CH$_3$); 1.40 (broad s, 6 H, OCH$_2$CH$_2$CH$_2$CH$_2$); 1.70 (m, 4 H, OCH$_2$CH$_2$); 2.88 (broad s, 8 H, ArCH$_2$CH$_2$); 3.93 (t, J=6.4 Hz, 4 H, OCH$_2$); 4.36 (q, J=7.1 Hz, 4 H, OCH$_2$CH$_3$); 6.86 (d, J=8.6 Hz, 4 H, ArH); 7.14 (d, J=8.6 Hz, 4 H, ArH); 11.14, 11.58 (broad s, 4 H, NH$_2$Cl).

Elementary analysis calculated for C$_{29}$H$_{44}$O$_4$N$_2$Cl$_2$, 0.75 H$_2$O (568.99): C: 61.21%; H: 8.05%; N: 4.92%; found: C: 64.41%; H: 7.95%; N: 5.11%.

1,8-bis(4-(3-(ethyl-propanimidoate)phenoxy)octane, bis-hydrochloride $^1$H-NMR (400 MHz, DMSO-D$_6$): 1.32 (t, J=7.1 Hz, 6 H, OCH$_2$CH$_3$); 1.33 (broad s, 4 H, OCH$_2$CH$_2$CH$_2$CH$_2$); 1.41 (broad s, 4 H, OCH$_2$CH$_2$CH$_2$); 1.69 (q, 4 H, OCH$_2$CH$_2$); 2.88 (broad s, 8 H, ArCH$_2$CH$_2$); 3.92 (t, J=6.4 Hz, 4 H, OCH$_2$); 4.36 (q, J=7.1 Hz, 4 H, OCH$_2$CH$_3$); 6.86 (d, J=8.3 Hz, 4 H, ArH); 7.14 (d, J=8.6 Hz, 4 H, ArH); 10.99, 11.73 (broad s, 4 H, NH$_2$Cl).

Elementary analysis calculated for C$_{20}$H$_{46}$O$_4$N$_2$Cl$_2$, 0.5 H$_2$O (578.61): C: 62.27%; H: 8.18%; N, 4.84%; found: C: 62.23%; H: 8.09%; N: 5.05%.

1,9-bis(4-(3-(ethyl-propanimidoate)phenoxy)nonane, bis-hydrochloride $^1$H-NMR (400 MHz, DMSO-D$_6$): 1.32 (m, 12 H, OCH$_2$CH$_2$CH$_2$CH$_2$CH$_2$ and OCH$_2$CH$_3$); 1.40 (m, 4 H, OCH$_2$CH$_2$CH$_2$); 1.69 (q, 4 H, OCH$_2$CH$_2$); 2.87 (broad s, 8 H, ArCH$_2$CH$_2$); 3.92 (t, J=6.4 Hz, 4 H, OCH$_2$); 4.35 (q, J=7.1 Hz, 4 H, OCH$_2$CH$_3$); 6.86 (d, J=8.6 Hz, 4 H, ArH); 7.14 (d, J=8.6 Hz, 4 H, ArH); 10.91, 11.48 (broad s, 4 H, NH$_2$Cl).

Elementary analysis calculated for C$_{31}$H$_{48}$O$_4$N$_2$Cl$_2$, 0.25 H$_2$O (588.13): C: 63.30%; H: 8.31%; N: 4.76%; found: C: 63.42%; H: 8.23%; N: 4.95%.

1,10-bis(4-(3-(ethyl-propanimidoate)phenoxy)decane, bis-hydrochloride $^1$H-NMR (400 MHz, DMSO-D$_6$): 1.30 (broad s, 6 H, OCH$_2$CH$_2$CH$_2$CH$_2$CH$_2$); 1.32 (t, J=7.1 Hz, 6 H, OCH$_2$CH$_3$); 1.40 (m, 4 H, OCH$_2$CH$_2$CH$_2$); 1.68 (q, 4 H, OCH$_2$CH$_2$); 2.87 (broad s, 8 H, ArCH$_2$CH$_2$); 3.91 (t, J=6.4 Hz, 4 H, OCH$_2$); 4.35 (q, J=7.1 Hz, 4 H, OCH$_2$CH$_3$); 6.86 (d, J=8.6 Hz, 4 H, ArH); 7.14 (d, J=8.6 Hz, 4 H, ArH); 10.92, 11.65 (broad s, 4 H, NH$_2$Cl).

Elementary analysis calculated for C$_{32}$H$_{50}$O$_4$N$_2$Cl$_2$, 0.5 H$_2$O (606.67): C: 63.35%; H: 8.47%; N: 4.61%; found: C: 63.20%; H: 8.47%; N: 4.61%.

b) Examples of Synthesis of Amidine Compounds 1,3-bis(4-(2-(amidino)ethyl)phenoxy)propane, bis-hydrochloride; compound 103

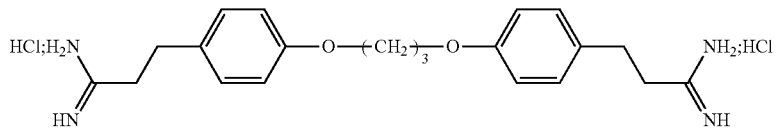

The bis-hydrochloride of 1,3-bis(4-(3-(ethyl-propanimidoate)phenoxy)propane (0.17 g, 0.34 mmol) is dissolved in 15 mL of EtOH and it is bubbled with NH$_3$ for about 1.5h. The mixture is then refluxed under argon for 5 to 6 h. Return to ambient temperature is followed by precipitation of the bis-amidine by adding an excess of Et$_2$O to the mixture. The precipitate is filtered, washed with ether and dried under vacuum. The expected product is obtained in the form of a white powder (0.13 g, 88%).

$^1$H-NMR (400 MHz, DMSO-D$_6$): 2.15 (t, J=6.1 Hz, 2 H, OCH$_2$CH$_2$); 2.64 (t, J=7.8 Hz, 4 H, ArCH$_2$CH$_2$ or ArCH$_2$CH$_2$); 2.88 (t, J=7.8 Hz, 4 H, ArCH$_2$CH$_2$ or ArCH$_2$CH$_2$); 3.32 (s, 2 H, NH); 4.10 (t, J=6.3 Hz, 4 H, OCH$_2$); 6.90 (d, J=8.6 Hz, 4 H, ArH); 7.16 (d, J=8.6 Hz, 4 H, ArH); 8.64, 9.04 (broad s's, 6 H, NH$_3$).

$^1$H-NMR (400 MHz, D$_2$O): 2.06 (t, J=5.8 Hz, 2 H, OCH$_2$CH$_2$); 2.63 (t, J=7.3 Hz, 4 H, ArCH$_2$CH$_2$ or ArCH$_2$CH$_2$); 2.85 (t, J=7.2 Hz, 4 H, ArCH$_2$CH$_2$ or ArCH$_2$CH$_2$); 4.04 (t, J=5.8 Hz, 4 H, OCH$_2$); 6.83 (d, J=8.3 Hz, 4 H, ArH); 7.11 (d, J=8.1 Hz, 4 H, ArH).

$^{13}$C-NMR (100 MHz, D$_2$O): 28.66, 31.55, 34.40 (OCH$_2$CH$_2$, ArCH$_2$CH$_2$); 65.56 (OCH$_2$); 115.37 (C$_o$); 130.09 (C$_m$); 131.91 (CN); 157.26 (C$_{ipso}$); 170.72 (C$_{amidine}$).

Elementary analysis calculated for C$_{21}$H$_{30}$O$_2$N$_4$Cl$_2$, 0.5 H$_2$O (450.39): C: 56.00%; H: 6.93%; N: 12.43%; found: C: 56.13%; H: 6.79%; N: 12.61%.

Similar Compounds

The following compounds:
- 1,4-bis(4-(2-(amidino)ethyl)phenoxy)butane, bis-hydrochloride
- 1,5-bis(4-(2-(amidino)ethyl)phenoxy)pentane, bis-hydrochloride
- 1,6-bis(4-(2-(amidino)ethyl)phenoxy)hexane, bis-hydrochloride
- 1,7-bis(4-(2-(amidino)ethyl)phenoxy)heptane, bis-hydrochloride
- 1,8-bis(4-(2-(amidino)ethyl)phenoxy)octane, bis-hydrochloride
- 1,9-bis(4-(2-(amidino)ethyl)phenoxy)nonane, bis-hydrochloride
- 1,10-bis(4-(2-(amidino)ethyl)phenoxy)decane, bis-hydrochloride are prepared following the protocols described above to arrive at 1,3-bis(4-(2-(amidino)ethyl)phenoxy)propane, bis-hydrochloride.

The characteristics of these compounds are described below.

1,4-bis(4-(2-(amidino)ethyl)phenoxy)butane, bis-hydrochloride; compound 104

$^1$H-NMR (400 MHz, DMSO-D$_6$): 1.85 (broad s, 4 H, OCH$_2$CH$_2$); 2.64 (t, J=7.8 Hz, 4 H, ArCH$_2$CH$_2$ or ArCH$_2$CH$_2$); 2.88 (t, J=7.8 Hz, 4 H, ArCH$_2$CH$_2$ or ArCH$_2$CH$_2$); 3.31 (s, 2 H, NH); 4.00 (broad s, 4 H, OCH$_2$); 6.89 (d, J=8.3 Hz, 4 H, ArH); 7.16 (d, J=8.5 Hz, 4 H, ArH); 8.58, 9.00 (broad s's, 6 H, NH$_3$).

$^1$H-NMR (400 MHz, D$_2$O): 1.76 (broad s, 2 H, OCH$_2$CH$_2$); 2.62 (t, J=7.4 Hz, 4 H, ArCH$_2$CH$_2$ or ArCH$_2$CH$_2$); 2.85 (t, J=7.3 Hz, 4 H, ArCH$_2$CH$_2$ or ArCH$_2$CH$_2$); 3.95 (broad s, 4 H, OCH$_2$); 6.82 (d, J=8.6 Hz, 4 H, ArH); 7.11 (d, J=8.3 Hz, 4 H, ArH).

$^{13}$C-NMR (100 MHz, D$_2$O): 25.42, 31.56, 34.41 (OCH$_2$CH$_2$, ArCH$_2$CH$_2$); 68.51 (OCH$_2$); 115.40 (C$_o$); 130.10 (C$_m$); 131.86 (CN); 157.26 (C$_{ipso}$); 170.72 (C$_{amidine}$).

Elementary analysis calculated for C$_{22}$H$_{32}$O$_2$N$_4$Cl$_2$, 0.5 H$_2$O (464.43): C: 56.89%; H: 6.94%; N: 12.06%; found: C: 57.31%; H: 7.40%; N: 11.41%.

1,5-bis(4-(2-(amidino)ethyl)phenoxy)pentane, bis-hydrochloride; compound 105

$^1$H-NMR (400 MHz, DMSO-D$_6$): 1.56 (m, 2 H, OCH$_2$CH$_2$CH$_2$); 1.76 (q, 4 H, OCH$_2$CH$_2$); 2.63 (t, J=7.5 Hz, 4 H, ArCH$_2$CH$_2$ or ArCH$_2$CH$_2$); 2.87 (t, J=7.5 Hz, 4 H, ArCH$_2$CH$_2$ or ArCH$_2$CH$_2$); 3.94 (t, J=6.3 Hz, 4 H, OCH$_2$); 6.87 (d, J=8.9 Hz, 4 H, ArH); 7.14 (d, J=7.8 Hz, 4 H, ArH); 8.58, 8.94 (broad s's, 6 H, NH).

$^1$H-NMR (400 MHz, D$_2$O): 1.55 (q, 2 H, OCH$_2$CH$_2$CH$_2$); 1.78 (q, 4 H, OCH$_2$CH$_2$); 2.73 (t, J=7.4 Hz, 4 H, ArCH$_2$CH$_2$ or ArCH$_2$CH$_2$); 2.95 (t, J=7.4 Hz, 4 H, ArCH$_2$CH$_2$ or ArCH$_2$CH$_2$); 4.03 (t, J=6.3 Hz, 4 H, OCH$_2$); 6.94 (d, J=8.5 Hz, 4 H, ArH); 7.22 (d, J=8.3 Hz, 4 H, ArH).

$^{13}$C-NMR (100 MHz, D$_2$O): 22.14, 28.37, 31.58, 34.42 (OCH$_2$CH$_2$, ArCH$_2$CH$_2$); 68.86 (OCH$_2$); 115.46 (C$_o$); 130.11 (C$_m$); 131.86 (CN); 157.31 (C$_{ipso}$); 170.73 (C$_{amidine}$).

Elementary analysis calculated for C$_{23}$H$_{34}$O$_2$N$_4$Cl$_2$, 0.5 H$_2$O, 0.5 NH$_4$Cl (505.19): C: 54.68%; H: 7.38%; N: 12.47%; found: C: 54.36%; H: 7.26%; N: 12.66%.

1,6-bis(4-(2-(amidino)ethyl)phenoxy)hexane, bis-hydrochloride; compound 106

$^1$H-NMR (400 MHz, DMSO-D$_6$): 1.47 (broad s, 4 H, OCH$_2$CH$_2$CH$_2$); 1.72 (broad s, 4 H, OCH$_2$CH$_2$); 2.64 (t, J=7.8 Hz, 4 H, ArCH$_2$CH$_2$ or ArCH$_2$CH$_2$); 2.87 (t, J=7.8 Hz, 4H, ArCH$_2$CH$_2$ or ArCH$_2$CH$_2$); 3.94 (t, J=6.3 Hz, 4 H, OCH$_2$); 6.87 (d, J=8.3 Hz, 4 H, ArH); 7.15 (d, J=8.1 Hz, 4 H, ArH); 8.60, 9.02 (broad s's, 6 H, NH).

$^1$H-NMR (400 MHz, D$_2$O): 1.32 (broad s, 4 H, OCH$_2$CH$_2$CH$_2$); 1.58 (m, 4 H, OCH$_2$CH$_2$); 2.62 (t, J=7.5 Hz, 4 H, ArCH$_2$CH$_2$ or ArCH$_2$CH$_2$); 2.84 (t, J=7.4 Hz, 4 H, ArCH$_2$CH$_2$ or ArCH$_2$CH$_2$); 3.86 (t, J=6.4 Hz, 4 H, OCH$_2$); 6.80 (d, J=8.6 Hz, 4 H, ArH); 7.11 (d, J=8.3 Hz, 4 H, ArH).

$^{13}$C-NMR (100 MHz, D$_2$O): 25.42, 28.62, 31.56, 34.41 (OCH$_2$CH$_2$, ArCH$_2$CH$_2$); 68.86 (OCH$_2$); 115.38 (C$_o$); 130.08 (C$_m$); 131.80 (CN); 157.34 (C$_{ipso}$); 170.72 (C$_{amidine}$).

Elementary analysis calculated for C$_{24}$H$_{36}$O$_2$N$_4$Cl$_2$, 1/3NH$_4$Cl (501.3): C: 57.50%; H: 7.50%; N: 12.10%; found: C: 57.13%; H: 7.05%; N: 12.10%.

1,7-bis(4-(2-(amidino)ethyl)phenoxy)heptane, bis-hydrochloride; compound 107

$^1$H-NMR (400 MHz, DMSO-D$_6$): 1.41 (broad s, 6 H, OCH$_2$CH$_2$CH$_2$CH$_2$); 1.71 (m, 4 H, OCH$_2$CH$_2$); 2.63 (t, J=7.1 Hz, 4 H, ArCH$_2$CH$_2$ or ArCH$_2$CH$_2$); 2.87 (t, J=7.8 Hz, 4 H, ArCH$_2$CH$_2$ or ArCH$_2$CH$_2$); 3.93 (t, J=6.3 Hz, 4 H, OCH$_2$); 6.87 (d, J=8.6 Hz, 4 H, ArH); 7.15 (d, J=8.3 Hz, 4 H, ArH); 8.57, 9.00 (broad s's, 6 H, NH).

$^1$H-NMR (400 MHz, D$_2$O): 1.16 (broad s, 6 H, OCH$_2$CH$_2$CH$_2$CH$_2$); 1.49 (m, 4 H, OCH$_2$CH$_2$); 2.56 (t, J=7.5 Hz, 4 H, ArCH$_2$CH$_2$ or ArCH$_2$CH$_2$); 2.76 (t, J=7.3 Hz, 4 H, ArCH$_2$CH$_2$ or ArCH$_2$CH$_2$); 3.69 (t, J=6.3 Hz, 4 H, OCH$_2$); 6.69 (d, J=8.3 Hz, 4 H, ArH); 7.04 (d, J=8.6 Hz, 4 H, ArH).

$^{13}$C-NMR (100 MHz, D$_2$O): 25.75, 28.90, 28.94, 31.58, 34.43 (OCH$_2$CH$_2$CH$_2$CH$_2$, ArCH$_2$CH$_2$); 68.61 (OCH$_2$); 115.16 (C$_o$); 129.99 (C$_m$); 131.66 (CN); 157.46 (C$_{ipso}$); 170.66 (C$_{amidine}$).

Elementary analysis calculated for C$_{25}$H$_{38}$O$_2$N$_4$Cl$_2$, 0.5 H$_2$O (497.5): C: 59.28%; H: 7.75%; N: 11.06%; found: C: 58.74%; H: 7.46%; N: 11.47%.

1,8-bis(4-(2-(amidino)ethyl)phenoxy)octane, bis-hydrochloride; compound 108

$^1$H-NMR (400 MHz, DMSO-D$_6$): 1.47 (broad s, 4 H, OCH$_2$CH$_2$CH$_2$); 1.72 (broad s, 4 H, OCH$_2$CH$_2$); 2.64 (t, J=7.8 Hz, 4 H, ArCH$_2$CH$_2$ or ArCH$_2$CH$_2$); 2.87 (t, J=7.8 Hz, 4 H, ArCH$_2$CH$_2$ or ArCH$_2$CH$_2$); 3.31 (s, 2 H, NH); 3.94 (t, J=6.3 Hz, 4 H, OCH$_2$); 6.87 (d, J=8.3 Hz, 4 H, ArH); 7.15 (d, J=8.1 Hz, 4 H, ArH); 8.60, 9.02 (broad s's, 6 H, NH$_3$).

$^1$H-NMR (400 MHz, D$_2$O): 1.25 (m, 4 H, OCH$_2$CH$_2$CH$_2$); 1.42 (m, 4 H, OCH$_2$CH$_2$CH$_2$); 1.63 (m, 4 H, OCH$_2$CH$_2$); 2.62 (t, J=7.4 Hz, 4 H, ArCH$_2$CH$_2$ or ArCH$_2$CH$_2$); 2.85 (t, J=7.3 Hz, 4 H, ArCH$_2$CH$_2$ or ArCH$_2$CH$_2$); 3.93 (t, J=6.1 Hz, 4 H, OCH$_2$); 6.85 (d, J=8.6 Hz, 4 H, ArH); 7.12 (d, J=8.6 Hz, 4 H, ArH).

$^{13}$C-NMR (100 MHz, D$_2$O): 25.83, 28.90, 29.19, 31.58, 34.43 (OCH$_2$CH$_2$CH$_2$CH$_2$, ArCH$_2$CH$_2$); 68.76 (OCH$_2$); 115.22 (C$_o$); 130.00 (C$_m$); 131.61 (CN); 157.43 (C$_{ipso}$); 170.65 (C$_{amidine}$).

Elementary analysis calculated for C$_{26}$H$_{40}$O$_2$N$_4$Cl$_2$, 0.4 H$_2$O (518.73): C: 60.20%; H: 7.92%; N: 10.80%; found: C: 60.34%; H: 7.85%; N: 10.91%.

1,9-bis(4-(2-(amidino)ethyl)phenoxy)nonane, bis-hydrochloride; compound 109

$^1$H-NMR (400 MHz, DMSO-D$_6$): 1.31 (broad s, 6 H, OCH$_2$CH$_2$CH$_2$CH$_2$CH$_2$); 1.40 (broad s, 4 H, OCH$_2$CH$_2$CH$_2$); 1.68 (q, 4 H, OCH$_2$CH$_2$); 2.66 (t, J=7.8 Hz, 4 H, ArCH$_2$CH$_2$ or ArCH$_2$CH$_2$); 2.88 (t, J=7.8 Hz, 4 H, ArCH$_2$CH$_2$ or ArCH$_2$CH$_2$); 3.91 (t, J=6.4 Hz, 4 H, OCH$_2$); 6.85 (d, J=8.3 Hz, 4 H, ArH); 7.16 (d, J=8.6 Hz, 4 H, ArH); 8.77, 9.16 (broad s's, 8 H, NH).

$^1$H-NMR (400 MHz, D$_2$O): 1.32 (m, 6 H, OCH$_2$CH$_2$CH$_2$CH$_2$CH$_2$); 1.41 (m, 4 H, OCH$_2$CH$_2$CH$_2$); 1.73 (q, 4 H, OCH$_2$CH$_2$); 2.73 (t, J=7.4 Hz, 4 H, ArCH$_2$CH$_2$ or ArCH$_2$CH$_2$); 2.95 (t, J=7.4 Hz, 4 H, ArCH$_2$CH$_2$ or ArCH$_2$CH$_2$); 4.04 (t, J=6.5 Hz, 4 H, OCH$_2$); 6.96 (d, J=8.6 Hz, 4 H, ArH); 7.22 (d, J=8.3 Hz, 4 H, ArH).

$^{13}$C-NMR (100 MHz, D$_2$O): 25.89, 29.07, 29.32, 31.47, 34.02 (OCH$_2$CH$_2$CH$_2$CH$_2$CH$_2$, ArCH$_2$CH$_2$); 67.69 (OCH$_2$); 114.71 (C$_o$); 129.63 (C$_m$); 131.40 (CN); 157.67 (C$_{ipso}$); 170.51 (C$_{amidine}$).

Elementary analysis calculated for $C_{27}H_{42}O_2N_4Cl_2$ (525.55): C: 60.70%; H: 8.06%; N: 10.66%; found: C: 61.59%; H: 7.97%; N: 10.58%.

1,10-bis(4-(2-(amidino)ethyl)phenoxy)decane, bis-hydrochloride; compound 110

$^1$H-NMR (400 MHz, DMSO-D$_6$): 1.29 (m, 8 H, OCH$_2$CH$_2$CH$_2$CH$_2$CH$_2$); 1.39 (m, 4 H, OCH$_2$CH$_2$CH$_2$); 1.68 (m, 4 H, OCH$_2$CH$_2$); 2.65 (t, J=7.8 Hz, 4 H, ArCH$_2$CH$_2$ or ArCH$_2$CH$_2$); 2.88 (t, J=7.8 Hz, 4 H, ArCH$_2$CH$_2$ or ArCH$_2$CH$_2$); 3.36 (s, 2 H, NH); 3.91 (t, J=6.3 Hz, 4 H, OCH$_2$); 6.86 (d, J=8.3 Hz, 4 H, ArH); 7.16 (d, J=8.3 Hz, 4 H, ArH); 8.74, 9.12 (broad s's, 6 H, NH$_3$).

$^1$H-NMR (400 MHz, D$_2$O): 1.29 (m, 8 H, OCH$_2$CH$_2$CH$_2$CH$_2$CH$_2$); 1.40 (m, 4 H, OCH$_2$CH$_2$CH$_2$); 1.72 (q, 4 H, OCH$_2$CH$_2$); 2.71 (t, J=7.3 Hz, 4 H, ArCH$_2$CH$_2$ or ArCH$_2$CH$_2$); 2.94 (t, J=7.3 Hz, 4 H, ArCH$_2$CH$_2$ or ArCH$_2$CH$_2$); 4.03 (t, J=6.5 Hz, 4 H, OCH$_2$); 6.95 (d, J=8.6 Hz, 4 H, ArH); 7.21 (d, J=8.8 Hz, 4 H, ArH).

$^{13}$C-NMR (100 MHz, D$_2$O): 25.89, 29.07, 29.13, 29.31, 31.45, 34.99 (OCH$_2$CH$_2$CH$_2$CH$_2$, ArCH$_2$CH$_2$); 67.69 (OCH$_2$); 114.73 (C$_o$); 129.62 (C$_m$); 131.37 (CN); 157.68 (C$_{ipso}$); 170.42 (C$_{amidine}$).

Elementary analysis calculated for $C_{28}H_{44}O_2N_4Cl_2$, 0.5 H$_2$O (548.59): C: 61.30%; H: 8.26%; N: 10.21%; found: C: 61.39%; H: 8.12%; N: 10.16%.

Example 5

Synthesis of bis(para-cyanomethyl)-diphenylalkane

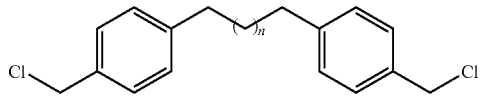

The 1,2-diphenyl alkane is treated with dichloromethyl ether in the presence of zinc chloride (Hager et al., *J. AM Pharm. Ass*, 1952, XLI, 3(6), 115-118; Reichstein and Oppenauer, *Helv. Chim. Acta*, 1933, 16, 1380) or with chloromethyl-n-octyl ether in the presence of titanium tetrachloride, or any other chloromethylating agent, to give the bis(para-chloromethyl)-diphenylalkane.

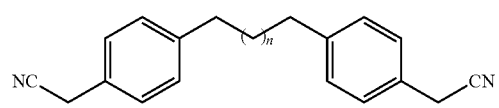

The bis(para-chloromethyl)-diphenylalkane is treated with NaCN in an aqueous-alcoholic mixture (Hager et al., *J. AM. Pharm. Ass*, 1952, XLI, 3(6), 115-118; Reichstein and Oppenauer, *Helv. Chim. Acta*, 1933, 16, 1380), or in any other solvent promoting this nucleophilic substitution to give the bis(para-cyanomethyl)-diphenylalkane.

Homologation of these compounds can be carried out according to the protocol proposed previously.

Example 6

Synthesis of bis(para-guanidinoalkyl)phenoxy)alkanes 1) bis(para-aminoalkyl)phenyl)alkanes

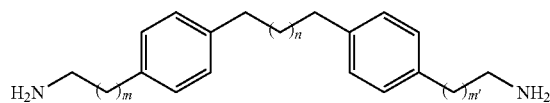

The bis(4-cyanoalkyl)-diphenylalkane in question is dissolved in anhydrous THF, under an inert atmosphere. Between 5 and 10 equivalents of borane:1M THF complex in tetrahydrofuran are added, and the mixture is stirred for 30 minutes at ambient temperature, then it is refluxed for 3 to 4 hours. After cooling to ambient temperature, the mixture is added to an excess of methanol to destroy the excess of borane. The trimethoxyborane, methanol and tetrahydrofuran are evaporated off. The evaporation residue is taken up in a methanol/water/hydrochloric acid mixture, and the whole is refluxed for 2 hours. The solvents are evaporated to dryness to give the sought dihydrochloride of bis(4-((aminomethyl)alkyl)-diphenylalkane. The free bis-amine is obtained by treatment of an aqueous solution of hydrochloride in the presence of a mineral base, followed by extraction with dichloromethane. The organic phase is dried over sodium sulphate, filtered and evaporated under reduced pressure.

2) bis(4-(N,N'-di-Boc) guanidinoalkyl)phenyl)alkane

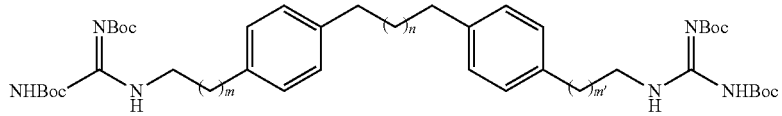

The dihydrochloride of bis(4-aminoalkyl)phenyl)alkane is suspended in anhydrous CH$_2$Cl$_2$ and solubilized by adding a minimum of MeOH. Triethylamine is then added, as well as N,N'-bis(tert-butoxycarbonyl)-N''-triflylguanidine and the whole is stirred at ambient temperature under an inert atmosphere. The solvent is removed by evaporation under vacuum. The crude product obtained is solubilized with CH$_2$Cl$_2$, washed with a 2M aqueous solution of NaHSO$_4$, then with a saturated aqueous solution of NaHCO$_3$. The organic phase is then dried over Na$_2$SO$_4$, filtered, concentrated and dried under vacuum to give the protected compound.

3) bis(4-guanidinoalkyl)phenyl)alkane

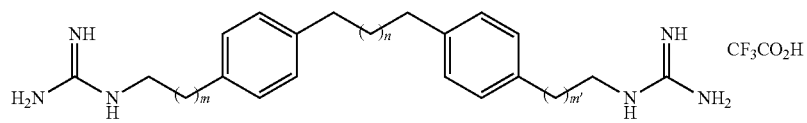

The compound bis(4-(N,N'-di-Boc)guanidinoalkyl)phenyl)alkane is dissolved in anhydrous CH$_2$Cl$_2$ and TFA is added. The reaction mixture is stirred under an inert atmosphere for about 3 h. The mixture is then concentrated, taken up in dichloromethane several times and concentrated to remove the maximum amount of the residual TFA. The product obtained is then triturated in Et$_2$O to give a solid which is then filtered, washed with Et$_2$O and dried under vacuum. It is the sought compound bis(trifluoroacetate) of bis(4-(guanidinoalkyl)phenyl)alkane.

Example 7

Synthesis of bis(4-(amidinoalkyl)phenyl)alkanes

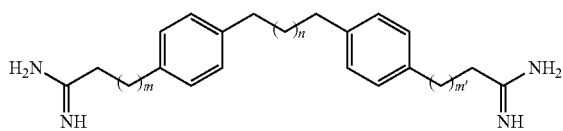

A solution of bis(4-(cyanoalkyl)phenyl)alkane derivative in a mixture of ethanol and anhydrous benzene is cooled to 0° C., then it is treated by bubbling with gaseous hydrochloric acid for about 1 hour. The acid solution is stored at 4° C. for several days. The volatile part of the hydrochloric acid is removed by bubbling with dry nitrogen, and the degassed solution is evaporated to dryness under reduced pressure. The evaporation residue, containing the dihydrochloride of bis(4-(ethyl)imidatoalkyl)phenyl)alkane, is taken up in a 1M solution of ammonia in ethanol. The mixture is heated at 50-60° C. under anhydrous conditions for 2-3h, then it is stirred overnight at ambient temperature. The resultant mixture is filtered, then diethyl ether is added, causing precipitation of the sought dihydrochloride of bis(4-(amidinoalkyl)phenyl)alkane.

B. Determination of Biological Activity

Material Used
Bacterial Strains
According to the joint recommendations:
of the "Comite de l'Antibiogramme de la Société Française de Microbiologie" (Antibiogram Committee of the French Society of Microbiology) (CA-SFM) [CA-SFM. Communique 2007 (Edition of January 2007). http://www.sfm.asso.fr] and,
of the "Clinical and Laboratory Standards Institute" (CLSI, formerly "National Committee for Clinical Laboratory Standards" or NCCLS) [NCCLS. 2003. *Methods for dilution antimicrobial susceptibility tests for bacteria that grow aerobically; approved standard M7-A6*, 6th ed. National Committee for Clinical Laboratory Standards, Wayne, Pa., USA.], five reference bacterial strains were used for the study: *Escherichia coli* ATCC 25922, *Pseudomonas aeruginosa* ATCC 27853, *Staphylococcus aureus* ATCC 25923 & ATCC 29213 and *Enterococcus faecalis* ATCC 29212.

The study also included 5 clinical isolates, obtained from rectal samples and/or from haemoculture:
penicillin-producing *E. coli* (EcR1),
methicillin-resistant *S. aureus* (mecA gene) (SaR1),
vancomycin-resistant *E. faecium* (vanB gene) (EfR1),
*E. faecalis* resistant to teicoplanin and to vancomycin (vanA gene) (EfR2), and
*P. aeruginosa* overexpressing an efflux pump (PaR1).

The isolates were selected on the basis of their resistance profile. The resistance profiles were determined on VITEK2 (BioMérieux, France).

The bacteria are cultivated either on Mueller-Hinton agar (Difco, 225250), or in Mueller-Hinton broth (Difco, 275730), at 35° C. [Grare M, Mourer M, Fontanay S, Regnouf-de-Vains J B, Finance C, Duval R E. In vitro activity of para-guanidinoethylcalix[4]arene against susceptible and antibiotic-resistant Gram-negative and Gram-positive bacteria. *J. Antimicrob Chemother.* 2007; 60: 575-81].

Active Ingredients

The various molecules tested were prepared in the form of aqueous solution at $10^{-2}$ mol/L. The solutions used for the biological tests are freshly prepared, and stored for a week at most, at 4° C. The solutions are filtered through a filter with pores of 0.22 µm (Millex®GP; 0.22 µm; Millipore; France) before each test.

Thirteen active ingredients were tested: the guanidino compounds 1, 3, 4, 6, 7, 9 and 10 in the form of salts of trifluoroacetic acid, the amidino compounds 103, 104, 106, 107, 108 and 110 in the form of salts of hydrochloric acid, as well as chlorhexidine in the form of salt of gluconic acid, and hexamidine in the form of salt of isethionic acid, which are commercially available antibacterials, by way of comparison.

1

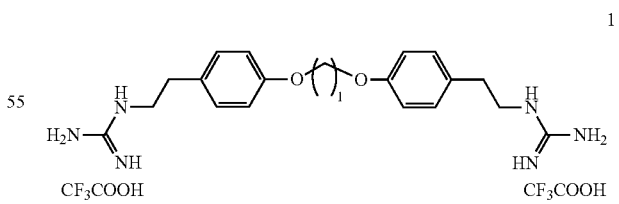

3

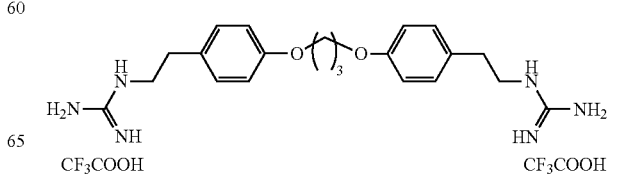

Example 8

Determination of Antibacterial Activity

Procedure for determining the Minimum Inhibitory Concentration (MIC)

The minimum inhibitory concentrations (MIC) were determined by the standardized method of microdilution in liquid medium (96-well microplate, U-shaped bottom, Greiner), in Mueller-Hinton broth, with a final inoculum of $10^5$-$10^6$ CFU/mL, depending on the bacterial species, in accordance with the recommendations of the CLSI.

For the determination of MIC, bacterial suspensions are prepared from an isolated colony, taken from a Mueller-Hinton agar, taken up in 5 mL of Mueller-Hinton broth. After 24 h of growth, the bacterial suspensions are diluted in sterile distilled water in order to obtain an inoculum of $10^5$-$10^6$ CFU/mL. The purity of the bacterial suspensions is tested by isolation on agar and Gram staining.

After incubation for 18 to 24 h at 35° C., the MIC values are determined using an ELISA plate reader (at 540 nm, Multiskan E X, Thermo Electron Corporation, France) as the concentrations of active ingredient for which the absorbance is comparable to that of the negative control (culture medium alone or with the drug, without inoculum). The results are the mean value of 4 independent experiments.

Results

The minimum inhibitory concentrations (MIC) are given in Table 3.

TABLE 3

MIC values (mg/L) obtained by the method of microdilution in liquid medium, according to the procedures of the CLSI and the CA-SFM.

| Molecules tested | | CHX | HX | 1 | 3 | 4 | 6 | 7 | 9 | 10 |
|---|---|---|---|---|---|---|---|---|---|---|
| Reference strains | | | | | | | | | | |
| E. coli | ATCC 25922 | 0.25 | 8 | 64 | 32 | 32 | 4 | 4 | 1 | <1-2 |
| S. aureus | ATCC 25923 | 0.5 | 4 | 16 | 4 | 2 | 0.5 | 1 | 0.25 | <1 |
| S. aureus | ATCC 29213 | 0.5 | <1 | 8 | 2 | 1 | 0.25 | 1 | 0.25 | <1 |
| E. faecalis | ATCC 29212 | 2 | 2 | 256 | 128 | 64 | 8 | 8 | 1-2 | <1 |
| P. aeruginosa | ATCC 27853 | 8 | 32 | 64 | 64 | 64 | 16 | 16 | 4 | 8 |
| Clinical isolates | | | | | | | | | | |
| penicillinase-producing E. coli | | 0.5 | 8 | nd | nd | nd | 4 | nd | nd | nd |
| MRSA (mecA gene) | | 0.5 | 2 | nd | nd | nd | <1 | nd | nd | nd |
| E. faecium (vanB gene) | | 1 | 2 | nd | nd | nd | 8 | nd | nd | nd |
| E. faecalis (vanA gene) | | 2 | 4 | nd | nd | nd | 16 | nd | nd | nd |
| P. aeruginosa (overexpression of the efflux pumps) | | 8 | 64 | nd | nd | nd | 32 | nd | nd | nd |

| Molecules tested | | CHX | HX | 103 | 104 | 105 | 106 | 107 | 108 | 109 | 110 |
|---|---|---|---|---|---|---|---|---|---|---|---|
| Reference strains | | | | | | | | | | | |
| E. coli | ATCC 25922 | 0.25 | 8 | 128 | 64 | | 32 | 64 | 32 | | 4 (2) 8 (1) |
| S. aureus | ATCC 25923 | 0.5 | 4 | 32 | 2 | 4 (2) 2 (1) | | 4-8-16 | 2 (2) 4 (1) | | 1 |
| S. aureus | ATCC 29213 | 0.5 | <1 | 32 | 2 | 2 | | 2-4-32 | 2 (2) 16 (1) | | 1 |
| E. faecalis | ATCC 29212 | 2 | 2 | 256 | 256 | | 32 | 32 | 8 | | 2 |
| P. aeruginosa | ATCC 27853 | 8 | 32 | 128 | 64 | | 32 | 64 | 16 | | 16 |

1: 1,1-bis(4-(2-guanidinoethyl)phenoxy)methane;
3: 1,3-bis(4-(2-guanidinoethyl)phenoxy)propane;
4: 1,4-bis(4-(2-guanidinoethyl)phenoxy)butane;
6: 1,6-bis(4-(2-guanidinoethyl)phenoxy)hexane;
7: 1,7-bis(4-(2-guanidinoethyl)phenoxy)heptane;
9: 1,9-bis(4-(2-guanidinoethyl)phenoxy)nonane;
10: 1,10-bis(4-(2-guanidinoethyl)phenoxy)decane;
103: 1,3-bis(4-(2-amidinoethyl)phenoxy)propane;
104: 1,4-bis(4-(2-amidinoethyl)phenoxy)butane;
105: 1,5-bis(4-(2-amidinoethyl)phenoxy)pentane;
106: 1,6-bis(4-(2-amidinoethyl)phenoxy)hexane;
107: 1,7-bis(4-(2-amidinoethyl)phenoxy)heptane;
108: 1,8-bis(4-(2-amidinoethyl)phenoxy)octane;
109: 1,9-bis(4-(2-amidinoethyl)phenoxy)nonane;
110: 1,10-bis(4-(2-amidinoethyl)phenoxy)decane.
nd: not determined Firstly, hexamidine and chlorhexidine both display broad-spectrum antibacterial activity (i.e. antibacterial activity against Gram-positive and Gram-negative bacteria), with less activity on *P. aeruginosa* for both these molecules (hexamidine and chlorhexidine).

Moreover, hexamidine and chlorhexidine display comparable antibacterial activity, whether the reference bacteria (ATCC strains) or the clinical isolates are considered. Finally, hexamidine and chlorhexidine display better activity on Gram-positive cocci (*S. aureus* and *Enterococcus* spp.), apart from chlorhexidine with respect to the bacterium *E. coli*.

Secondly, regarding the compounds according to the invention, the antibacterial activity varies in relation to the length of the alkyl chain (guanidino: n=9>n=10>n=6>n=4≥n=3>n=1; amidino: n=10>n=6≥n=4). These molecules display activity on Gram-positive and Gram-negative bacteria, with stronger activity on Gram-positive cocci (and more particularly *Staphylococcus* spp. and *S. aureus*), and 6 maintains comparable activity on the clinical isolates.

Compound 6 displays antibacterial activity that is better overall than hexamidine and is comparable to that of chlorhexidine, in particular with regard to its activity against Staphylococci.

Compounds 9 and 10 both display very good activities on the 5 reference strains tested, equivalent to or greater than those of compound 6.

Example 9

Determination of Cellular Viability and Cytotoxicity

Cell Lines and Cellular Culture

The eukaryotic cells used in our study are HaCaT cells (human keratinocytes), which were kindly supplied by the Pierre Fabre Institute (Toulouse, France); and MRC-5 cells (human embryonic fibroblasts), which were obtained from the company BioMérieux (Lyons, France). These cells are cultivated in DMEM ("Dulbecco's modified Eagle's medium", Invitrogen 61965) for the HaCaT cells, and MEM ("modified Eagle's medium", Invitrogen 41090); 10% of fetal calf serum (FCS, Invitrogen, 10270, Batch 40Q5150K)

in a humid chamber at 37° C., under 5% $CO_2$. The HaCaT and MRC-5 cells were seeded at $10^4$ cells/well in 96-well plates (Sarstedt 831835). After 48 h of growth, the culture medium is withdrawn and replaced with the various "test" solutions (volume=100 µL). After contact time of 24, 48 and/or 168 H, the viability or cytotoxicity tests are carried out.

Procedure of the Biological Tests a) Cellular Viability Tests (MTT Test)

In order to evaluate the effect of the various compounds tested on the viability of HaCaT and MRC-5 cells, the MTT technique (3-[4,5-dimethylthiazol-2-yl]-2,5-diphenyltetrazolium bromide; MTT, Aldrich, 135038), described by Mosmann [Mosmann T. Rapid colorimetric assay for cellular growth and survival: application to proliferation and cytotoxicity assays. *J Immunol Methods*. 1983; 65: 55-63] and modified by Grare et al. [Grare M, Mourer M, Fontanay S, Regnouf-de-Vains J B, Finance C, Duval R E. In vitro activity of para-guanidinoethylcalix[4]arene against susceptible and antibiotic-resistant Gram-negative and Gram-positive bacteria. *J Antimicrob Chemother*. 2007; 60: 575-81], was used.

It is based on the reduction of yellow tetrazolium salts to purple crystals of formazan, mainly by mitochondrial dehydrogenases. The quantity of formazan formed is proportional to the number of live cells. After the contact times of 24, 48 and/or 168 h with the different concentrations of the test molecules, 10 nl of MTT (at 5 mg/mL) is added to each well and the plates are placed at 37° C. After incubation for 4 H, the insoluble crystals of formazan that have formed are dissolved by adding 100 µL SDS to each well. The absorbance is measured at 540 nm with a reference wavelength at 690 nm, using an ELISA plate reader (Multiskan E X, Thermo Electron Corporation, France). The results are the mean of the values obtained for 8 wells per concentration and per unit time. Each experiment was carried out 3 times.

b) Cytotoxicity Tests (Neutral Red Test)

The cytotoxicity test is based on incorporation of a vital dye, Neutral Red, in the lysosomes of the viable cells, after exposure of the cells to different concentrations of the test molecules. The quantity of dye, after extraction from the lysosomes, is quantified by means of a spectrophotometer and compared with that obtained in the case of "control" cells, not exposed to the test molecules.

The test was carried out as described previously [Borenfreund E, Puerner J A. Toxicity determined in vitro by morphological alterations and neutral red absorption. *Toxicol Lett* 1985; 24: 119-24, and Grare M, Mourer M, Fontanay S, Regnouf-de-Vains J B, Finance C, Duval R E. In vitro activity of para-guanidinoethylcalix[4]arene against susceptible and antibiotic-resistant Gram-negative and Gram-positive bacteria. *J Antimicrob Chemother*. 2007; 60: 575-81].

After contact times of 24, 48 and/or 168 h with the different concentrations of the test molecules, the medium contained in each well is withdrawn and replaced with 200 µL of medium without phenol red (Invitrogen, 51200) containing 50 µg/mL of Neutral Red for an additional 3 h of incubation. The cells are then rinsed 3 times with PBS solution. After the last washing with PBS, 200 µL of a solution with 1% acetic acid/50% ethanol is added to each well to extract the dye from the lysosomes of the viable cells. The absorbance is measured at 540 nm, with a reference wavelength at 690 nm, by means of an ELISA plate reader (Multiskan E X, Thermo Electron Corporation, France). The results are the mean of the values obtained for 8 wells per concentration and per unit time. Each experiment was carried out 3 times.

Results

The results for viability and cytotoxicity are given in Tables 4 and 5.

TABLE 4

$IC_{50}$ determined from the values obtained by the viability test (with MTT).

| $IC_{50}$ (mg/L) | Chlorhexidine | | Hexamidine | | 6 | |
|---|---|---|---|---|---|---|
| | HaCaT | MRC-5 | HaCaT | MRC-5 | HaCaT | MRC-5 |
| 24 h | 8-16 | 16-32 | 32-64 | 32-64 | 4-8 | 8-16 |
| 48 h | 4-8 | 8-16 | 16-32 | 16-32 | 4-8 | 4-8 |
| 168 h | 2-4 | 1-2 | 4-8 | 4-8 | 1-2 | 0.5-1 |

The HaCaT and MRC-5 cell lines were cultivated as adherent culture on 96-well microplates.
The compounds were added at concentrations from 1 to 256 mg/L for 24, 48 and 168 h.
The $IC_{50}$ are representative of three independent determinations.
6: 1, 6-bis(4-(2-guanidinoethyl)phenoxy)hexane.

TABLE 5

$CC_{50}$ determined from the values obtained by the cytotoxicity test (with NR).

| $CC_{50}$ (mg/L) | Chlorhexidine | | Hexamidine | | 6 | |
|---|---|---|---|---|---|---|
| | HaCaT | MRC-5 | HaCaT | MRC-5 | HaCaT | MRC-5 |
| 24 h | 8-16 | 8-16 | 8-16 | 8-16 | 4-8 | 4-8 |
| 48 h | 4-8 | 2-4 | 8-16 | 8-16 | 2-4 | |
| 168 h | 1-2 | 0.5-1 | 1-2 | 0.5-1 | 1-2 | |

The HaCaT and MRC-5 cell lines were cultivated as adherent culture on 96-well microplates.
The compounds were added at concentrations from 1 to 256 mg/L for 24, 48 and 168 h.
The $CC_{50}$ are representative of three independent determinations.
6: 1, 6-bis(4-(2-guanidinoethyl)phenoxy)hexane Comparison of the results of the viability and cytotoxicity tests shows that the concentrations $IC_{50}$ (inhibitory concentration at 50%) and $CC_{50}$ (cytotoxic concentration at 50%) obtained are in agreement overall. Comparison of the values of $IC_{50}$ and of $CC_{50}$ shows that the values are of the same order of magnitude in the case of hexamidine and chlorhexidine, and those obtained for compound 6 are somewhat lower. Consequently compound 6 has a slightly less pronounced effect on viability and cytotoxicity, in vitro, on HaCaT and/or MRC5 eukaryotic cells.

Example 10

Determination of the Selectivity Index

The selectivity index ($SI=IC_{50}/MIC$) was calculated from the MIC and $IC_{50}$ concentrations determined after 24 h of exposure (Table 4). The values of SI obtained for the two tests (MTT and NR) are similar.

TABLE 6

Selectivity index obtained for 5 reference strains, after exposure for 24 h to the compound, on HaCaT cell lines.

| | Chlorhexidine | Hexamidine | 6 |
|---|---|---|---|
| E. coli ATCC 25922 | 64-128 | 4-8 | 1-2 |
| S. aureus ATCC 25923 | 32-64 | 8-16 | 8-16 |
| S. aureus ATCC 29213 | 32-64 | ≥32 | 16-32 |
| E. faecalis ATCC 29212 | 8-16 | 16-32 | 0.5-1 |
| P. aeruginosa ATCC 27853 | 2-4 | 1-2 | 0.25-0.5 |

6: 1,6-bis(4-(2-guanidinoethyl)phenoxy)hexane.

Overall, the values of SI are very similar to one another, which demonstrates the advantage of compound 6 with respect to "commercial" compounds widely recommended "in town and hospital" for infections with Gram-positive bacteria, and more particularly infections with *S. aureus*.

The invention claimed is:
1. A pharmaceutical composition, comprising a pharmaceutically acceptable vehicle and 0.1 to 1% by weight of a compound of the following formula (VI) as an active ingredient:

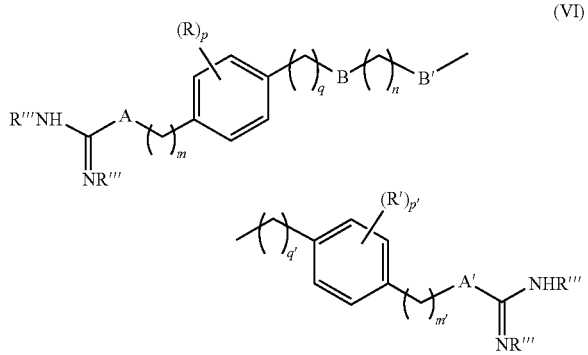

in which:
n represents an integer from 1 to 12,q and q' represent, independently of one another, integers from 0 to 2,
p and p' represent, independently of one another, integers from 0 to 4,
B and B' represent, independently of one another, an oxygen atom or a $CH_2$ group,
R and R' represent, independently of one another, a halogen selected from chlorine, bromine, iodine or fluorine atoms, or a linear or branched alkyl group with 1 to 3 carbon atoms,
R''' represents a hydrogen or a group protecting the amine function selected from the groups Boc, Fmoc, Bn, Z,
if A and A' represent, independently of one another, a $CH_2$ group, then m and m' represent, independently of one another, integers from 1 to 8, and
if A and A' represent, independently of one another, an NH group or an NR'' group, in which R'' is a linear or branched alkyl group with 1 to 3 carbon atoms, then m and m' represent, independently of one another, integers from 2 to 8, or
a physiologically acceptable acid salt derived from a compound of formula (VI) selected from a hydrochloride, a formate, a trifluoroacetate or an oxalate (HOOCCOOH),
the compounds of the following formulae being excluded:

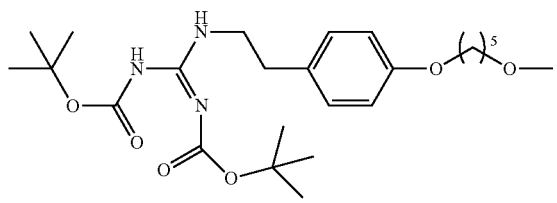

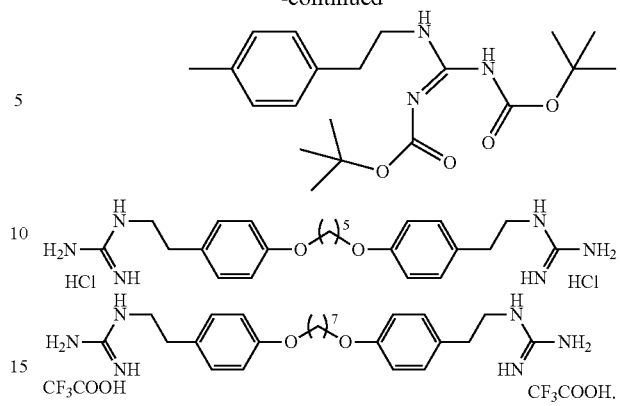

2. The pharmaceutical composition according to claim 1, wherein the compound is of the following formula (I):

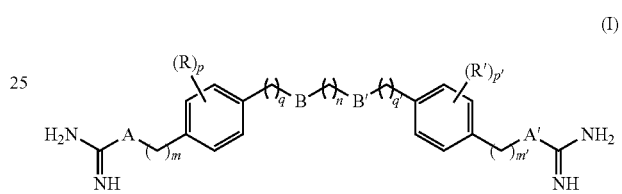

in which:
n represents an integer from 1 to 12,
q and q' represent, independently of one another, integers from 0 to 2,
p and p' represent, independently of one another, integers from 0 to 4,
B and B' represent, independently of one another, an oxygen atom or a $CH_2$ group,
R and R' are, independently of one another, a halogen selected from chlorine, bromine, iodine or fluorine atoms, or a linear or branched alkyl group with 1 to 3 carbon atoms,
if A and A' represent, independently of one another, a $CH_2$ group, then m and m' represent, independently of one another, integers from 1 to 8,and
if A and A' represent, independently of one another, an NH group or an NR'' group, in which R'' is a linear or branched alkyl group with 1 to 3 carbon atoms, then m and m' represent, independently of one another, integers from 2 to 8,
or a physiologically acceptable acid salt derived from a compound of formula (I) selected from a hydrochloride, a formate, a trifluoroacetate or an oxalate (HOOCCOOH),
the compounds of the following formulae being excluded:

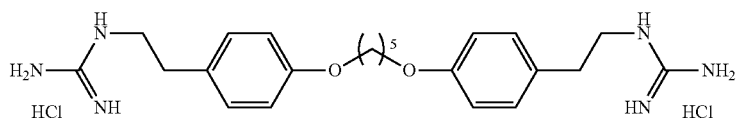

-continued

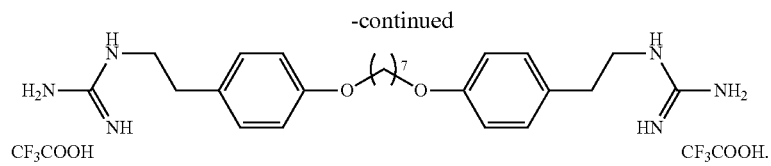

3. The pharmaceutical composition according to claim 1, wherein the compound is of the following formula (II):

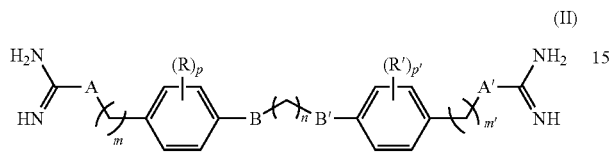

(II)

in which A, A', B, B', R, R', m, m', n, p, p' are as defined above, or
a physiologically acceptable acid salt derived from a compound of formula (II) selected from a hydrochloride, a formate, a trifluoroacetate or an oxalate (HOOCCOOH).

4. The pharmaceutical composition according to claim 1, wherein the compound is of the following formula (III):

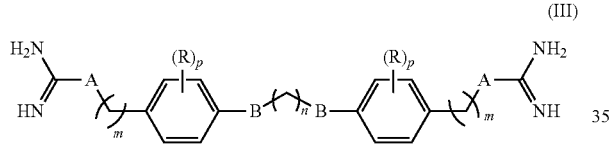

(III)

in which A, B, R, m, n, p are as defined above, or
a physiologically acceptable acid salt derived from a compound of formula (III) selected from a hydrochloride, a formate, a trifluoroacetate or an oxalate (HOOCCOOH).

5. The pharmaceutical composition according to claim 1, wherein the compound is of the following formula (IV):

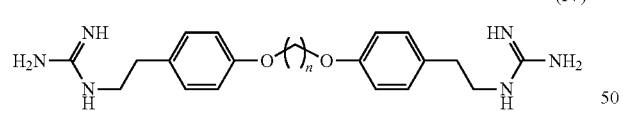

(IV)

in which n represents 1, 2, 3, 4, 5, 6, 7, 8, 9, 10, 11 or 12, or
a physiologically acceptable acid salt derived from a compound of formula (IV), or
a compound of the following formula 6:

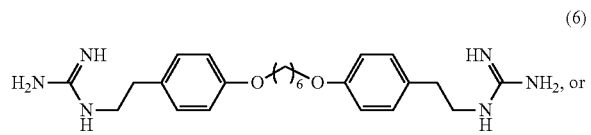

(6)

a physiologically acceptable acid salt derived from a compound of formula (6) selected from a hydrochloride, a formate, a trifluoroacetate or an oxalate (HOOCCOOH).

6. The pharmaceutical composition according to claim 1, wherein,
m is different from m', and/or
p is different from p', and/or
R is different from R', and/or
A is different from A', and/or
B is different from B'.

7. The pharmaceutical composition according to claim 1, wherein the active ingredient is a compound according to formula (II):

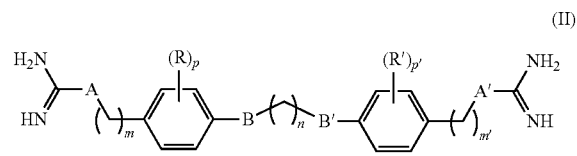

(II)

in which A, A', B, B', R, R', m, m', n, p, p' are as defined above, for which the sum (m+m'+n) is less than or equal to 10, or
a physiologically acceptable acid salt derived from a compound of formula (II) selected from a hydrochloride, a formate, a trifluoroacetate or an oxalate (HOOCCOOH), or
a compound according to formula (III):

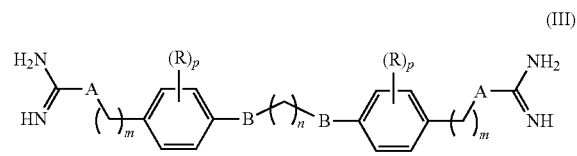

(III)

in which A, B, R, m, n, p are as defined above, for which the sum (2m+n) is less than or equal to 10, or a physiologically acceptable acid salt derived from a compound of formula (III) selected from a hydrochloride, a formate, a trifluoroacetate or an oxalate (HOOCCOOH),
said pharmaceutical composition being formulated in aqueous solution.

8. The pharmaceutical composition according to claim 1, wherein the active ingredient is a compound according to formula (II):

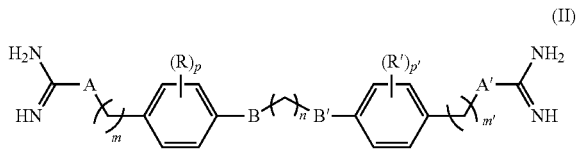

(II)

in which A, A', B, B', R, R', m, m', n, p, p' are as defined above, for which the sum (m+m'+n) is greater than 10, or a physiologically acceptable acid salt derived from a compound of formula (II) selected from a hydrochloride, a formate, a trifluoroacetate or an oxalate (HOOCCOOH), or a compound according to formula (III):

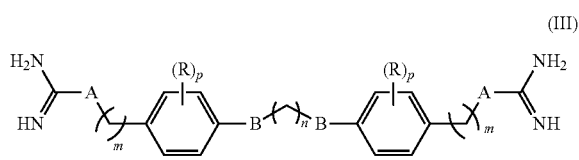

(III)

in which A, B, R, m, n, p are as defined above, for which the sum (2m+n) is less than or equal to 10, or a physiologically acceptable acid salt derived from a compound of formula (III) selected from a hydrochloride, a formate, a trifluoroacetate or an oxalate (HOOCCOOH), said pharmaceutical composition being formulated in aqueous-alcoholic solution.

9. The pharmaceutical composition according to claim 1, wherein the composition is configured to be administered topically.

10. A method for preparing a compound of formula (Ia), comprising:

a) cleaving protecting groups Y of a compound of the following formula (X'):

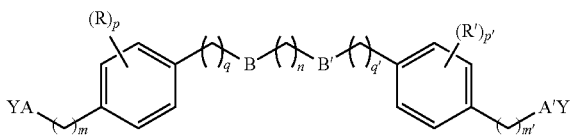

(X')

in which:

n represents an integer from 1 to 12, m and m' represent, independently of one another, integers from 2 to 8, q and q' represent, independently of one another, integers from 0 to 2, p and p' represent, independently of one another, integers from 0 to 4, A and A' represent, independently of one another, an NH group or an NR" group, in which R" is a linear or branched alkyl group with 1 to 3 carbon atoms, B and B' represent, independently of one another, an oxygen atom or a CH$_2$ group, R and R' represent, independently of one another, a halogen selected from chlorine, bromine, iodine or fluorine atoms, or a linear or branched alkyl group with 1 to 3 carbon atoms, Y represents a group protecting the amines Boc or Fmoc, to obtain:

a compound of the following formula (XI'):

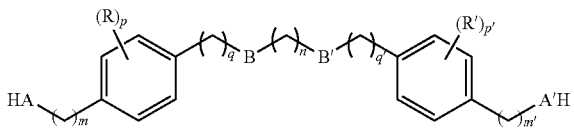

(XI')

in which:

n represents an integer from 1 to 12, m and m' represent, independently of one another, integers from 2 to 8, q and q' represent, independently of one another, integers from 0 to 2, p and p' represent, independently of one another, integers from 0 to 4, A and A' represent, independently of one another, an NH group or an NR" group, in which R" is a linear or branched alkyl group with 1 to 3 carbon atoms, B and B' represent, independently of one another, an oxygen atom or a CH$_2$ group, R and R' represent, independently of one another, a halogen selected from chlorine, bromine, iodine or fluorine atoms, or a linear or branched alkyl group with 1 to 3 carbon atoms, or an acid salt derived from a compound of formula (XI') selected from a hydrochloride, a formate, a trifluoroacetate or an oxalate (HOOCCOOH);

b) reacting the compound of formula (XI') formed during stage a) with a compound of the following formula (XII):

(XII)

in which GP represents a leaving group selected from —SR, -NTf or

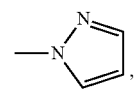

and Y represents a group protecting the amines Boc or Fmoc, to obtain a compound of the following formula (XIII'):

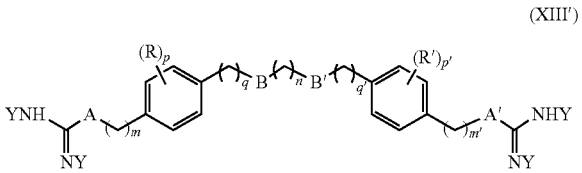

(XIII')

in which:
n represents an integer from 1 to 12,
m and m' represent, independently of one another, integers from 2 to 8,
q and q' represent, independently of one another, integers from 0 to 2,
p and p' represent, independently of one another, integers from 0 to 4,
A and A' represent, independently of one another, an NH group or an NR" group, in which R" is a linear or branched alkyl group with 1 to 3 carbon atoms,
B and B' represent, independently of one another, an oxygen atom or a CH$_2$ group,
R and R' represent, independently of one another, a halogen selected from chlorine, bromine, iodine or fluorine atoms, or a linear or branched alkyl group with 1 to 3 carbon atoms, and
Y represents a group protecting the amines Boc or Fmoc; and
c) deprotecting the amine functions of the compound of formula (XIII') obtained in stage b) to obtain a compound of the following formula (Ia):

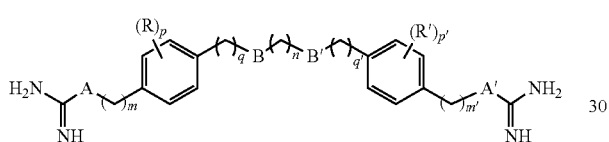

(Ia)

in which:
n represents an integer from 1 to 12,
m and m' represent, independently of one another, integers from 2 to 8,
q and q' represent, independently of one another, integers from 0 to 2,
p and p' represent, independently of one another, integers from 0 to 4,
A and A' represent, independently of one another, an NH group or an NR" group, in which R" is a linear or branched alkyl group with 1 to 3 carbon atoms,
B and B' represent, independently of one another, an oxygen atom or a CH$_2$ group,
R and R' are, independently of one another, a halogen selected from chlorine, bromine, iodine or fluorine atoms, or a linear or branched alkyl group with 1 to 3 carbon atoms, or
an acid salt derived from a compound of formula (Ia) selected from a hydrochloride, a formate, a trifluoroacetate or an oxalate (HOOCCOOH).

11. The method according to claim 10, wherein the compound prepared is according to formula (IV), the method comprising:

a) cleaving the groups Y of a compound of the following formula (XX):

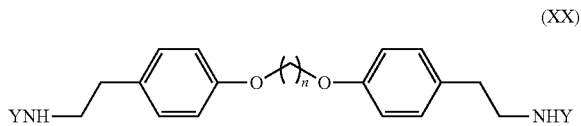

(XX)

in which n represents 1, 2, 3, 4, 5, 6, 7, 8, 9, 10, 11 or 12, and Y represents a group protecting the amines Boc or Fmoc,
to obtain:
a compound of the following formula (XXI):

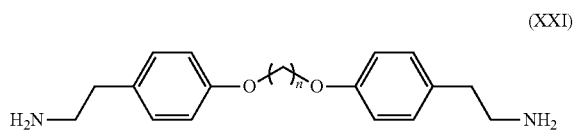

(XXI)

in which n represents 1, 2, 3, 4, 5, 6, 7, 8, 9, 10, 11 or 12,or an acid salt derived from a compound of formula (XXI) selected from a hydrochloride, a formate, a trifluoroacetate or an oxalate (HOOCCOOH);
b) reacting the compound of formula (XXI) formed during stage a) with a compound of the following formula (XII):

(XII)

in which GP represents a leaving group selected from —SR, -NTf or

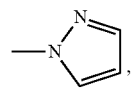

and Y represents a group protecting the amines Boc or Fmoc,
to obtain a compound of formula (XXII):

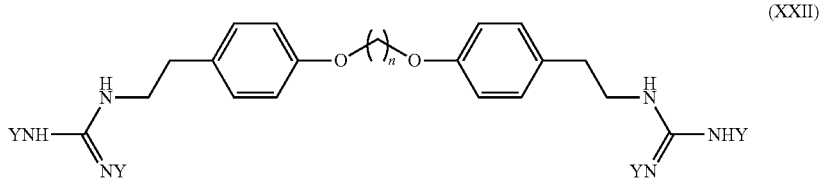

(XXII)

in which n represents 1, 2, 3, 4, 5, 6, 7, 8, 9, 10, 11 or 12,and Y represents a group protecting the amines Boc or Fmoc, and
c) deprotecting the amine functions of the compound of formula (XXII) obtained in stage b) to obtain a compound of formula (IV):

(IV)

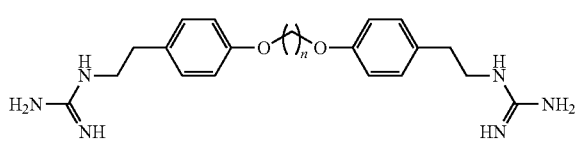

in which n represents 1, 2, 3, 4, 5, 6, 7, 8, 9, 10, 11 or 12, or an acid salt derived from a compound of formula (IV) selected from a hydrochloride, a formate, a trifluoroacetate or an oxalate (HOOCCOOH).

12. A pharmaceutical composition, configured to be administered topically, comprising as an active ingredient at least one compound, in a range of 0.1 to 1% by weight, of the following formula (VI):

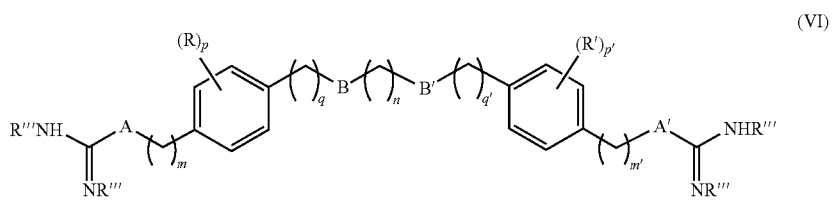

(VI)

in which:
  n represents an integer from 1 to 12,
  q and q' represent, independently of one another, integers from 0 to 2,
  p and p' represent, independently of one another, integers from 0 to 4,
  B and B' represent, independently of one another, an oxygen atom or a CH$_2$ group,
  R and R' represent, independently of one another, a halogen selected from chlorine, bromine, iodine or fluorine atoms, or a linear or branched alkyl group with 1 to 3 carbon atoms,
  R''' represents a hydrogen or a group protecting the amine function selected from the groups Boc, Fmoc, Bn, Z,
  if A and A' represent, independently of one another, a CH$_2$ group, then m and m' represent, independently of one another, integers from 1 to 8, and
  if A and A' represent, independently of one another, an NH group or an NR" group, in which R" is a linear or branched alkyl group with 1 to 3 carbon atoms, then m and m' represent, independently of one another, integers from 2 to 8, or
  a physiologically acceptable acid salt derived from a compound of formula (VI) selected from a hydrochloride, a formate, a trifluoroacetate or an oxalate (HOOCCOOH),
  the compounds of the following formulae being excluded:

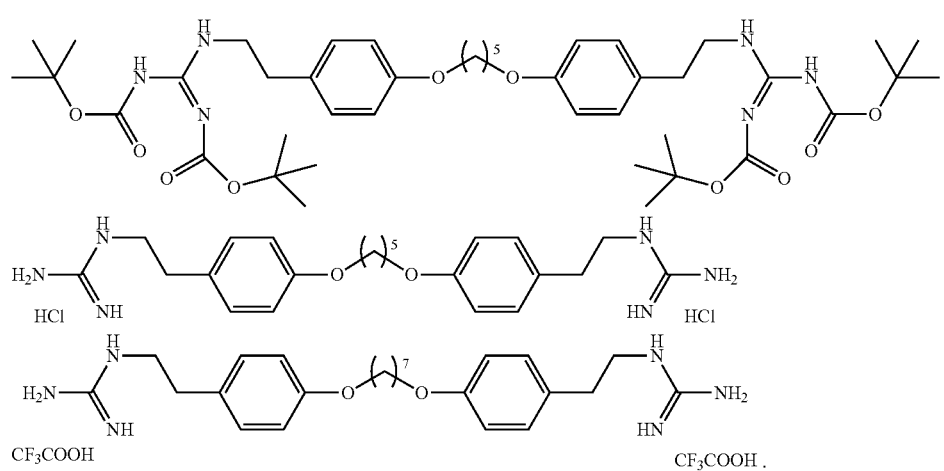

13. The pharmaceutical composition according to claim 12, wherein the at least one compound is selected from the group consisting of:
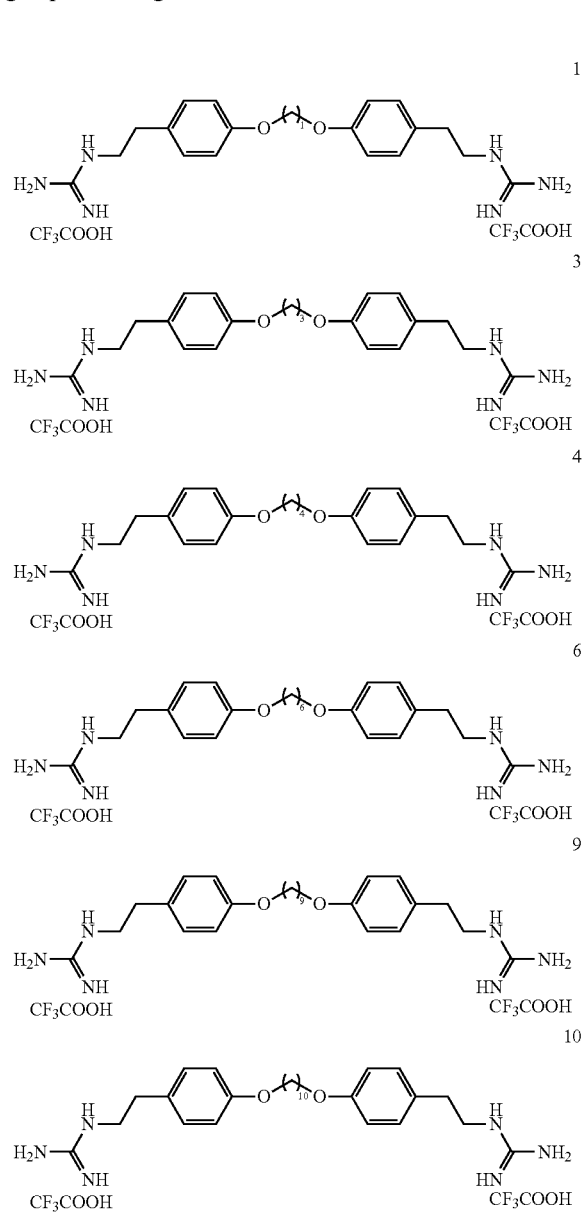
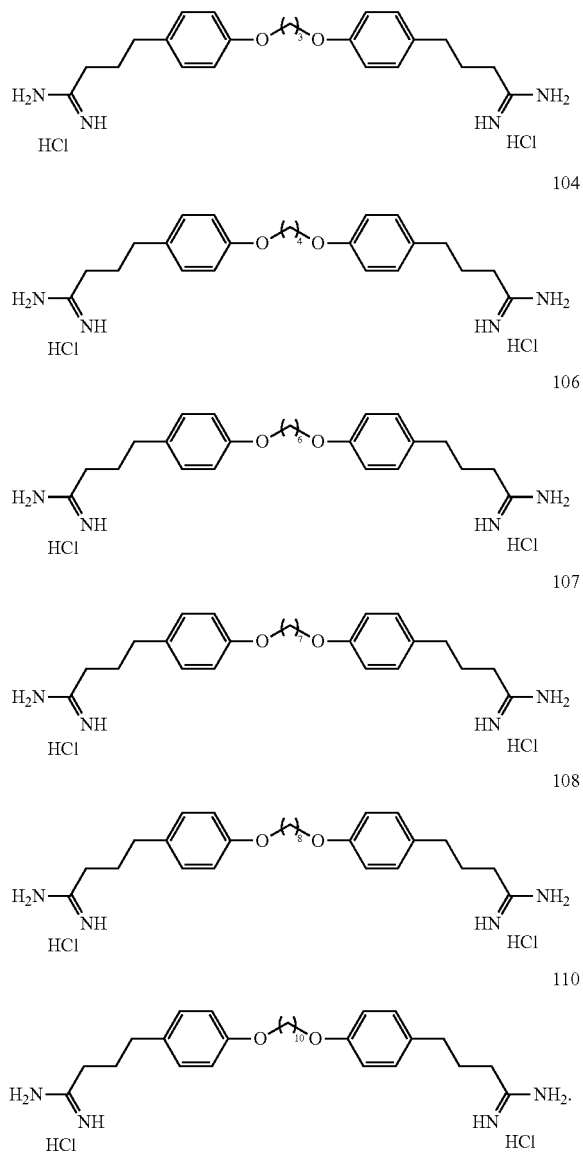
* * * * *

UNITED STATES PATENT AND TRADEMARK OFFICE
CERTIFICATE OF CORRECTION

PATENT NO. : 8,703,825 B2  Page 1 of 1
APPLICATION NO. : 13/003330
DATED : April 22, 2014
INVENTOR(S) : Duval et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this

Twenty-ninth Day of September, 2015

Michelle K. Lee
*Director of the United States Patent and Trademark Office*